United States Patent
Kihm et al.

(10) Patent No.: US 9,943,552 B2
(45) Date of Patent: *Apr. 17, 2018

(54) HUTC AS THERAPY FOR ALZHEIMER'S DISEASE

(71) Applicant: DePuy Synthes Products LLC, Raynham, MA (US)

(72) Inventors: Anthony J. Kihm, Princeton, NJ (US); Anna Gosiewska, Skillman, NJ (US)

(73) Assignee: DePuy Synthes Products, Inc., Raynham, MA (US)

( * ) Notice: Subject to any disclaimer, the term of this patent is extended or adjusted under 35 U.S.C. 154(b) by 433 days.

This patent is subject to a terminal disclaimer.

(21) Appl. No.: 14/244,426

(22) Filed: Apr. 3, 2014

(65) Prior Publication Data

US 2014/0234277 A1    Aug. 21, 2014

Related U.S. Application Data

(62) Division of application No. 12/748,170, filed on Mar. 26, 2010, now Pat. No. 8,722,034.

(60) Provisional application No. 61/163,619, filed on Mar. 26, 2009.

(51) Int. Cl.
| | |
|---|---|
| *A61K 35/12* | (2015.01) |
| *A61K 35/50* | (2015.01) |
| *A61K 35/51* | (2015.01) |
| *C12N 15/00* | (2006.01) |
| *C12N 5/073* | (2010.01) |
| *C12N 5/10* | (2006.01) |
| *C12N 15/63* | (2006.01) |

(52) U.S. Cl.
CPC .............. *A61K 35/51* (2013.01); *A61K 35/50* (2013.01); *C12N 5/0605* (2013.01); *A61K 35/12* (2013.01); *C12N 5/10* (2013.01); *C12N 15/63* (2013.01); *C12N 2509/00* (2013.01); *C12N 2510/00* (2013.01)

(58) Field of Classification Search
CPC ........ A61K 35/12; A61K 35/50; A61K 35/51; C12N 5/0605; C12N 15/00
See application file for complete search history.

(56) References Cited

U.S. PATENT DOCUMENTS

| | | | |
|---|---|---|---|
| 3,665,061 A | 5/1972 | Eberly, Jr. | |
| 4,193,992 A | 3/1980 | Fontaine | |
| 4,216,144 A | 8/1980 | Ashmead | |
| 4,352,883 A | 10/1982 | Lim | |
| 4,657,866 A | 4/1987 | Kumar | |
| 4,882,162 A | 11/1989 | Ikada et al. | |
| 4,963,489 A | 10/1990 | Naughton et al. | |
| 5,004,681 A | 4/1991 | Boyse et al. | |
| 5,192,553 A | 3/1993 | Boyse et al. | |
| 5,248,608 A | 9/1993 | Van Dooren et al. | |
| 5,286,632 A | 2/1994 | Jones | |
| 5,320,962 A | 6/1994 | Stiles et al. | |
| 5,342,761 A | 8/1994 | MacLeod | |
| 5,437,994 A | 8/1995 | Emerson et al. | |
| 5,443,950 A | 8/1995 | Naughton et al. | |
| 5,456,835 A | 10/1995 | Castino et al. | |
| 5,486,359 A | 1/1996 | Caplan et al. | |
| 5,580,777 A | 12/1996 | Bernard et al. | |
| 5,589,376 A | 12/1996 | Anderson et al. | |
| 5,670,483 A | 9/1997 | Zhang et al. | |
| 5,677,181 A | 10/1997 | Parish | |
| 5,684,032 A | 11/1997 | Elliott et al. | |
| 5,698,518 A | 12/1997 | Carson et al. | |
| 5,707,643 A | 1/1998 | Ogura et al. | |
| 5,736,516 A | 4/1998 | Louis | |
| 5,811,094 A | 9/1998 | Caplan et al. | |
| 5,827,735 A | 10/1998 | Young et al. | |
| 5,834,308 A | 11/1998 | Peck et al. | |
| 5,840,580 A | 11/1998 | Terstappen et al. | |
| 5,842,477 A | 12/1998 | Naughton et al. | |
| 5,843,780 A | 12/1998 | Thomson | |
| 5,855,619 A | 1/1999 | Caplan et al. | |
| 5,869,079 A | 2/1999 | Wong et al. | |
| 5,902,598 A | 5/1999 | Chen et al. | |
| 5,902,741 A | 5/1999 | Purchio et al. | |
| 5,906,934 A | 5/1999 | Grande et al. | |
| 5,919,702 A | 7/1999 | Purchio et al. | |
| 5,928,214 A | 7/1999 | Rubinstein et al. | |
| 5,942,225 A | 8/1999 | Bruder et al. | |

(Continued)

FOREIGN PATENT DOCUMENTS

| | | |
|---|---|---|
| CN | 1407088 | 2/2003 |
| JP | 2003-235549 | 8/2003 |
| JP | 2004-254682 | 9/2004 |
| WO | WO 90/11354 | 10/1990 |
| WO | WO 92/03917 | 3/1992 |
| WO | WO 93/04169 | 3/1993 |
| WO | WO 94/25584 | 11/1994 |
| WO | WO 95/17911 | 7/1995 |
| WO | WO 95/23216 | 7/1995 |
| WO | WO 96/01316 | 1/1996 |
| WO | WO 96/05309 | 2/1996 |
| WO | WO 98/17791 | 4/1998 |
| WO | WO 98/51317 | 11/1998 |
| WO | WO 99/03973 | 1/1999 |

(Continued)

OTHER PUBLICATIONS

Li et al, J. Mol. Neurosci. 34:157-163, 2008.*

(Continued)

*Primary Examiner* — Kevin K Hill

(74) *Attorney, Agent, or Firm* — Johnson & Johnson

(57) ABSTRACT

Methods for treating Alzheimer's disease, or the symptoms of Alzheimer's disease, are provided. Some embodiments are to methods for treatment comprising administering cells obtained from human umbilical cord tissue, or administering pharmaceutical compositions comprising such cells or prepared from such cells, such as cell derivatives. Some embodiments are to methods for treatment comprising hUTC. Pharmaceutical compositions for use in the inventive methods, as well as kits for practicing the methods are also provided.

10 Claims, 5 Drawing Sheets

(56) References Cited

U.S. PATENT DOCUMENTS

| | | |
|---|---|---|
| 5,955,343 A | 9/1999 | Holmes et al. |
| 5,962,325 A | 10/1999 | Naughton et al. |
| 5,994,094 A | 11/1999 | Hötten et al. |
| 6,001,647 A | 12/1999 | Peck et al. |
| 6,022,743 A | 2/2000 | Naughton et al. |
| 6,059,968 A | 5/2000 | Wolf |
| 6,140,039 A | 10/2000 | Naughton et al. |
| 6,171,610 B1 | 1/2001 | Vacanti et al. |
| 6,200,606 B1 | 3/2001 | Peterson et al. |
| 6,200,806 B1 | 3/2001 | Thomson |
| 6,214,369 B1 | 4/2001 | Grande et al. |
| 6,221,904 B1 | 4/2001 | Agus et al. |
| 6,251,090 B1 | 6/2001 | Avery et al. |
| 6,261,841 B1 | 7/2001 | Cohen et al. |
| 6,291,240 B1 | 9/2001 | Mansbridge et al. |
| 6,323,188 B1 | 11/2001 | Weissman |
| 6,326,201 B1 | 12/2001 | Fung et al. |
| 6,331,313 B1 | 12/2001 | Wong et al. |
| 6,333,029 B1 | 12/2001 | Vyakarnam et al. |
| 6,355,239 B1 | 3/2002 | Bruder et al. |
| 6,355,699 B1 | 3/2002 | Vyakamam et al. |
| 6,358,737 B1 | 3/2002 | Bonewald et al. |
| 6,372,494 B1 | 4/2002 | Naughton et al. |
| 6,375,972 B1 | 4/2002 | Guo et al. |
| 6,387,367 B1 | 5/2002 | Davis-Sproul et al. |
| 6,391,297 B1 | 5/2002 | Halvorsen |
| 6,429,013 B1 | 8/2002 | Halvorsen et al. |
| 6,436,704 B1 | 8/2002 | Roberts et al. |
| 6,444,205 B2 | 9/2002 | Dinsmore |
| 6,497,875 B1 | 12/2002 | Sorrell et al. |
| 6,511,511 B1 | 1/2003 | Slivka et al. |
| 6,528,245 B2 | 3/2003 | Sanchez-Ramos et al. |
| 6,534,084 B1 | 3/2003 | Vyakamam et al. |
| 6,555,374 B1 | 4/2003 | Gimble et al. |
| 6,599,323 B2 | 7/2003 | Melican et al. |
| 6,610,535 B1 | 8/2003 | Lu et al. |
| 6,638,765 B1 | 10/2003 | Rosenberg |
| 6,673,606 B1 | 1/2004 | Tennekoon et al. |
| 6,680,198 B1 | 1/2004 | Snyder et al. |
| 6,686,198 B1 | 2/2004 | Melton et al. |
| 6,699,837 B2 | 3/2004 | Nakamura |
| 6,703,017 B1 | 3/2004 | Peck et al. |
| 6,916,655 B2 | 7/2005 | Yasumoto et al. |
| 7,413,734 B2 | 8/2008 | Mistry et al. |
| 7,510,873 B2 | 3/2009 | Mistry et al. |
| 7,524,489 B2 | 4/2009 | Messina et al. |
| 7,560,276 B2 | 7/2009 | Harmon et al. |
| 7,875,272 B2 | 1/2011 | Messina et al. |
| 7,875,273 B2 | 1/2011 | Messina et al. |
| 8,277,796 B2 | 10/2012 | Messina et al. |
| 8,318,483 B2 | 11/2012 | Mistry et al. |
| 8,491,883 B2 | 7/2013 | Gosiewska et al. |
| 8,518,390 B2 | 8/2013 | Kramer et al. |
| 8,658,152 B2 | 2/2014 | Messina et al. |
| 8,703,121 B2 | 4/2014 | Harris et al. |
| 8,722,034 B2 * | 5/2014 | Kihm .................. C12N 5/0605 424/93.1 |
| 8,815,587 B2 | 8/2014 | Harris et al. |
| 9,234,172 B2 | 1/2016 | Mistry et al. |
| 2001/0024824 A1 | 9/2001 | Moss |
| 2001/0031256 A1 | 10/2001 | Edge |
| 2001/0046489 A1 | 11/2001 | Habener et al. |
| 2001/0055587 A1 | 12/2001 | Dinsmore et al. |
| 2002/0022676 A1 | 2/2002 | He et al. |
| 2002/0028510 A1 | 3/2002 | Sanberg et al. |
| 2002/0062151 A1 | 5/2002 | Altman et al. |
| 2002/0064519 A1 | 5/2002 | Bruder et al. |
| 2002/0081725 A1 | 6/2002 | Tsang et al. |
| 2002/0098584 A1 | 7/2002 | Palmer et al. |
| 2002/0119565 A1 | 8/2002 | Clarke et al. |
| 2002/0123141 A1 | 9/2002 | Hariri |
| 2002/0150986 A1 | 10/2002 | Lau |
| 2002/0151056 A1 | 10/2002 | Sasai et al. |
| 2002/0160471 A1 | 10/2002 | Kisiday et al. |
| 2002/0160510 A1 | 10/2002 | Hariri |
| 2002/0164307 A1 | 11/2002 | Habener et al. |
| 2002/0164791 A1 | 11/2002 | Van Der Kooy et al. |
| 2002/0168763 A1 | 11/2002 | Yan et al. |
| 2002/0182728 A1 | 12/2002 | Ramiya et al. |
| 2002/0187550 A1 | 12/2002 | Dinsmore et al. |
| 2002/0192816 A1 | 12/2002 | Roberts et al. |
| 2003/0003574 A1 | 1/2003 | Toma et al. |
| 2003/0007954 A1 | 1/2003 | Naughton et al. |
| 2003/0022369 A1 | 1/2003 | Fillmore et al. |
| 2003/0031657 A1 | 2/2003 | Habener et al. |
| 2003/0032178 A1 | 2/2003 | Williams et al. |
| 2003/0032179 A1 | 2/2003 | Hariri |
| 2003/0032183 A1 | 2/2003 | Sheridan |
| 2003/0049837 A1 | 3/2003 | Weiss et al. |
| 2003/0059939 A1 | 3/2003 | Page et al. |
| 2003/0082155 A1 | 5/2003 | Habener et al. |
| 2003/0082160 A1 | 5/2003 | Yu et al. |
| 2003/0096409 A1 | 5/2003 | Yasumoto et al. |
| 2003/0104997 A1 | 6/2003 | Black et al. |
| 2003/0109036 A1 | 6/2003 | Wu |
| 2003/0113910 A1 | 6/2003 | Levanduski |
| 2003/0118566 A1 | 6/2003 | Neuman et al. |
| 2003/0124721 A1 | 7/2003 | Cheatham et al. |
| 2003/0138948 A1 | 7/2003 | Fisk et al. |
| 2003/0138951 A1 | 7/2003 | Yin |
| 2003/0148513 A1 | 8/2003 | Sugaya et al. |
| 2003/0161818 A1 | 8/2003 | Weiss et al. |
| 2003/0162290 A1 | 8/2003 | Inoue et al. |
| 2003/0170215 A1 | 9/2003 | Tsang et al. |
| 2003/0175963 A1 | 9/2003 | Rosenberg |
| 2003/0180269 A1 | 9/2003 | Hariri |
| 2003/0186439 A1 | 10/2003 | Nakauchi et al. |
| 2003/0199447 A1 | 10/2003 | Goldman et al. |
| 2003/0203483 A1 | 10/2003 | Seshi |
| 2003/0203484 A1 | 10/2003 | Black et al. |
| 2003/0207450 A1 | 11/2003 | Young et al. |
| 2003/0211087 A1 | 11/2003 | Goldman |
| 2003/0211603 A1 | 11/2003 | Earp et al. |
| 2003/0211605 A1 | 11/2003 | Lee et al. |
| 2003/0212024 A1 | 11/2003 | Keating et al. |
| 2003/0219894 A1 | 11/2003 | Seino et al. |
| 2003/0228295 A1 | 12/2003 | Svendsen |
| 2003/0232752 A1 | 12/2003 | Freeman et al. |
| 2003/0235563 A1 | 12/2003 | Strom et al. |
| 2003/0235909 A1 | 12/2003 | Hariri et al. |
| 2004/0005704 A1 | 1/2004 | Csete et al. |
| 2004/0009593 A1 | 1/2004 | Keirstead et al. |
| 2004/0014206 A1 | 1/2004 | Robl et al. |
| 2004/0014210 A1 | 1/2004 | Jessell et al. |
| 2004/0014211 A1 | 1/2004 | Ogle et al. |
| 2004/0014662 A1 | 1/2004 | Lindquist et al. |
| 2004/0028660 A1 | 2/2004 | Hariri et al. |
| 2004/0029269 A1 | 2/2004 | Goldman et al. |
| 2004/0033597 A1 | 2/2004 | Toma et al. |
| 2004/0037818 A1 | 2/2004 | Brand et al. |
| 2004/0048372 A1 | 3/2004 | Hariri |
| 2004/0058412 A1 | 3/2004 | Ho et al. |
| 2004/0063202 A1 | 4/2004 | Petersen et al. |
| 2004/0072344 A1 | 4/2004 | Inoue et al. |
| 2004/0136967 A1 | 7/2004 | Weiss et al. |
| 2004/0204387 A1 | 10/2004 | McLaurin |
| 2004/0224409 A1 | 11/2004 | Pradier et al. |
| 2004/0265283 A1 | 12/2004 | Morishita |
| 2005/0019865 A1 | 1/2005 | Kihm et al. |
| 2005/0032209 A1 * | 2/2005 | Messina ................ C12N 5/0607 435/366 |
| 2005/0037491 A1 | 2/2005 | Mistry et al. |
| 2005/0054098 A1 | 3/2005 | Mistry et al. |
| 2005/0058629 A1 | 3/2005 | Harmon et al. |
| 2005/0058630 A1 | 3/2005 | Harris et al. |
| 2005/0058631 A1 | 3/2005 | Kihm et al. |
| 2005/0074435 A1 | 4/2005 | Casper et al. |
| 2005/0089513 A1 | 4/2005 | Sakuragawa et al. |
| 2005/0148074 A1 | 7/2005 | Davies et al. |
| 2005/0249731 A1 | 11/2005 | Aslan et al. |
| 2006/0094113 A1 | 5/2006 | Epstein et al. |
| 2006/0128014 A1 | 6/2006 | Haggblad et al. |
| 2006/0147415 A1 | 7/2006 | Mousa et al. |
| 2006/0153815 A1 | 7/2006 | Seyda et al. |

(56) References Cited

U.S. PATENT DOCUMENTS

| | | |
|---|---|---|
| 2006/0153816 A1 | 7/2006 | Brown et al. |
| 2006/0153817 A1 | 7/2006 | Kihm et al. |
| 2006/0153818 A1 | 7/2006 | Dhanaraj et al. |
| 2006/0154366 A1 | 7/2006 | Brown et al. |
| 2006/0154367 A1 | 7/2006 | Kihm et al. |
| 2006/0166361 A1 | 7/2006 | Seyda et al. |
| 2006/0171930 A1 | 8/2006 | Seyda et al. |
| 2006/0188983 A1 | 8/2006 | Harris et al. |
| 2006/0210544 A1 | 9/2006 | Honmou et al. |
| 2006/0223177 A1 | 10/2006 | Harris et al. |
| 2006/0233765 A1 | 10/2006 | Messina et al. |
| 2006/0233766 A1 | 10/2006 | Messina et al. |
| 2006/0234376 A1 | 10/2006 | Mistry et al. |
| 2007/0009494 A1 | 1/2007 | Mistry et al. |
| 2007/0014771 A1 | 1/2007 | Mistry et al. |
| 2007/0025973 A1 | 2/2007 | Fitzsimmons et al. |
| 2007/0036767 A1 | 2/2007 | Mistry et al. |
| 2007/0042437 A1 | 2/2007 | Wands et al. |
| 2007/0053888 A1 | 3/2007 | Harriri et al. |
| 2007/0141700 A1 | 6/2007 | Harmon |
| 2007/0160588 A1 | 7/2007 | Kihm |
| 2007/0264269 A1 | 11/2007 | Harmon et al. |
| 2007/0275362 A1 | 11/2007 | Edinger et al. |
| 2008/0057053 A1 | 3/2008 | Stolen |
| 2008/0112939 A1 | 5/2008 | Colter et al. |
| 2008/0131409 A1 | 6/2008 | Cataldo et al. |
| 2008/0145934 A1 | 6/2008 | Harris et al. |
| 2008/0166328 A1 | 7/2008 | Harmon et al. |
| 2008/0226595 A1 | 9/2008 | Edinger et al. |
| 2008/0260699 A1 | 10/2008 | Parman |
| 2008/0274087 A1 | 11/2008 | Li et al. |
| 2008/0305148 A1 | 12/2008 | Fu |
| 2009/0092653 A1 | 4/2009 | Colter et al. |
| 2009/0166178 A1 | 7/2009 | Harmon et al. |
| 2009/0169597 A1 | 7/2009 | Brown et al. |
| 2010/0158877 A1 | 6/2010 | Colter et al. |
| 2010/0158880 A1 | 6/2010 | Seyda et al. |
| 2010/0159025 A1 | 6/2010 | Kramer et al. |
| 2010/0159588 A1 | 6/2010 | Harmon et al. |
| 2010/0210013 A1 | 8/2010 | Mistry et al. |
| 2010/0215714 A1 | 8/2010 | Messina et al. |
| 2010/0260843 A1 | 10/2010 | Messina et al. |
| 2010/0272803 A1 | 10/2010 | Mistry et al. |
| 2011/0223205 A1 | 9/2011 | Gosiewska et al. |
| 2012/0315251 A1 | 12/2012 | Harris et al. |
| 2013/0022585 A1 | 1/2013 | Messina et al. |
| 2014/0045263 A1 | 2/2014 | Mistry et al. |
| 2014/0154226 A1 | 6/2014 | Messina et al. |
| 2015/0064781 A1 | 3/2015 | Mistry et al. |
| 2015/0374758 A1 | 12/2015 | Buensuceso et al. |

FOREIGN PATENT DOCUMENTS

| | | |
|---|---|---|
| WO | WO 00/09666 | 2/2000 |
| WO | WO 00/053795 A1 | 9/2000 |
| WO | WO 00/073421 | 12/2000 |
| WO | WO 01/011011 | 2/2001 |
| WO | WO 01/019379 | 3/2001 |
| WO | WO 01/034775 | 5/2001 |
| WO | WO 00/18413 | 4/2002 |
| WO | WO 02/046373 | 6/2002 |
| WO | WO 02/059278 | 8/2002 |
| WO | WO 02/062969 | 8/2002 |
| WO | WO 02/063962 | 8/2002 |
| WO | WO 02/064748 | 8/2002 |
| WO | WO 02/064755 | 8/2002 |
| WO | WO 02/086107 | 10/2002 |
| WO | WO 03/002140 | 1/2003 |
| WO | WO 03/023020 | 3/2003 |
| WO | WO 03/025149 | 3/2003 |
| WO | WO 03/029443 | 4/2003 |
| WO | WO 03/029445 | 4/2003 |
| WO | WO 03/039489 | 5/2003 |
| WO | WO 03/042405 | 5/2003 |
| WO | WO 03/048336 | 6/2003 |
| WO | WO 03/055992 | 7/2003 |
| WO | WO 03/064601 | 8/2003 |
| WO | WO 03/066832 | 8/2003 |
| WO | WO 03/068937 | 8/2003 |
| WO | WO 03/070922 | 8/2003 |
| WO | WO 03/072728 | 9/2003 |
| WO | WO 03/080822 | 10/2003 |
| WO | WO 03/087333 | 10/2003 |
| WO | WO 03/087392 | 10/2003 |
| WO | WO 03/089619 | 10/2003 |
| WO | WO 03/100038 | 12/2003 |
| WO | WO 03/102134 | 12/2003 |
| WO | WO 03/102151 | 12/2003 |
| WO | WO 03/104442 | 12/2003 |
| WO | WO 04/011012 | 2/2004 |
| WO | WO 04/011621 | 2/2004 |
| WO | WO 04/016747 | 2/2004 |
| WO | WO 04/023100 | 3/2004 |
| WO | WO 07/047468 | 4/2004 |
| WO | WO 04/072273 | 8/2004 |
| WO | WO 05/001076 | 1/2005 |
| WO | WO 05/001077 | 1/2005 |
| WO | WO 05/001078 | 1/2005 |
| WO | WO 05/001079 | 1/2005 |
| WO | WO 05/001080 | 1/2005 |
| WO | WO 05/003334 | 1/2005 |
| WO | WO 05/007176 | 1/2005 |
| WO | WO 05/021738 | 3/2005 |
| WO | WO 05/038012 | 4/2005 |
| WO | WO 05/042703 | 5/2005 |
| WO | WO 05/085421 | 9/2005 |
| WO | WO 06/055685 | 5/2006 |
| WO | WO 06/057003 | 6/2006 |
| WO | WO 06/071773 | 7/2006 |
| WO | WO 06/071777 | 7/2006 |
| WO | WO 06/071778 | 7/2006 |
| WO | WO 06/071794 | 7/2006 |
| WO | WO 06/071802 | 7/2006 |
| WO | WO 06/083394 | 8/2006 |
| WO | WO 06/105152 | 10/2006 |
| WO | WO 06/117237 | 10/2006 |
| WO | WO 07/051625 | 5/2007 |
| WO | WO 07/070870 | 6/2007 |
| WO | WO 07/073552 | 6/2007 |
| WO | WO 07/076522 | 7/2007 |
| WO | WO 07/079184 | 7/2007 |
| WO | WO 07/084957 | 7/2007 |
| WO | WO 07/089063 | 8/2007 |
| WO | WO 07/108003 | 8/2007 |
| WO | WO 07/142651 | 12/2007 |
| WO | WO 08/002250 | 1/2008 |
| WO | WO 08/045498 | 4/2008 |
| WO | WO 08/060541 | 5/2008 |
| WO | WO 08/085221 | 7/2008 |
| WO | WO 09/046335 | 4/2009 |
| WO | WO 09/085860 | 7/2009 |
| WO | WO 10/071862 | 6/2010 |
| WO | WO 10/071863 | 6/2010 |
| WO | WO 10/071864 | 6/2010 |
| WO | WO 10/080364 | 7/2010 |
| WO | WO 10/111663 A1 | 9/2010 |
| WO | WO 10/111663 | 9/2011 |
| WO | WO 12/112576 | 8/2012 |

OTHER PUBLICATIONS

Yamada et al, Stem Cells 25:562-570, 2007.*
In the U.S. Patent and Trademark Office, Final Office Action in re: U.S. Appl. No. 12/642,773 dated Aug. 6, 2014, 19 pages.
In the U.S. Patent and Trademark Office, Final Office Action in re: U.S. Appl. No. 12/389,305 dated Aug. 6, 2014, 57 pages.
In the U.S. Patent and Trademark Office, Non-Final Office Action in re: U.S. Appl. No. 11/611,602 dated Oct. 9, 2014, 15 pages.
In the U.S. Patent and Trademark Office, Final Office Action in re: U.S. Appl. No. 11/317,574 dated Feb. 3, 2014, 12 pages.
In the U.S. Patent and Trademark Office, Final Office Action in re: U.S. Appl. No. 11/321,864 dated Nov. 3, 2014, 10 pages.

(56) References Cited

OTHER PUBLICATIONS

In the U.S. Patent and Trademark Office, Final Office Action in re: U.S. Appl. No. 10/876,998 dated Dec. 16, 2014, 19 pages.
In the U.S. Patent and Trademark Office, Non-Final Office Action in re: U.S. Appl. No. 11/322,372 dated Nov. 25, 2014, 24 pages.
In the U.S. Patent and Trademark Office, Final Office Action in re: U.S. Appl. No. 11/315,969 dated Dec. 18, 2014, 30 pages.
In the U.S. Patent and Trademark Office, Final Office Action in re: U.S. Appl. No. 11/321,863 dated Jan. 31, 2014, 17 pages.
In the U.S. Patent and Trademark Office, Non-Final Office Action in re: U.S. Appl. No. 14/152,649 dated Feb. 26, 2015, 9 pages.
Ciavarella, S. et al., "Umbilical Cord Mesenchymal Stem Cells: Role of Regulatory Genes in Their Differentiation to Osteoblasts," *Stem Cells and Development*, 2009; 18:1211-1220.
Hass, R. et al., "Different populations and sources of human mesenchymal stem cells (MSC): A comparison of adult and neonatal tissue-derived MSC," *Cell Communication and Signaling*, 2011; 9:12, p. 1-14.
Ho, A.D. et al., "Heterogeneity of mesenchymal stromal cell preparations," Cytotherapy, 2008;10(4):320-30.
Pittenger, M.F. et al.; "Human mesenchymal stem cells: progenitor cells for cartilage, bone, fat and stroma," *Current Topics in Microbiology and Immunology*, 200; 251:3-11.
Rachakatla, R. S. et al., "Development of Human Umbilical Cord Matrix Stem Cell-Based Gene Therapy for Experimental Lung Tumors," *Cancer Gene Therapy*, 2007; 14:828-835.
Secco, M. et al.,"Multipotent Stem Cells from Umbilical Cord: Cord is Richer than Blood!" *Stem Cells*, 2008; 26:146-150.
Solomon, D. E., "An in vitro examination of extracellular matrix scaffold for use in wound healing," *Int. J. Path*, 2002, 93: 209-216.
Troyer, D. L. et al., "Concise Review: Wharton's Jelly-Derived Cells Are a Primitive Stromal Cell Population," *Stem Cells*, 2008; 26:591-599.
In the U.S. Patent and Trademark Office, Non-Final Office Action in re: U.S. Appl. No. 10/877,012, dated Sep. 24, 2007, 18 pages.
In the U.S. Patent and Trademark Office, Final Office Action in re: U.S. Appl. No. 10/877,012, dated Mar. 15, 2007, 13 pages.
In the U.S. Patent and Trademark Office, Non-Final Office Action in re: U.S. Appl. No. 10/877,012, dated Jul. 18, 2006, 26 pages.
In the U.S. Patent and Trademark Office, Non-Final Office Action in re: U.S. Appl. No. 11/315,897, dated Jun. 13, 2008, 12 pages.
In the U.S. Patent and Trademark Office, Non-Final Office Action in re: U.S. Appl. No. 10/877,446, dated Feb. 28, 2008, 19 pages.
In the U.S. Patent and Trademark Office, Final Office Action in re: U.S. Appl. No. 10/877,446, dated Jun. 27, 2007, 24 pages.
In the U.S. Patent and Trademark Office, Non-Final Office Action in re: U.S. Appl. No. 10/877,446, dated Nov. 20, 2006, 24 pages.
In the U.S. Patent and Trademark Office, Non-Final Office Action in re: U.S. Appl. No. 10/877,269, dated Jan. 17, 2008, 10 pages.
In the U.S. Patent and Trademark Office, Final Office Action in re: U.S. Appl. No. 10/877,269, dated Aug. 14, 2007, 6 pages.
In the U.S. Patent and Trademark Office, Non-Final Office Action in re: U.S. Appl. No. 10/877,269, dated May 3, 2007, 12 pages.
In the U.S. Patent and Trademark Office, Non-Final Office Action in re: U.S. Appl. No. 11/315,898, dated Feb. 13, 2008, 12 pages.
In the U.S. Patent and Trademark Office, Final Office Action in re: U.S. Appl. No. 11/315,943, dated Aug. 20, 2008, 7 pages.
In the U.S. Patent and Trademark Office, Non-Final Office Action in re: U.S. Appl. No. 11/315,943, dated Feb. 12, 2008, 11 pages.
In the U.S. Patent and Trademark Office, Non-Final Office Action in re: U.S. Appl. No. 10/877,445, dated Jul. 11, 2008, 12 pages.
In the U.S. Patent and Trademark Office, Non-Final Office Action in re: U.S. Appl. No. 10/877,445, dated Mar. 19, 2008, 12 pages.
In the U.S. Patent and Trademark Office, Final Office Action in re: U.S. Appl. No. 10/877,445, dated Nov. 5, 2007, 17 pages.
In the U.S. Patent and Trademark Office, Non-Final Office Action in re: U.S. Appl. No. 10/877,445, dated May 17, 2007, 20 pages.
In the U.S. Patent and Trademark Office, Final Office Action in re: U.S. Appl. No. 10/877,445, dated Sep. 11, 2006, 30 pages.
In the U.S. Patent and Trademark Office, Non-Final Office Action in re: U.S. Appl. No. 10/877,445, dated Nov. 21, 2005, 17 pages.
In the U.S. Patent and Trademark Office, Non-Final Office Action in re: U.S. Appl. No. 11/322,372 dated Sep. 3, 2008, 13 pages.
In the U.S. Patent and Trademark Office, Non-Final Office Action in re: U.S. Appl. No. 10/877,541, dated Jul. 25, 2007, 13 pages.
In the U.S. Patent and Trademark Office, Advisory Office Action in re: U.S. Appl. No. 10/877,541, dated Apr. 18, 2007, 4 pages
In the U.S. Patent and Trademark Office, Final Office Action in re: U.S. Appl. No. 10/877,541, dated Jan. 10, 2007, 19 pages.
In the U.S. Patent and Trademark Office, Non-Final Office Action in re: U.S. Appl. No. 10/877,541, dated Feb. 22, 2006, 13 pages.
In the U.S. Patent and Trademark Office, Advisory Office Action in re: U.S. Appl. No. 11/317,574, dated Jun. 4, 2008, 3 pages.
In the U.S. Patent and Trademark Office, Final Office Action in re: U.S. Appl. No. 11/317,574, dated Mar. 5, 2008, 10 pages.
In the U.S. Patent and Trademark Office, Final Office Action in re: U.S. Appl. No. 11/317,574, dated Aug. 10, 2007, 14 pages.
In the U.S. Patent and Trademark Office, Non-Final Office Action in re: U.S. Appl. No. 10/877,009 dated Jan. 9, 2008, 12 pages.
In the U.S. Patent and Trademark Office, Final Office Action in re: U.S. Appl. No. 10/877,009, dated Jul. 25, 2007, 17 pages.
In the U.S. Patent and Trademark Office, Final Office Action in re: U.S. Appl. No. 10/877,009, dated Nov. 21, 2006, 15 pages.
In the U.S. Patent and Trademark Office, Non-Final Office Action in re: U.S. Appl. No. 10/876,998, dated Jun. 25, 2008, 9 pages.
In the U.S. Patent and Trademark Office, Final Office Action in re: U.S. Appl. No. 10/876,998, dated Feb. 27, 2008, 18 pages.
In the U.S. Patent and Trademark Office, Non-Final Office Action in re: U.S. Appl. No. 10/876,998, dated Jul. 13, 2007, 30 pages.
In the U.S. Patent and Trademark Office, Final Office Action in re: U.S. Appl. No. 10/876,998, dated Oct. 18, 2006, 29 pages.
In the U.S. Patent and Trademark Office, Non-Final Office Action in re: U.S. Appl. No. 10/876,998, dated Mar. 30, 2006, 24 pages.
In the U.S. Patent and Trademark Office, Non-Final Office Action in re: U.S. Appl. No. 11/321,863, dated Aug. 19, 2008, 15 pages.
In the U.S. Patent and Trademark Office, Non-Final Office Action in re: U.S. Appl. No. 11/322,003, dated Jun. 2, 2008, 14 pages.
In the U.S. Patent and Trademark Office, Non-Final Office Action in re: U.S. Appl. No. 11/321,864, dated Apr. 21, 2008, 7 pages.
In the U.S. Patent and Trademark Office, Final Office Action in re: U.S. Appl. No. 11/315,969, dated May 19, 2008, 9 pages.
In the U.S. Patent and Trademark Office, Non-Final Office Action in re: U.S. Appl. No. 11/315,969, dated Nov. 1, 2007, 12 pages.
In the U.S. Patent and Trademark Office, Final Office Action in re: U.S. Appl. No. 11/297,778, dated Apr. 11, 2008, 9 pages.
In the U.S. Patent and Trademark Office, Non-Final Office Action in re: U.S. Appl. No. 11/297,778, dated Feb. 22, 2007, 8 pages.
In the U.S. Patent and Trademark Office, Final Office Action in re: U.S. Appl. No. 11/304,091, dated Apr. 11, 2008, 11 pages.
In the U.S. Patent and Trademark Office, Non-Final Office Action in re: U.S. Appl. No. 11/304,091, dated Feb. 23, 2007, 9 pages.
In the U.S. Patent and Trademark Office, Final Office Action in re: U.S. Appl. No. 11/315,898, dated Sep. 16, 2008, 8 pages.
In the U.S. Patent and Trademark Office, Non-Final Office Action, in re: U.S. Appl. No. 11/297,156, dated Oct. 10, 2008, 11 pages.
In the U.S. Patent and Trademark Office, Non-Final Office Action in re: U.S. Appl. No. 11/317,574, dated Sep. 30, 2008, 23 pages.
In the U.S. Patent and Trademark Office, Non-Final Office Action in re: U.S. Appl. No. 11/315,969, dated Dec. 23, 2008, 11 pages.
In the U. S. Patent and Trademark Office, Non-Final Office Action in re: U.S. Appl. No. 10/951,357, dated Nov. 26, 2008, 19 pages.
In the U.S. Patent and Trademark Office, Non-Final Office Action in re: U.S. Appl. No. 11/321,864, dated Jan. 8, 2009, 10 pages.
In the U. S. Patent and Trademark Office, Final Office Action in re: U.S. Appl. No. 11/321,863, dated Feb. 12, 2009, 15 pages.
In the U.S. Patent and Trademark Office, Non-Final Office Action in re: U.S. Appl. No. 11/315,943, dated Feb. 20, 2009, 9 pages.
In the U.S. Patent and Trademark Office, Non-Final Office Action in re: U.S. Appl. No. 10/877,445, dated Mar. 19, 2009, 15 pages.
In the U. S. Patent and Trademark Office, Non-Final Office Action in re: U.S. Appl. No. 11/481,481, dated Mar. 20, 2009, 12 pages.

(56) References Cited

OTHER PUBLICATIONS

In the U.S. Patent and Trademark Office, Final Office Action in re: U.S. Appl. No. 11/315,897, dated Mar. 20, 2009, 13 pages.
In the U.S. Patent and Trademark Office, Non-Final Office Action in re: U.S. Appl. No. 11/481,480, dated Mar. 20, 2009, 13 pages.
In the U.S. Patent and Trademark Office, Final Office Action in re: U.S. Appl. No. 11/322,003 dated Feb. 13, 2009, 17 pages.
In the U.S. Patent and Trademark Office, Final Office Action in re: U.S. Appl. No. 10/876,998 dated Feb. 13, 2009, 10 pages.
In the U.S. Patent and Trademark Office, Final Office Action in re: U.S. Appl. No. 11/322,372 dated Feb. 13, 2009, 14 pages.
In the U.S. Patent and Trademark Office, Non-Final Office Action in re: U.S. Appl. No. 11/315,898 dated Feb. 18, 2009, 10 pages.
In the U.S. Patent and Trademark Office, Non-Final Office Action in re: U.S. Appl. No. 11/304,091 dated Feb. 27, 2009, 11 pages.
In the U.S. Patent and Trademark Office, Non-Final Office Action in re: U.S. Appl. No. 11/481,456 dated Apr. 16, 2009, 14 pages.
In the U.S. Patent and Trademark Office, Non-Final Office Action in re: U.S. Appl. No. 11/317,574 dated Apr. 29, 2009, 21 pages.
In the U. S. Patent and Trademark Office, Advisory Action in re: U.S. Appl. No. 11/315,969 dated Sep. 29, 2009, 8 pages.
In the U. S. Patent and Trademark Office, Advisory Action in re: U.S. Appl. No. 11/322,372 dated May 12, 2009, 10 pages.
In the U.S. Patent and Trademark Office, Non-Final Office Action in re: U.S. Appl. No. 10/877,446 dated Jun. 12, 2009, 16 pages.
In the U. S. Patent and Trademark Office, Final Office Action in re: U.S. Appl. No. 11/322,372 dated Aug. 6, 2009, 12 pages.
In the U. S. Patent and Trademark Office, Final Office Action in re: U.S. Appl. No. 11/617,346 dated Aug. 11, 2009,12 pages.
In the U. S. Patent and Trademark Office, Final Office Action in re: U.S. Appl. No. 11/481,456 dated Oct. 9, 2009, 11 pages.
In the U. S. Patent and Trademark Office, Final Office Action in re: U.S. Appl. No. 10/877,445 dated Aug. 25, 2009, 18 pages.
In the U. S. Patent and Trademark Office, Final Office Action in re: U.S. Appl. No. 11/321,863 dated Aug. 7, 2009, 11 pages.
In the U. S. Patent and Trademark Office, Final Office Action in re: U.S. Appl. No. 11/321,864 dated Aug. 17, 2009, 13 pages.
In the U. S. Patent and Trademark Office, Final Office Action in re: U.S. Appl. No. 11/315,969 dated May 13, 2009, 11 pages.
In the U. S. Patent and Trademark Office, Non-Final Office Action in re: U.S. Appl. No. 11/317,574 dated Dec. 28, 2009, 26 pages.
In the U. S. Patent and Trademark Office, Non-Final Office Action in re: U.S. Appl. No. 11/321,863 dated Jan. 7, 2010, 13 pages.
In the U. S. Patent and Trademark Office, Non-Final Office Action in re: U.S. Appl. No. 11/321,864 dated Jan. 27, 2010, 12 pages.
In the U. S. Patent and Trademark Office, Non-Final Office Action in re: U.S. Appl. No. 11/315,969 dated Jan. 27, 2010, 12 pages.
In the U. S. Patent and Trademark Office, Non-Final Office Action in re: U.S. Appl. No. 11/315,943 dated Feb. 19, 2010, 13 pages.
In the U. S. Patent and Trademark Office, Final Office Action in re: U.S. Appl. No. 11/316,104 dated Mar. 24, 2010, 12 pages.
In the U. S. Patent and Trademark Office, Non-Final Office Action in re: U.S. Appl. No. 11/481,456 dated May 14, 2010, 9 pages.
In the U. S. Patent and Trademark Office, Non-Final Office Action in re: U.S. Appl. No. 11/481,481 dated May 13, 2010, 9 pages.
In the U. S. Patent and Trademark Office, Final Office Action in re: U.S. Appl. No. 11/315,897 dated May 14, 2010, 13 pages.
In the U. S. Patent and Trademark Office, Non-Final Office Action in re: U.S. Appl. No. 11/481,480 dated May 17, 2010, 10 pages.
In the U. S. Patent and Trademark Office, Final Office Action in re: U.S. Appl. No. 10/877,445 dated Jul. 8, 2010, 20 pages.
In the U. S. Patent and Trademark Office, Final Office Action in re: U.S. Appl. No. 10/876,998 dated Aug. 3, 2010, 14 pages.
In the U. S. Patent and Trademark Office, Non-Final Office Action in re: U.S. Appl. No. 11/321,863 dated Aug. 17, 2010, 15 pages.
In the U. S. Patent and Trademark Office, Final Office Action in re: U.S. Appl. No. 11/617,346 dated Aug. 20, 2010, 12 pages.
In the U. S. Patent and Trademark Office, Final Office Action in re: U.S. Appl. No. 11/321,864 dated Aug. 31, 2010, 7 pages.
In the U. S. Patent and Trademark Office, Final Office Action in re: U.S. Appl. No. 11/315,969 dated Aug. 31, 2010, 6 pages.
In the U. S. Patent and Trademark Office, Final Office Action in re: U.S. Appl. No. 11/322,372 dated Aug. 31, 2010, 11 pages.
In the U. S. Patent and Trademark Office, Non-Final Office Action in re: U.S. Appl. No. 12/245,571 dated Sep. 15, 2010, 8 pages.
In the U. S. Patent and Trademark Office, Non-Final Office Action in re: U.S. Appl. No. 11/316,104 dated Sep. 21, 2010, 13 pages.
In the U. S. Patent and Trademark Office, Final Office Action in re: U.S. Appl. No. 11/317,574 dated Oct. 6, 2010, 16 pages.
In the U. S. Patent and Trademark Office, Non-Final Office Action in re: U.S. Appl. No. 12/054,718 dated Sep. 29, 2010, 18 pages.
In the U. S. Patent and Trademark Office, Non-Final Office Action in re: U.S. Appl. No. 11/322,372 dated Jan. 21, 2010, 10 pages.
In the U. S. Patent and Trademark Office, Final Office Action in re: U.S. Appl. No. 11/481,481 dated Sep. 18, 2009, 11 pages.
In the U. S. Patent and Trademark Office, Advisory Action in re: U.S. Appl. No. 11/315,897 dated Jun. 30, 2009, 3 pages.
In the U. S. Patent and Trademark Office, Non-Final Action in re: U.S. Appl. No. 11/315,897 dated Sep. 2, 2009, 12 pages.
In the U. S. Patent and Trademark Office, Final Action in re: U.S. Appl. No. 11/481,480 dated Sep. 17, 2009, 12 pages.
In the U. S. Patent and Trademark Office, Final Action in re: U.S. Appl. No. 10/877,446 dated Jun. 4, 2010, 17 pages.
In the U. S. Patent and Trademark Office, Final Action in re: U.S. Appl. No. 11/617,346 dated Apr. 15, 2010, 7 pages.
In the U. S. Patent and Trademark Office, Non-Final Action in re: U.S. Appl. No. 11/316,104 dated Oct. 31, 2008, 15 pages.
In the U. S. Patent and Trademark Office, Final Action in re: U.S. Appl. No. 10/876,998 dated May 27, 2009, 14 pages.
In the U. S. Patent and Trademark Office, Non-Final Action in re: U.S. Appl. No. 10/876,998 dated Nov. 24, 2009, 7 pages.
In the U. S. Patent and Trademark Office, Final Action in re: U.S. Appl. No. 11/322,003 dated Feb. 13, 2009, 17 pages.
In the U. S. Patent and Trademark Office, Non-Final Office Action in re: U.S. Appl. No. 12/337,439 dated Jan. 6, 2011, 11 pages.
In the U. S. Patent and Trademark Office, Non-Final Office Action in re: U.S. Appl. No. 10/876,998 dated Feb. 1, 2011, 11 pages.
In the U. S. Patent and Trademark Office, Non-Final Office Action in re: U.S. Appl. No. 11/481,456 dated Feb. 3, 2011, 10 pages.
In the U. S. Patent and Trademark Office, Non-Final Office Action in re: U.S. Appl. No. 11/481,481 dated Feb. 3, 2011, 10 pages.
In the U. S. Patent and Trademark Office, Non-Final Office Action in re: U.S. Appl. No. 12/389,305 dated Feb. 8, 2011, 14 pages.
In the U. S. Patent and Trademark Office, Non-Final Office Action in re: U.S. Appl. No. 11/481,480 dated Feb. 3, 2011, 10 pages.
In the U. S. Patent and Trademark Office, Final Office Action in re: U.S. Appl. No. 10/877,446 dated Nov. 2, 2011, 12 pages.
In the U. S. Patent and Trademark Office, Final Office Action in re: U.S. Appl. No. 12/389,305 dated Oct. 12, 2011, 12 pages.
In the U. S. Patent and Trademark Office, Final Office Action in re: U.S. Appl. No. 12/429,849 dated Mar. 20, 2012, 9 pages
In the U. S. Patent and Trademark Office, Non-Final Office Action in re: U.S. Appl. No. 12/642,773 dated Mar. 29, 2012, 28 pages.
In the U. S. Patent and Trademark Office, Final Office Action in re: U.S. Appl. No. 11/481,456 dated Oct. 11, 2011, 6 pages.
In the U. S. Patent and Trademark Office, Non-Final Office Action in re: U.S. Appl. No. 12/697,081 dated Apr. 2, 2012, 8 pages.
In the U. S. Patent and Trademark Office, Final Office Action in re: U.S. Appl. No. 12/642,773 dated Sep. 13, 2012, 21 pages.
In the U. S. Patent and Trademark Office, Non-Final Office Action in re: U.S. Appl. No. 12/642,775 dated Nov. 21, 2012, 16 pages.
In the U. S. Patent and Trademark Office, Non-Final Office Action in re: U.S. Appl. No. 13/605,716 dated Feb. 13, 2013, 13 pages.
In the U. S. Patent and Trademark Office, Final Office Action in re: U.S. Appl. No. 12/642,775 dated Jun. 21, 2013, 17 pages.
In the U. S. Patent and Trademark Office, Non-Final Office Action in re: U.S. Appl. No. 11/317,574 dated Jul. 11, 2013, 29 pages.
In the U. S. Patent and Trademark Office, Non-Final Office Action in re: U.S. Appl. No. 12/642,773 dated Nov. 14, 2013, 28 pages.
In the U. S. Patent and Trademark Office, Non-Final Office Action in re: U.S. Appl. No. 11/322,372 dated Jan. 16, 2014, 17 pages.

(56) References Cited

OTHER PUBLICATIONS

In the U. S. Patent and Trademark Office, Non-Final Office Action in re: U.S. Appl. No. 11/321,864 dated Jan. 29, 2014, 9 pages.
In the U. S. Patent and Trademark Office, Non-Final Office Action in re: U.S. Appl. No. 11/321,863 dated Jan. 31, 2014, 17 pages.
In the U. S. Patent and Trademark Office, Final Office Action in re: U.S. Appl. No. 11/317,574 dated Feb. 3, 2014, 16 pages.
In the U. S. Patent and Trademark Office, Non-Final Office Action in re: U.S. Appl. No. 10/876,998 dated Feb. 11, 2014, 14 pages.
In the U. S. Patent and Trademark Office, Non-Final Office Action in re: U.S. Appl. No. 12/389,305 dated Mar. 6, 2014, 37 pages.
In the U. S. Patent and Trademark Office, Non-Final Office Action in re: U.S. Appl. No. 11/316,104 dated Mar. 14, 2014, 11 pages.
In the U. S. Patent and Trademark Office, Non-Final Office Action in re: U.S. Appl. No. 12/642,775 dated Mar. 18, 2014, 33 pages.
In the U. S. Patent and Trademark Office, Non-Final Office Action in re: U.S. Appl. No. 12/389,305 dated Mar. 21, 2014, 47 pages.
In the U. S. Patent and Trademark Office, Non-Final Office Action in re: U.S. Appl. No. 10/877,446 dated Mar. 21, 2014, 21 pages.
In the U. S. Patent and Trademark Office, Non-Final Office Action in re: U.S. Appl. No. 11/316,104 dated Mar. 21, 2014, 20 pages.
In the U. S. Patent and Trademark Office, Non-Final Office Action in re: U.S. Appl. No. 11/315,969 dated Mar. 21, 2014, 15 pages.
"Cell Lysis, p. 2" http://www.piercenet.com/objects/view.cfm?type=Page&ID=1904ED25-8FA4-475C-8068-C2E813D5F4E7; accessed Aug. 7, 2008.
Abbas, A.K. et al., *Cellular and Molecular Immunology*, 5th Ed. (2003) Saunders, Philadelphia, p. 171.
Aboody, K.S. et al., "Neural Stem Cells Display Extensive Tropism for Pathology in Adult Brain: Evidence From Intracranial Gliomase," *PNAS*, 2000; 97(23):12846-12851.
Agbulut, O. et al., "Comparison of Human Skeletal Myoblasts and Bone Marrow-Derived CD133+ Progenitors for the Repair of Infarcted Myocardium," *Journal of the American College of Cardiology*, 2004; 44(2):458-463.
Age-Related Eye Disease Study Research Group, "A Randomized, Placebo-Controlled, Clinical Trial of High-Dose Supplementation With Vitamins C and E, Beta Carotene, and Zinc for Age-Related Macular Degeneration and Vision Loss," AREDS Report No. 8, *Arch. Op.*
Aggarwal et al., "Human Mesenchymal Stem Cells Modulate Allogeneic Immune Cell Responses," *Blood*, 2005; 105(4):1815-1822.
Aldskogius, H. et al., "Strategies for Repair of the Deafferented Spinal Cord," *Brain Res. Rev.*, 2002; 40:301-308.
Alini, M. et al., "A Biological Approach to Treating Disc Degeneration: Not for Today, But Maybe for Tomorrow," Eur. Spine J., 2002; 11 (Supp. 2 ): S215-220.
Allcock, H.R. et al., "Synthesis of Poly[(Amino Acid Alkyl Ester)Phosphazenes]1-3," *Macromolecules*, 1977; 10(4):824-830.
Altman, G.H. et al., "Advanced Bioreactor With Controlled Application of Multi-Dimensional Strain for Tissue Engineering," *J. Biomech. Eng.*, 2002; 124:742-749.
Altman, R.D. et al., "Radiographic Assessment of Progression in Osteoarthritis," *Arthritis & Rheum.*, 1987; 30(11):1214-1225.
Anseth, K.S. et al., "In Situ Forming Degradable Networks and Their Application in Tissue Engineering and Drug Delivery," *J. of Controlled Release*, 2002; 78:199-209.
Armulik, A. et al.,"Endothelial/Pericyte Interactions," *Circ. Res.*, 2005; 97:512-523.
Aston, J. E., et al., "Repair of Articular Surfaces by Allografts of Articular and Growth-Plate Cartilage," *Journal of Bone and Joint Surgery*, 1986; 68-B(1 ):29-35.
Auda-Boucher, G. et al., "Staging of the Commitment of Murine Cardiac Cell Progenitors," *Dev. Bio.*, 2000; 225(1):214-225.
Avital, I. et al., "Isolation, Characterization, and Transplantation of Bone Marrow-Derived Hepatocyte Stem Cells," *Biochem. & Biophys. Res. Comm.*, 2001; 288:156-164.

Azizi, S.A. et al., "Engraftment and Migration of Human Bone Marrow Stromal Cells Implanted in the Brains of Albino Rats—Similarities to Astrocyte Grafts," *Proc. Natl. Acad. Sci. USA*, 1998; 95:3908-3913.
Bai, M., et al, "Dimerization of the Extracellular Calcium-sensing Receptor (CaR) on the Cell Surface of CaR Transfected HEK293 Cells," *J. Biol Chem.*, 1998; 273(36): 23605-23610.
Baker, K.A. etal., "Intrastriatal and Intranigral Grafting of hNT Neurons in the 6-OHDA Rat Model of Parkinson's Disease," *Exper. Neurol.*, 2000; 162:350-360.
Baksh, D. et al., "Comparison of proliferative and multilineage differentiation potential of human mesenchymal stem cells derived from umbilical cord and bone marrow." Stem Cells, 2007; 25: 1384-1392.
Bakhshi, et al. "Mesenchymal stem cells from the Wharton's jelly of umbilical cord segments provide stromal support for the maintenance of cord blood hematopoietic stem cells during long-term ex vivo culture", Transfusion, 2008; 48: 2638-2644.
Balis, F. et al., "Central Nervous System Pharmacology of Antileukemic Drugs," *Am. J. of Pediatric Hematol. Oncol.*, 1989; 11(1):74-86.
Balkema, G.W. et al., "Impaired Visual Thresholds in Hypopigmented Animals," *Visual Neuroscience*, 1991; 6:577-585.
Bao, Z.Z. et al., "Regulation of Chamber-Specific Gene Expression in the Developing Heart by IrX 4," *Science*, 1999; 283(5405):1161-1164 (Abstract 1 page).
Barberi, T. et al., "Neural Subtype Specification of Fertilization and Nuclear Transfer Embryonic Stem Cells and Application in Parkinsonian Mice," *Nature Biotechnology*, 2003; 21(10):1200-1207.
Basso, DM et al., "A sensitive and reliable bcomotor rating scale for open field testing in rats," *J Neurotrauma*, 1995; 12(1):1-21.
Basso, DM et al., "Graded histological and locomotor outcomes after spinal cord confusion using the NYU weight-drop device versus transection," *Exp. Neural.*, 1996; 139:244-256.
Beck, R.W. et al., "A Clinical Comparison of Visual Field Testing With a New Automated Perimeter, The Humphrey Field Analyzer, and the Goldmann Perimeter," *Ophthalmology*, 1985; 92(1):77-82.
Beeres, S.L. et al., "Sustained effect of autologous bone marrow mononuclear cell injection in patients with refractory angina pectoris and chronic myocardial ischemia: twelve-month follow-up results," *Am Heart J.*, 2006; 152:684.e11-6.
Bennett et al., "A Peripheral Mononeuropathy in Rate that Produces Disorders of Pain Sensation Like Those Seen in Man," Pain, 1988; 33:87-107.
Bergers, G. et al., "The Role of Pericytes in Blood-Vessel Formation and Maintenance," *Neuro-Oncology*, 2005; 7:452-464.
Bhatia, R. et al., "A clinically suitable ex vivo expansbn culture system for LTC-IC and CFC using stroma-conditioned medium," Exp Hematol., 1997;25(9):980-91 (Abstract only).
Bhindi, R. et al., "Rat Models of Mycardial Infarction," *Thromb Haemost*, 2006; 96:602-610.
Björklund, L.M. et al., "Embryonic Stem Cells Develop Into Functional Dopaminergic Neurons After Transplantation in a Parkinson Rat Model," *PNAS*, 2002; 99(4):2344-2349.
Blakemore et al., "Modelling Large Areas of Demyelination in the Rat Reveals the Potential and Possible Limitations of Transplanted Glial Cells for Remyelination in the CNS," *GLIA*, 2002; 38:155-168.
Borlongan, C.V. et al., "Upregulation of Cns trophic factors by human umbilical cord transplant is essential for neuroprotection against acute stroke," *Society for Neuroscience Abstract*, 2003, Presentation No. 789.17.
Bradley, B.A., "The Role of HLA Matching in Transplantation," *Immunol. Lett.*, 1991; 29:55-59.
Brodsky, S.V., "Coagulation, Fibrinolysis and Angiogenesis: New Insights From Knockout Mice," *Exp. Nephrol.*, 2002; 10:299-306.
Brooks, P., "Inflammation As an Important Feature of Osteoarthritis," *Bull. World Health Org.*, 2003; 81(9):689-690.
Brown, J.A. et al., "Blockade of Programmed Death-1 Ligands on Dendritic Cells Enhances T Cell Activation and Cytokine Production," *J. Immunology*, 2003; 170:1257-1266.
Bruder et al., "Mesenchymal Stem Cell Surface Antigen SB-10 Corresponds to Activated Leukocyte Cell Adhesion Molecule and Is

(56) References Cited

OTHER PUBLICATIONS

Involved in Osteogenic Differentiation," *Journal of Bone and Mineral Research*, 1998; 13(4):655-663.
Bunge et al., "The Role of the Schwann Cell in Trophic Support and Regeneration," Journal of Neurology, 1994; 241:536.
Burnstein, R.M. et al., "Differentiation and Migration of Long Term Expanded Human Neural Progenitors in a Partial Lesion Model of Parkinson's Disease," *Intern. J. of Biochem. & Cell Biology*, 2004; 36:702-713.
Bussolati et al., "Isolation of Renal Progenitor Cells from Adult Human Kidney," *American Journal of Pathology*, 2005; 166(2):545-555.
Caballero, S. et al., "The Many Possible Roles of Stem Cells in Age-Related Macular Degeneration," *Graefe's Arch. Clin. Exp. Ophthalmol.*, 2004; 242:85-90.
Cai, J. et al., "Stem cell and precursor cell therapy," *NeuroMolecular Medicine*, 2002; 3:233-249.
Campbell, I.K. et al., "Human Articular Cartilage and Chondrocytes Produce Hemopoietic Colony-Stimulating Factors in Culture in Response to IL-1," *J. of Immun.*, 1991; 147(4):1238-1246.
Can et al., "Concise Review: Human Umbilical Cord Stroma with Regard to the Source of Fetus-Derived Stem Cells," Stem Cells, 2007; 25:2886-2895.
Cao, Q. et al., "Stem Cell Repair of Central Nervous System Injury," *J. of Neuroscience Res.*, 2002; 68:501-510.
Caplan, A.I. et al., "Mesenchymal Stem Cells: Building Blocks for Molecular Medicine in the 21st Century," *Trends in Molecular Med.*, 2001; 7(6):259-264.
Carter, D. et al., "Characterization of Msc Potential to Treat GVHD Using Molecular Markers Linked to MSC-Mediated Immunosuppression In Vitro," *Blood*, 2005; 106(11) part 2, Abstract No. 4322, 160B.
Chagraoui, J. et al., "Fetal Liver Stroma Consists of Cells in Epithelial-To-Mesenchymal Transition," *Blood*, 2003; 101(8)2973-2982.
Chen, D. et al. "Differential Roles for Bone Morphogenic Protein (BMP) Receptor Type IB and IA in Differentiation and Specification of Mesenchymal Precursor Cells to Osteoblast and Adipocyte Lineages," *J. Cell Biol.*, 1998; 142(1):295-305.
Chen, H. et al., "The Effect of Hypothermia on Transient Middle Cerebral Artery Occlusion in the Rat," *J. Cereb. Blood Flow Metab.*, 1992; 12(4):621-628.
Chen, J. et al., "Intravenous Administration of Human Umbilical cord Blood Reduces Behavioral Deficits After Stroke in Rats," *Stroke*, 2001; 32:2682-2688.
Chen, J. et al., "Therapeutic Benefit of Intravenous Administration of Bone Marrow Stromal Cells after Cerebral Ischemia in Rats," *Stroke*, 2001; 32(4)1005-1011.
Chen, St. et al., "A model of focal ischemic stroke in the rat: reproducible extensive cortical infarction," *Stroke*, 1986; 17:738-743.
Cheng, A. et al., "Nitric Oxide Acts in a Positive Feedback Loop With BDNF to Regulate Neural Progenitor Cell Proliferation and Differentiation in the Mammalian Brain," *Dev. Biol.*, 2003; 258:319-333.
Chujo, T. et al.,"Effects of Growth Differentiation Factor-5 on the Intervertebral Disc-In Vitro Bovine Study and In Vivo Rabbit Disc Degeneration Model Study," *Spine*, 2006; 31: 2909-2917.
Constantini, S. et al., "The Effects of Methylprednisolone and the Ganglioside GM1 on Acute Spinal Cord Injury in Rats," *J. Neurosurg.*, 1994; 80(1):97-111.
Coumans, B. et al., "Lymphoid Cell Apoptosis Induced by Trophoblastic Cells: A Model of Active Foeto-Placental Tolerance," *J. of Immunological Methods*, 1999; 224:185-196.
Covas, D.T. et al.,"Isolation and culture of umbilical vein mesenchymal stem cells." Brazilian Journal of Medical and Biological Research, 2003; 36: 1179-1183.
D'Cruz, P.M. et al., "Mutation of the Receptor Tyrosine Kinase Gene Mertk in the Retinal Dystrophic RCS Rat," *Hum. Mol. Genet.*, 2000; 9(4):645-651.

Daley, G.Q. et al., "Realistic Prospects for Stem Cell Therapeutics," *Hematol.*, 2003; 398-418.
Danon, D. et al., "Macrophage Treatment of Pressure Sores in Paraplegia," *J. Wound Care*, 1998; 7(6):281-283.
Danon, D. et al., "Treatment of Human Ulcers by Application of Macrophages Prepared From a Blood Unit," *Exp. Gerontol.*, 1997; 32(6):633-641.
Dawson, T.M. et al., "Neuroprotective and Neurorestorative Strategies for Parkinson's Disease," *Nat. Neurosci.*, 2002; 5 Suppl. :1058-1061.
Deans, R.J. et al., "Mesenchymal stem cells: Biology and potential clinical uses," Experimental Hematobgy, 2000; 28: 875-884.
del Monte, F. et al., "Improvement in Survival and Cardiac Metabolism After Gene Transfer of Sarcoplasmic Reticulum $Ca^{2+}$-ATPase in a Rat Model of Heart Failure," *Circulation*, 2001;104:1424-1429.
Diao et al, "Human Umbilical Cord Mesenchymal Stem Cells: Osteogenesis in Vivo as Seed Cells for Bone Tissue Engineering," *J. BioMed Mater Res.*, 2009; 91A:123-131.
Dickinson, A.M. et al., "Non-HLA Immunogenetics in Hematopoietic Stem Cell Transplantation," *Curr. Opin. Immunol.*, 2005; 17(5):517-525.
Dimri, G.P. et al., "A Biomarker That Identifies Senescent Human Cells in Culture and in Aging Skin In Vivo," *Proc. Natl. Acad. Sci. USA*, 1995; 92:9363-9367.
Domb, A. et al.,"Degradable Polymers for Site-Specific Drug Delivery," *Polymers for Advanced Technologies*, 1992; 3:279-292.
Doshi, S.N. et al., "Evolving Role of Tissue Factor and Its Pathway Inhibitor," *Critical Care Med.*, 2002; 30(5):S241-S250.
Doyle, J., "Spiraling Complexity, Robustness, and Fragility in Biology," http://www.cds.caltech.edu/~doyle/CmplxNets/Bio1.pdf, available online Feb. 28, 2004.
Draper et al., "Surface Antigens of Human Embryonic Stem Cells: Changes Upon Differentiation in Culture," J. Anat., 2002; 200:249-258.
Du, Y. et al., "Functional Reconstruction of Rabbit Corneal Epithelium by Human Limbal Cells Cultured on Amniotic Membrane," *Molecular Vision*, 2003; 9:635-643.
Dutton, R, et al., "Precursor Cells in the Subventricular Zone of the Adult Mouse Are Actively Inhibited from Differentiating into Neurons," *Dev Neurosci*, 2000; 22:96-105.
Dykens, J. et al., "Photoreceptor Preservation h the S334ter Model of Retinitis Pigmentosa by a Novel Estradiol Analog", *Biochemical Pharmacology*, 2004; 68: 1971-1984.
Eagle, H., "The Specific Amino Acid Requirements of a Mammalian Cell (Strain L) in Tissue Culture," *J. Biol. Chem.*, 1955; 214:839-852.
Eblenkamp, M. et al.,"Umbilical Cord Stromal Cells (UCSC). Cells Featuring Osteogenic Differentiation Potential," *Der Orthopade*, Dec. 2004; 33:1338-1345 (English abstract on p. 1339).
Edelstein, M. L. et al., "Gene Therapy Clinical Trials Worldwide 1989-2004—An Overview," *J. Gene Med.*, 2004; 6(6):597-602.
Edlund, H., "Pancreatic Organogenesis—Developmental Mechanisms and Implications for Therapy," *Nat. Rev. Genet.*, 2002; 3:524-532.
Efrat, S. et al., "Cell Replacement Therapy for Type 1 Diabetes," *Trends in Molecular Medicine*, 2002; 8(7):334-339.
Ehtesham, M. et al., "Induction of Glioblastoma Apoptosis Using Neural Stem Cell-Mediated Delivery of Tumor Necrosis Factor-Related Apoptosis-Inducing Ligand," *Cancer Res.*, 2002; 62:7170-7174.
Ehtesham, M. et al., "The Use of Interleukin 12-Secreting Neural Stem Cells for the Treatment of Intracranial Glioma," *Cancer Res.*, 2002; 5657-5663.
Eisenhofer, G.E. et al., "Tyrosinase: A Developmentally Specific Major Determinant of Peripheral Dopamine," *FASEB J.*, 2003; 17:1248-1255.
Ende, N. et al., "Parkinson's Disease Mice and Human Umbilical Cord Blood," *J. Med.*, 2002; 33(1-4):173-180.
Engstad, C.S. et al., "The Effect of Soluble β -1,3-Glucan and Lipopolysaccharide on Cytokine Production and Coagulation Activation in Whole Blood," *Int. Immunophannacol.*, 2002; 2:1585-1597.

(56) References Cited

OTHER PUBLICATIONS

Enzmann, V. et al., "Enhanced Induction of Rpe Lineage Markers in Pluripotent Neural Stem Cells Engrafted Into the Adult Rat Subretinal Space," *Investig. Ophthalmol. Visual Sci.*, 2003; 44:5417-5422.
Erices et al., "Mesenchymal Progenitor Cells in Human Umbilical Cord Blood," *Br. J. Haematol.*, 2000; 109:235-242.
Evers, B.M., et al., "Stem Cells in Clinical Practice," *J Am Coll Surg.* 2003; 197(3):458-478.
Fazleabas, A.T. et al., "Endometrial Function: Cell Specific Changes in the Uterine Environment," *Mol. & Cellular. Endo.*, 2002; 186:143-147.
Fernandes, A.M. et al.,"Mouse Embryonic Stem Cell Expansion in a Microcarrier-based Stirred Culture System," *Journal of Biotechnology*, 2007; 132:227-236.
Fiegel, H.C. et al., "Liver-Specific Gene Expression in Cultured Human Hematopoietic Stem Cells," *Stem Cells*, 2003; 21:98-104.
Fields, G.B., "Induction of Protein-Like Molecular Architecture by Self-Assembly Processes," *Bioorg. Med. Chem.*, 1999; 7:75-81.
Fischer, D. et al., "Counteracting the Nogo Receptor Enhances Optic Nerve Regeneration If Retinal Ganglion Cells Are in an Active Growth State," *J. Neurosci.*, 2004; 24:1646-1651.
Fischer, D. et al.,"Lens-Injury-Stimulated Axonal Regeneration Throughout the Optic Pathway of Adult Rats," *Exp. Neural.*, 2001; 172:257-272.
Foley, A. et al., "Heart Induction: Embryology to Cardiomyocyte Regeneration," *Trends Cardiovasc. Med.*, 2004; 14(3):121-125.
Franc, S. et al., "Microfibrillar Composition of Umbilical Cord Matrix : Characterization of Fibrillin, Collagen VI and Intact Collagen V," *Placenta*, 1988; 19:95-104.
Freed, C.R. et al., "Transplantation of Embryonic Dopamine Neurons for Severe Parkinson's Disease," *N. Engl. J. Med.*, 2001; 344(10):710-719.
Frenkel, O. et al., "Activated Macrophages for Treating Skin Ulceration: Gene Expression in Human Monocytes After Hypo-Osmotic Shock," *Clin. Exp. Immunol.*, 2002; 128:59-66.
Friedman, J.A. et al., "Biodegradable Polymer Grafts for Surgical Repair of the Injured Spinal Cord," *Neurosurgery*, 2002; 51(3):742-751.
Fukuchi, Y. et al.,"Human Placenta-Derived Cells Have Mesenchymal Stem/Progenitor Cell Potential," *Stem Cells*, 2004; 22:649-658.
Fukuda, K., "Reprogramming of Bone Marrow Mesenchymal Stem Cells Into Cardiomyocytes," *C.R. Biol.*, 2002; 325:1027-1038.
Galán, L. et al., "Cell therapy in amyotrophic lateral sclerosis: science and controversy," *Neurologia*, 2010: 25(8):467-469.
Garbuzova-Davis, S. et al., "Human Umbilical Cord Blood Treatment in a Model of ALS: Optimization of Cell Dose," *PLoS One*, 2008; 3(6):e2494.
Garbuzova-Davis, S. et al., "Intravenous Administration of Human Umbilical Cord Blood Cells in a Mouse Model of Amyotrophic Lateral Sclerosis: Distribution, Migration, and Differentiation," *Journal of Hematotherapy & Stem Cell Research*, 2003; 12:255-270.
Garbuzova-Davis, S. et al., "Multiple Intravenous Administrations of Human Umbilical Cord Blood Cells Benefit in a Mouse Model of ALS," *PLoS One*, 2012; 7(2):e31254.
Gellersen, B. et al., "Cyclic AMP and Progesterone Receptor Cross-Talk in Human Endometrium: A Decidualizing Affair," *J. Endocrinol.*, 2003; 178(3):357-372.
Generalli, T.A. et al., "Axonal injury in the optic nerve: a model stimulating diffuse axonal injury in the brain," *J. Neurosurg*, 1989; 71:244-253.
Gerdes, D. et al., "Cloning and Tissue Expression of Two Putative Steroid Membrane Receptors," *Biol. Chem.*, 1998; 379:907-911.
Germano, A.F. et al., "Behavioral deficits following experimental subarachnoid hemorrhage in the rat," *J. Neurotrauma*, 1994; 11:345-352.
Giunta et al., "Inflammaging as a Prodrome b Alzheimer's Disease," Journal of Neuroinflammation, 2008; 5(1):51.

Gökhan, S. et al., "Basic and Clinical Neuroscience Applications of Embryonic Stem Cells," *Anat. Rec. (New Anat)*, 2001; 265:142-156.
Gong, C., etal., "Acute Inflammatory Reaction Following Experimental Intracerebral Hemorrhage in Rat," *Brain Res,* 2000; 871:57-65.
Gong, C., et al., "Intracerebral Hemorrhage-Induced Neuronal Death," *Neurosurgery,* 2001; 48(4):875-883.
Goodwin, H.S. et al., "Multilineage Differentiation Activity by Cells Isolated from Umbilical Cord Blood: Expression of Bone, Fat, and Neural Markers," *Biology of Blood and Marrow Transplantation*, 2001; 7:581-588.
Gosiewska, A. et al., "Development of a Three-Dimensional Transmigration Assay for Testing Cell-Polymer Interactions for Tissue Engineering Applications," *Tissue Eng.*, 2001; 7(3):267-277.
Gottleib, D.I. "Large-Scale Sources of Neural Stem Cells," *Annu. Rev. Neurosci.*, 2002; 25:381-407.
Gröhn, P. et al.,"Collagen-Coated $Ba^{2+}$-Alginate Microcarriers for the Culture of Anchorage-Dependent Mammalian Cells," *BioTechniques,* 1997; 22(5): 970-975.
Gros-Louis, F. et al., "Intracerebroventricular infusion of monoclonal antibody or its derived Fab fragment against misfolded forms of SOD1 mutant delays mortality in a mouse model of ALS," *J. Neurochem.*, 2010; 113(5) 1188-1189.
Gupta, S. et al., "Isolation and Characterization of Kidney-Derived Stem Cells," *J. of Am. Soci. of Nephrol.*, 2006; 17(11):3028-3040.
Halvorsen, Y.C. et al., "Extracellular Matrix Mineralization and Osteoblast Gene Expression by Human Adipose Tissue-Derived Stromal Cells," *Tissue Eng.*, 2001; 7(6):729-741.
Hanahan, D. "Heritable Formation of Pancreatic β-Cell Tumours in Transgenic Mice Expressing Recombinant Insulin/Simian Virus 40 Oncogenes," *Nature,* 1985; 315:115-122.
Hartgerink, J.D. et al.,"Peptide-Arnphiphile Nanofibers: A Versatile Scaffold for the Preparation of Self-Assembling Materials," *PNAS,* 2002; 99(8):5133-5138.
Haruta, M. et al., "In Vitro and In Vivo Characterization of Pigment Epithelial Cells Differentiated From Primate Embryonic Stem Cells," *Investig. Ophthalmol. & Visual Sci.*, 2004; 45(3):1020-1025.
Hayflick, L., "The Longesvity of Cultured Human Cells," *J. Am. Geriatr. Soc.*, 1974; 22(1):1-12.
Hayflick, L., "The Strategy of Senescence," *Gerontologist*, 1974; 14(1):37-45.
Haynesworth et al., "Cell Surface Antigens on Human Marrow-Derived Mesenchymal Cells are Detected by Monoclonal Antibodies," Bone, 1992; 13:69-80.
Herrera, M.B. et al., "Mesenchymal Stem Cells Contribute b the Renal Repair of Acute Tubular Epithelial Injury," *Int. J. Mol. Med.*, 2004; 14(6):1035-1041.
Hill, D.P. et al., "Screening for Novel Pattern Formation Genes Using Gene Trap Approaches," *Methods in Enzymology,* 1993; 225:664-681.
Hill, M. et al., "Treatment for Swallowing Difficulties (Dysphagia) In Chronic Muscle Disease," *The Cochrane Library Cochrane Database Syst Rev.*, 2004; 2:1-12.
Hishikawa, K. et al., "Musculin/MyoR is Expressed in Kidney Side Population Cells and Can Regulate Their Function," *Journal of Cell Biology,* 2005; 169(6):921-928.
Holz, F.G. et al., "Intraocular Microablation of Choroidal Tissue by a 308 nm AIDA Excimer Laser for RPE-Transplantation in Patients With Age-Related Macular Degeneration," *Biomed. Technik,* 2003; 48:82-85.5
Hongpaisan, J., "Inhibition of Proliferation of Contaminating Fibroblasts by D-Valine In Cultures of Smooth Muscle Cells From Human Myometrium," *Cell Biol. Int.*, 2000; 24(1):1-7.
Hoynowski, S.M. et al., "Characterization and Differentiation of Equine Umbilical Cord-Derived Matrix Cells," *Biochemical and Biophysical Research Communications,* 2007; 362:347-353.
Hu, A. et al., "Heptatic Differentiation From Embryonic Stem Cells In Vitro," *Chin. Med. J.*, 2003; 116(12):1893-1897.
Hu, A. et al., "Behavioral Tests After Intracerebral Hemorrhage in the Rat," *Stroke*, 2002; 599 33:2478-2484.
Hua, Y., et al., "Plasminogen Activator Inhibitor-1 Induction after Experimental Intracerebral Hemorrhage," *J. Cereb Blood Flow Metab,* 2002; 22:55-61.

(56) References Cited

OTHER PUBLICATIONS

Hughes, G.C. et al., "Therapeutic Angiogenesis In Chronically Ischemic Procine Myocardium: Comparative Effects of BFGF and VEGF," *Ann. Thorac. Surg.*, 2004; 77:812-818.

Hutmacher, D.W., "Scaffold Design and Fabrication Technologies for Engineering Tissues—State of the Art and Future Perspectives," *J. Biomater. Sci. Polymer Edn.*, 2001;12(1):107-124.

Igura et al. "Human Placental Derived Stem Cells Differentiate into Neural Cells," Blood, 2002; 100(11): 517A (Abstract 2021).

Ilieva, H. et al., "Non-cell autonomous toxicity in neurodegenerative disorders: ALS and beyond," *J. Cell Biol.*, 2009; 187:761-772.

In't Anker, P., et al., "Isolation of Mesenchymal Stem Cells of Fetal or Maternal Origin from Human Placenta," *Stem Cells*, 2004; 22:1338-1345.

Isacson, O., "The Production and Use of Cells As Therapeutic Agents in Neurodegenerative Diseases," *The Lancet (Neurology)*, 2003, 2:417-424.

Isacson, O., et al., "Specific Axon Guidance Factors Persist in the Adult Brain Asro Demonstrated by Pig Neuroblasts Transplanted to the Rat," *Neurosci.*, 1996; 75(3):827-837.

Ishii, M. et al., "Molecular Markers Distinguish Bone Marrow Mesenchymal Stem Cells From Fibroblasts," *Biochemical and Biophysical Research Communications*, 2005; 332:297-303.

Israelson, A. et al., "Misfolded Mutant SOD1 Directly Inhibits VDAC1 Conductance in a Mouse Model if in hereited ALS," *Neuron*, 2010; 67(4):575-587.

Ito, Y. et al., "A Quantitative Assay Using Basement Membrane Extracts to Study Tumor Angiogenesis in Vivo," *Int. J. Cancer*, 1996; 67:148-152.

Jackson, K.A. et al., "Regeneration of Ischemic Cardiac Muscle and Vascular Endothelium by Adult Stem Cells," *J. Clin. Invest.*, 2001; 107:1395-1402.

Jaffe, E.A. et al., "Culture of Human Endothelial Cells Derived From Umbilical Veins; Identification by Morphologic and Immunologic Criteria" *J Clin Invest*, 1973; 52:2745-2756.

Janderová, L. et al., "Human Mesenchymal Stem Cells As an In Vitro Model for Human Adipogenesis," *Obes. Res.*, 2003; 11(1):65-74.

Jang, Y.K. et al.,"Retinoic Acid-Mediated Induction of Neurons and Glial Cells From Human Umbilical Cord-Derived Hematopoietic Stem Cells," *J. Neurosci. Res.*, 2004; 75:573-584.

Jikuhara, T. et al., "Left Atrial Function As a Reliable Predictor of Exercise Capacity in Patients With Recent Myocardial Infarction," *Chest*, 1997; 111(4):922-928.

Jin et al., "Neurogenesis in Dentate Subgranular Zone and Rostral Subventricular Zone After Focal Cerebral Ischemia in the Rat," *PNAS*, 2001; 98(8):4710-4715.

Johe, K.K. et al., "Single Factors DirectThe Differentiation of Stem Cells From the Fetal and Adult Central Nervous System," *Genes & Devel.*, 1996; 10:3129-3140.

Johnstone, B. et al., "In Vitro Chondrogenesis of Bone-Marrow-Derived Mesenchymal Progenitor Cells," *Exp. Cell Res.*, 1998; 238:265-272.

Jomura, S. et al., "Potential Treatment of Cerebral Global Ischemia with Oct-4+ Umbilical Cord Matrix Cells," *Stem Cells*, 2006, AlphaMed Press, Downbaded from www.StemCells.com at Ethicon, Inc. on Sep. 11, 2006 and Supplemental Data: 2.

Jones, J. et al., "Insulin-Like Growth Factors and their Binding Proteins: Biological Actions," Endocrine Review, 1995; 16(1):3-34.

Jones-Villeneuve, E.M. et al., "Retinoic Acid-Induced Neural Differentiation of Embryonic Carcinoma Cells," *Mol. & Cellu. Biol.*, 1983; 3(12):2271-2279.

Jørgensen, N.R. et al., "Intercellular Calcium Signaling Occurs Between Human Osteoblasts and Osteoclasts and Requires Activation of Osteoclast P2X7 Receptors," *The Journal of Biological Chemistry*, 2002; 277(9):7574-7580.

Joussen, A.M. "Cell Transplantation in Age Related Macular Degeneration: Current Concepts and Future Hopes," *Graefe's Arch. Clin. Exp. Ophthalmol.*, 2004; 242:1-2.

Jubran, et al., "Repair of peripheral nerve transections with fibrin sealant containing neurotrophic factors." *Exp. Neural*, 2002: 181: 204-212.

Kadiyala, S. et al., "Culture Expanded Canine Mesenchymal Stem Cells Possess Osteochondrogenic Potential In Vivo and In Vitro," *Cell Transplant.*, 1997; 6(2):125-134.

Karussis, D. et al., "Safety and immunological effects of mesenchymal stem cell transplantation in patients with Multiple sclerosis and amyotrophic lateral sclerosis," *Arch Neuorol.*, 2010; 67(10):1187-1194.

Kawata, M. et al., "Transcriptional Control of HLA-A,B,C Antigen in Human Placental Cytotrophoblast Isolated Using Trophoblast- and HLA-Specific Monocbnal Antibodies and the Fluorescence-Activated Cell Sorter," *J. Exp. Med.*, 1984; 160:633-651.

Kestendjieva, S. et al., "Characterization of mesenchymal stem cells isolated from the human umbilical cord." Cell Biology International, 2008; 32: 724-732.

Keyvani et al., "Plasticity-Associated Molecular and Structural Events in the Injured Brain," *Journal of Neuropathology Experimental Neurology*, 2002; 61(10):831-840.

Kicic, A. et al., "Differentiation of Marrow Stromal Cells Into Photoreceptors in the Rat Eye," *J. of Neurosci.*, 2003; 23(21):7742-7749.

Kim, J. et al., "Dopamine Neurons Derived From Embryonic Stem Cells Function in an Animal Model of Parkinson's Disease," *Nature*, 2002; 418:50-56.

Kim, J.Y. et al., "Ocular Surface Reconstruction: Limbal Stem Cell Transplantation," *Ophthal. Clin. N. Am.*, 2003; 16:67-77.

Kim, K.J. et al., "Comparison of Three Rodent Neuropathic Pain Models," *Exp. Brain Res.*, 1997; 113:200-206.

Kim, S.H. et al., "An experimental model for peripheral neuropathy produced by segmental spinal nerve ligation in the rat," *Pain*, 1992; 50:355-363.

Kim, S.K. et al.,"Intercellular Signals Regulating Pancreas Development and Function," *Genes Dev.*, 2001; 15:111-127.

Kirschstein, R. et al., "Can Stem Cells Repair a Damaged Heart?" *Stem Cells: Scientific Progress and Future Research Directions*, 2001; 87-92.

Kitamura, S. et al., "Establishment and Characterization of Renal Progenitor Like Cells from S3 Segment of Nephron in Rat Adult Kidney," *The FASEB Journal*, 2005; 19:1789-1797.

Klass et al., "Intravenous Mononuclear Marrow Cells Reverse Neuropathic Pain from Experimental Mononeuropathy," International Anesthesia Research Society, 2007; 104:944-949.

Klassen, H. et al., "Stem Cells and Retinal Repair," *Prog. Retin. Eye Res.*, 2004; 23:149-181.

Kolb, B, "Synaptic Plasticity and the Organization of Behaviour after Early and Late Brain Injury," *Canadian Journal of Experimental Psychology*, 1999; 53(1):62-76.

Kollmar, R. et al., "Neuroprotective effect of delayed moderate hypothermia after focal cerebral ischemia: an MRI study," *Stroke*, 2002; 33:1899-1904.

Komitova, M., "Enriched environment increases neural stem/progenitor cell proliferation and neurogenesis in the subventricular zone of stroke-lesioned adult rats," *Stroke*, 2005; 36:1276-82.

Kopen et al., "Marrow stromal cells migrate throughout forebrain and cerebellum, and they differentiation into astrocytes after injection into neonatal mouse brains," *PNAS*, 1999; 96:107111-10716.

Koyama, S. and Alzawa, M., "Mechanisms of Electrically Regulated Cellular Functions," *Kagaku to Seibutsu (Chemistry and Biology)*, 2000; 38(8): 503-507 (with English Abstract).

Kurtz, A. et al., "Activity in Fetal Bovine Serum that Stimulates Erythroid Colony Formation in Fetal Mouse Livers is Insulinlike Growth Factor 1," *J. Clin. Invest.*, 1985; 76:1643-1648.

Kusama, V. et al., "Growth and morphogenesis of mouse prostate epithelial cells in collagen gel matrix culture" *Cell Biol Int Rep*, 1989; 13:569-575.

Laface, D. et al., "Gene Transfer Into Hematopoietic Progenitor Cells Mediated by an Adeno-Associated Virus Vector," *Virology*, 1988; 162:483-486.

Lang, K.J.D. et al., "Differentiation of Embryonic Stem Cells to a Neural Fate: A Route to Re-Building the Nervous System?" *J. of Neurosci. Res.*, 2004; 76:184-192.

(56) References Cited

OTHER PUBLICATIONS

Langeggen, H. et al.,"HUVEC Take Up Opsonized Zymosan Particles and Secrete Cytokines IL-6 and IL-8 In Vitro," *FEMS Immunol. Med. Microbiol.*, 2003; 36:55-61.
Le Belle, J.E. et al., "Stem Cells for Neurodegenerative Disorders: Where Can We Go From Here?," *Biodrugs*, 2002; 16(6):389-401.
Le Bouteiller, P. et al., "Soluble HLA-G1 At The Materno-Foetal Interface-A Review," *Placenta*, 2003; 24(Suppl. A):S10-S15.
Lee, H.J. et al., "Brain transplantation of immortalized human neural stem cells promotes.functional recovery in mouse intracerebral hemorrhage stroke model," *Stem Cells*, 2007; 25:1204-12.
Lee, O. et al., "Isolation of Multipotent Mesenchymal Stem Cells from Umbilical Cord Blood," *Blood*, 2004; 103:1669-1675.
Lee, S-T. et al., "Quantification of human neural stem cell engraftments in rat brains using ERV-3 real-time PCR," *Journal of Neuroscience Methods*, 2006; 157:225-229.
Lepore, AC et al., "Neural precursor cells can be delivered into the injured cervical spinal cord by intrathecal injection at the lumbar cord," *Brain Res.*, 2005; 1045(1-2):206-216.
Li, A. et al., "IL-8 Directly Enhanced Endothelial Cell Survival, Proliferation, and Matrix Metalloproteinases Production and Regulated Angiogenesis," *J. Immunol.*, 2003; 170:3369-3376.
Li, C.D. et al, "Mesenchymal Stem Cells Derived From Human Placenta Suppress Allogeneic Umbilical Cord Blood Lymphocyte Proliferation," *Cell Research*, 2005; 15(7):539-547.
Li, L.X. et al., "Inherited Retinal Dystrophy in the RCS Rat: Prevention of Photoreceptor Degeneration by Pigment Epithelial Cell Transplantation," *Exp. Eye Res.*, 1988; 47:911-917.
Li, Y. et al., "Intracerebral Transplantation of Bone Marrow Stromal Cells in a 1-Methyl-4-Phenyl-1,2,3,6-Tetrahydropyridine Mouse Model of Parkinson's Disease," *Neuroscience Letts.*, 2001; 315:67-70.
Li, Y. et al., "Transplanted Olfactory Ensheathing Cells Promote Regeneration of Cut Adult at Artery Occlusion in the Rat," *J. of Neuro.*, 2003; 23(21):7783-7788.
Li, Y. et al., "Intact, Injured, Necrotic and Apoptotic Cells after Focal Cerebral Ischemia in the Rat," *J. Neurol. Sci.*, 1998; 156:119-132.
Li, Y. et al., "Ultrastructural and Light Microscopic Evidence of Apoptosis after Middle Cerebral Artery Occlusion in the Rat," *Am. J. Pathol.*, 1995; 146(5):1045-1051.
Li, Y. et al., "Human Marrow Stromal Cell Therapy for Stroke in Rat Neurotrophins and Functional Recovery," *Neurology*, 2002; 59:514-523.
Liddiard, et al., "An Improved Method for the Preparation of Human Fetal and Adult Hepatocytes," *Arch. Toxicol.*, 1980; 44:107-112.
Lindenlaub, T. et al.,"Partial Sciatic Nerve Transection as a Model of Neuropathic Pain: A Qualitative and Quantitative Study," *Pain*, 2000; 89: 97-106.
Lindvall, O. et al., "Stem Cell Therapy for Human Neurodegenerative Disorders—How to Make It Work," *Nature Medicine*, 2004;10(Suppl.):S42-S50.
Liu, Y. et al., "Molecular and Genetic Mechanisms of Obesity: Implications for Future Management," *Curr. Mol. Med.*, 2003; 3(4):325-340.
Liu, K. et al, "Constitutive and Regulated Expression of Telomerase Reverse Transcriptase (hTERT) in Human Lymphocytes," *Proc. Natl. Acad. Sci.*, 1999; 96:5147-5152.
Lockhart, D.J. et al.,"Expression Monitoring by Hybridization to High-Density Oligonucleotide Arrays," *Nat. Biotechnol.*, 1996; 14:1675-1680.
Lodie, T.A. et al., "Systematic Analysis of Reportedly Distinct Populations of Mulitpotent Bone Marrow-Derived Stem Cells Reveals a Lack of Distinction," *Tissue Engineering*, 2002; 8(5):739-751.
Lois, C. et al., "Chain Migration of Neuronal Precursors," *Science*, 1996; 271:978-981.

Lu, F-Z et al. "Characterization and gene transfer in mesenchymal stem cells derived from human umbilical-cord blood," *J. Lab Clin. Med.*, 2005; 146:271-278.
Lund, R.D. et al., "Cell Transplantation As a Treatment for Retinal Disease," *Progress in Retinal and Eye Research*, 2001; 20(4):415-449.
Lund, R.D. et al., "Subretinal Transplantation of Genetically Modified Human Cell Lines Attenuates Loss of Visual Function in Dystrophic Rats," *PNAS*, 2001; 98(17):9942-9997.
Lund, R.D. et al.,"Retinal Transplantation: Progress and Problems in Clinical Application," *J. Leukocyte Biol.*, 2003; 74:151-160.
Luo, D. et al., "Synthetic DNA Delivery Systems," *Nat. Biotechnol.*, 2000; 18(1):33-36.
Luyten, F.P. et al., "Skeletal Tissue Engineering: Opportunities and Challenges," *Best Pract. Res. Clin. Rheumatol.*, 2001; 15(5):759-769.
Ma, L. et al., "Human Umbilical Cord Wharton's Jelly-Derived Mesenchymal Stem Cells Differentiation into Nerve-Like Cells," *Chinese Med. Jour.*, 2005; 118(23):1987-1993.
MacDonald, R.J. "Expression of the Pancreatic Elastase I Gene in Transgenic Mice," *Hepatology*, 1987; 7(1):42S-51S.
MacKay, A.M. et al., "Chondrogenic Differentiation of Cultured Human Mesenchymal Stem Cells From Marrow," *Tissue Engineering*, 1998; 4(4):415-428.
Makino, S. et al., "Cardiomyocytes can be generated from marrow stromal cells in vitro," *J. Clin. Invest.*, 1999; 103:697-705.
Marx, W.F. et al., "Endovascular Treatment of Experimental Aneruysms By Use of Biologically Modified Embolic Devices: Coil-Mediated Intraaneurysamal Delivery of Fibroblast Tissue Allogafts," *Am. J. Neuroradiol.*, 2001;22:323-333.
Mason, A.J. et al., "The Hypogonadal Mouse: Reproductive Functions Restored by Gene Therapy," *Science*, 1986; 234:1372-1378.
Matsuo, Y. et al ., "Protective effect of endothelin type a receptor antagonist on brain edema and injury after transient middle cerebral artery occlusion in rats," *Stroke*, 2001; 32:2143-2148.
Matsushita et al., "Evidence for Apoptosis After Intracerebral Hemorrhage in Rat Striatum," *Journal of Cerebral Blood Flow & Metabolism*, 2000; 20:396-404.
Mayer-Proschel, M. et al., "Isolation of Lineage-Restricted Neuronal Precursors From Multipotent Neuroepithelial Stem Cells," *Neuron.*, 1997; 19:773-785.
Medicetty, S. et al., "Transplantation of Human Umbilical Cord Matrix Stem Cells Alleviates Apomorphine-Induced Rotations in Parkinsonian Rats", 2003, XP-002383776, 1 page.
Meier et al., "Spastic Paresis After Perinatal Brain Damage in Rats is Reduced by Human Cord Blood Monomuclear Cells," *Pediatric Research*, 2006; 59(2):244-249.
Melero-Martin, J. et al., "Optimal In-Vitro Expansion of Chondroprogenitor Cells in Monolayer Culture," *Biotechnology and Bioengineering*, 2006; 93(3):519-533.
Merx, M.W. et al., "Transplantation of Human Umbilical Vein Endothelial Cells Improves Left Ventricular Function in a Rat Model of Myocardial Infarction," *Basic Res. Cardiol.*, 2005; 100:208-216.
Messina, D.J., et al., "Comparison of Pure and Mixed Populations of Human Fetal-Derived.Neural Progenitors Transplanted Into Intact Adult Rat Brain," *Exper. Neurol.*, 2003; 184:816-829.
Miñambres et ai., "Cerebral Apoptosis in Severe Traumatic Brain Injury Patients: An In Vitro, In Vivo, and Postmortem Study," *Journal of Neurotrauma*, 2008; 25:581-591.
Mitchell, K.E. et al., "Matrix Cells From Wharton's Jelly Form Neurons and Glia," *Stem Cells*, 2003; 21:50-60.
Mokudai, T. et al.,"Delayed treatment with nicotinamide (Vitamin B3) improves neurological outcome and reduces infarct volume after transient focal cerebral ischemia in Wi star rats," *Stroke*, 2000; 31:1679-1685.
Moll, S. et al., "Monitoring Warfarin Therapy in Patients With Lupus Anticoagulants," *Ann. Intern. Med.*, 1997; 127(3):177-185.
Mombaerts, P. et al., "Creation of a Large Genomic Deletion At the T-Cell Antigen Receptor β-Subunit Locus in Mouse Embryonic Stem Cells by Gene Targeting," *Proc. Nat. Acad. Sci. USA*, 1991; 88:3084-3087.

(56) References Cited

OTHER PUBLICATIONS

Morgenstern, J.P. et al., "Advanced Mammalian Gene Transfer: High Titre Retroviral Vectors With Multiple Drug Selection Markers and a Complementary Helper-Free Packaging Cell Line," *Nucleic Acids Res.,* 1990; 18(12):3587-3596.
Moore, A.E. et al.,"Parkinsonian Motor Deficits are Reflected by Proportional A9/A10 Dopamine Neuron Degeneration in the Rat," *Exp. Neurol.,* 2001; 172(2):363-376.
Morigi, M. et al., "Mesenchymal Stem Cells are Renotropic, Helping to Repair the Kidney and Improve Function in Acute Renal Failure," *J. Am. Soc. Nephrol.,* 2004; 15(7):1794-1804.
Morishima, Y. et al., "The Clinical Significance of Human Leukocyte Antigen (HLA) Allele Compatibility in Patients Receiving a Marrow Transplant from Serologically HLA-A, HLA-B, and HLA-DR Matched Unrelated Donors," *Blood,* 2002; 99(11):4200-4206.
Moulder, J.E., "Pharmacological Intervention to Prevent or Ameliorate Chronic Radiation Injuries," *Semin. Radiat. Oncol.,* 2003; 13(1):73-84.
Nakamura, T. et al.,"Ocular Surface Reconstruction Using Cultivated Mucosal Epithelial Stem Cells," *Cornea,* 2003; 22(Supp. 1):S75-S80.
Naughton, B.A. et al., "Cells isolated from Wharton's jelly of the human umbilical cord develop a cartilage phenotype when treated with TGF-b in vitro," 1997; *FASEB J* 11:A19 (Abstract 108).
Nicosia, R.F. et al., "Modulation of Microvascular Growth and Morphogenesis by Reconstituted Basement Membrane Gel in Three-Dimensional Cultures of Rat Aorta: A Comparative Study of Angiogenesis in Matrigal, Collagen, Fibrin, and Plasma Clot," *In Vitro Cell Dev. Biol.,* 1990; 26:119-128.
Nikolic, W. et al., "Peripherally administered human umbilical cord blood cells reduce parenchymal and vascular beta-amyloid deposits in Alzheimer mice", Stem Cells Dev., 2008 ; 17(3): 423-439.
Ninichuk, V. et al.,"Multipotent Mesenchymal Stem Cells Reduce Interstitial Fibrosis But Do Not Delay Progression of Chronic Kidney Disease in Collagen4A3-Deficient Mice," *Kidney Int.,* 2006; 70(1):121-129.
Nishishita, T. et al., "A Potential Pro-Angiogenic Cell Therapy With Human Placenta-Derived.Mesenchymal Cells," *Biochemical and Biophysical Research Communications,* 2004; 325:24-31.
Nixon, P.J. et al., "The Contribution of Cone Responses to Rat Electroretinograms," *Clin. Experiment Ophthalmol.,* 2001; 29(3):193-196.
Nork, T.M. et al., "Swelling and Loss of Photoreceptors in Chronic Human and Experimental Glaucomas," *Arch. Ophthalmol.,* 2000; 118:235-245.
Nusinowitz, S. et al.,"Rod Multifocal Electroretinograms in Mice," *Invest Ophthalmol Vis. Sci.,* 1999; 40(12): 2848-2858.
Ochs, G. et al.,"Epi-arachnoidal drug deposit: A rare complication of intrathecal drug therapy," *J Pain Symptom Manage,* 1999; 18:229-232.
Oh, S.H. et al., "Hepatocyte Growth Factor Induces Differentiation of Adult Rat Bone Marrow Cells Into a Hepatocyte Lineage In Vitro," *Biochem. & Biophys. Res. Comm.,* 2000; 279(2):500-504.
Okuda-Ashitaka et al., "Molecular mechanisms of pain and new approaches for pain management," *Experimental Medicine,* 2000; 18: 2332-2337 (with English Abstract).
Okumoto, K. et al., "Differentiation of Bone Marrow Cells Into Cells That Express Liver-Specific Genes In Vitro: Implication of the Notch Signals in Differentiation," *Biochem. & Biophys. Res. Commun.,* 2003; 304:691-695.
Orlic, D. et al., "Stem Cells for Myocardial Regeneration," *Circ. Res.,* 2002; 91:1092-1102.
Ornitz, D.M. et al., "Elastase I Promoter Directs Expression of Human Growth Hormone and SV40 T Antigen Genes to Pancreatic Acinar Cells in Transgenic Mice," *Cold Spring Harbor Symp. Quant. Biol.,* 1985; 50:399-409.
Osborne, N.N. et al., "Some Current Ideas on the Pathogenesis and the Role of Neuroprotection in Glaucomatous Optic Neuropathy," *Eur. J. Ophthalmol.,* 2003; 13(Supp. 3):S19-S26.

Palù, G. et al., "In Pursuit of New Developments for Gene Therapy of Human Diseases," *J. Biotechnol.,* 1999; 68:1-13.
Pan, Y. et al., "Acute Treatment of Focal Cerebral Ischemia in Rats with Intracarotid Administration of Human Umbilical Cord Blood Cells," *Neurology,* 2003; 60(Suppl 1.): A63-A64 (Abstract P01.127).
Panepucci, R.A. et al., "Comparison of Gene Expression of Umbilical Cord Vein and Bone Marrow-Derived Mesenchymal Stem Cells," *Stem Cells,* 2004; 22:1263-1278.
Parent et al., "Rat Forebrain Neurogenesis and Striatal Neuron Replacement After Focal Stroke," *Ann. Neurol.,* 2002; 52:802-813.
Pera, M.F. et al., "Human Embryonic Stem Cells", *J. Cell Science,* 2000; 113:5-10.
Pesce et al.,"Myoendothelial Differentiation of Human Umbilical Cord Blood-Derived Stem Cells in Ischemic Limb Tissues," *Circulation Research,* 2003; 93:e51-e62.
Petersdorf, E.W., "HLA Matching in Allogeneic Stem Cell Transplantation," *Curr. Op. Hematol,* 2004; 11:386-391.
Pfefferkorn T, and Rosenberg G.A. "Closure of the blood-brain barrier by matrix metalloproteinase inhibition reduces rtP A-mediated mortality in cerebral ischemia with delayed reperfusion," *Stroke,* 2003; 34:2025-2030.
Phillips, A., "The challenge of gene therapy and DNA delivery," *J Pharmacology,* 2001; 53:1169-1117.
Phipps, J.A. et al., "Paired-Flash Identification of Rod and Cone Dysfunction in the Diabetic Rat," *Investigative Ophthalmology & Visual Science,* 2004;45:4592-4600.
Pisharod I, M. et al., "An Animal Model for Neuron-Specific Spinal Cord Lesions by the Microinjection of N-Methylaspartate, Kainic Acid, and Quisqualic Acid," 1985; *Appl. Neurophysiology* 48:226-233.
Pittenger, M.F. et al., "Multilineage Potential of Adult Human Mesenchymal Stem Cells," *Science,* 1999; 284:143-47 and seven pages of online supplementary material.
Pittenger, M.F. et al., "Mesenchymal Stem Cells and Their Potential as Cardiac Therapeutics," *Circ. Res.,* 2004; 95:9-20.
Plaia, T., et al., "Characterization of a New NIH-Registered Variant Human Embryonic Stem Cell Line, BG01V: A Tool for Human Embryonic Stem Cell Research," *Stem Cells,* 2006: 24: 531-546.
Plate, KH, "Mechanisms of Angiogenesis in the Brain," *Journal of Neuropathology Experimental Neurology,* 1999; 58(4):313-320.
Pountos, I. et al., "Mesenchymal Stem Cell Tissue Engineering: Techniques for Isolation, Expansion and Application," *Injury, Int. J. Care Injured,* 2007; 38:S23-S33.
Rabbany, S.Y. et al., "Molecular Pathways Regulating Mobilization of Marrow-Derived Stem Cells for Tissue Revascularization," *TRENDS in Molecular Med.,* 2003; 9(3):109-117.
Rafii, S. et al., "Therapeutic Stem and Progenitor Cell Transplantation for Organ Vascularization and Regeneration," *Nature Med.,* 2003; 9(6):702-712.
Rahman, Z. et al., "Isolation and Primary Culture Urothelial Cells from Normal Human Bladder," *Urol. Research,* 1987; 15:315-320.
Ramon-Cueto, A. et al., "Functional Recovery of Paraplegic Rats and Motor Axon Regeneration in Their Spinal Cords by Olfactory Ensheathing Glia," *Neuron,* 2000; 25:425-435.
Readhead, C. et al., "Expression of a Myelin Basic Protein Gene in Transgenic Shiverer Mice: Correction of the Dysmyelinating Phenotype," *Cell,* 1987; 48:703-712.
Refaie, A. et al., "Experimental Islet Cell Transplantation in Rats: Optimization of the Transplantation Site," *Trans. Proc.,* 1998; 30:400-403.
Rehman, J. et al., "Secretion of Angiogenic and Antiapoptotic Factors by Human Adipose Stromal Cells," *Circulation,* 2004; 109:1292-1298.
Reubinoff, B.E. et al., "Neural Progenitors From Human Embryonic Stem Cells," *Nature Biotechnology,* 2001; 19:1134-1140.
Reyes, M. et al., "Purification and Ex Vivo Expansion of Postnatal Human Marrow Mesodermal Progenitor Cells," *Blood,* 2001; 98(9):2615-2625.
Rezai, K.A. et al., "Iris Pigment Epithelium Transplantation," *Graefe's Arch. Clin. Ophthalmol.,* 1997; 235:558-562.

(56) References Cited

OTHER PUBLICATIONS

Rickard, D.J. et al., "Induction of Rapid Osteoblast Differentiation in Rat Bone Marrow Stromal Cell Cultures by Dexamethasone and BMP-2," *Dev. Biol.*, 1994; 161:218-228.
Rios, M. et al., "Catecholamine Synthesis is Mediated by Tyrosinase in the Absence of Tyrosine Hydroxylase," *J. Neurosci.*, 1999; 19(9):3519-3526.
Rivlin, A.S. et al.,"Objective clinical assessment of motor function after experimental spinal cord injury in the rat," *J Neurosurg*, 1977; 47:577-581.
Romanov, Y.A. et al., "Searching for Alternative Sources of Post-natal Human Mesenchymal Stem Cells: Candidate MSX-Like Cells from Umbilical Cord," *Stem Cells*, 2003; 21:105-110.
Rosen, E.M. et al.,"HGF / SF in Angiogenesis," *Ciba Found. Symp.*, 1997; 212:215-229.
Roskams, A.J. et al., "Directing Stem Cells and Progenitor Cells on the Stage of Spinal Cord Injury," *Exp. Neural.*, 2005; 193:267-272.
Russo, E., Cultivating Policy from Cell Types, *The Scientist*, 2001; 15(11):6 (printout is numbered 1-6).
Rutherford, A. et al., "Eyeing-Up Stem Cell Transplantation," *Trends in Molecular Medicine*, 2001; 7(1):11.
Ryadnov, M.G. et al., "Engineering the Morphology of a Self-Assembling Protein Fibre," *Nat. Mater.*, 2003; 2:329-332.
Sagrinat I, C. et al., "Isolation and Characterization of Multipotent Progenitor Cells from the Bowman's Capsule of Adult Human Kidney," *Journal of American Society of Nephrology*, 2006; 17:2443-2456.
Sahn, D.J. et al.,"Recommendations Regardhg Quantitation in M-Mode Echocardiography: Results of a Survey of Echocardiographic Measurements," *Circulation*, 1978; 58(6):1072-1083.
Sakariassen, K.S. et al., "Methods and Models to Evaluate Shear-Dependent and Surface Reactivity-Dependent Antithrombotic Efficacy," *Thromb. Res.*, 2001; 104:149-174.
Salcedo, R. et al., "Human Endothelial Cells Express CCR2 and Respond to MCP-1: Direct Role of MCP-1 in Angiogenesis and Tumor Progression," *Blood*, 2000; 96(1):34-40.
Salgado, A.J. et al., "Bone Tissue Engineering: State of the Art and Future Trends," *Macromol. Biosci.*, 2004; 4:743-765.
Sauvé, Y. et al., "The Relationship Between Full Field Electroretinogram and Perimetry-Like Visual Thresholds in RCS Rats During Photoreceptor Degeneration and Rescue by Cell Transplants," *Vision Res.*, 2004; 44(1):9-18.
Schallert, T. et al., "Use-Dependent Structural Events in Recovery of Function," *Brain Plasticity, Adv. Neurol.*, 1997; 73:229-238.
Schouten, J.W. et al., "A Review and Rationale for the Use of Cellular Transplantation as a Therapeutic Strategy for Traumatic Brain Injury," *Journal of Neurotrauma*, 2004; 21(11):1501-1538.
Schraermeyer, U. et al., "Subretinally Transplanted Embryonic Stem Cells Rescue Photoreceptor Cells From Degeneration in the RCS Rats," *Cell Transplantation*, 2001; 10:673-680.
Schreuder, G.M. et al., "The HLA Dictionary 1999: A Summary of HLA-A, -B, -C, DRB1/3/4/5, -DQB1 Alleles and Their Association with Serologically Defined HLA-A, -B, -C, -DR and -DQ Antigens," *Tissue Antigens*, 1999; 54:409-437.
Schwartz, R.E. et al.,"Multipotent Adult Progenitor Cells From Bone Marrow Differentiate Into Functional Hepatocyte-Like Cells," *J. of Clin. Invest.*, 2002; 109:1291-1302.
Seaver, S.S. et al. "The chick oviduct in tissue culture. I. Initial characterization of growing primary oviduct tissue cultures," *Exp. Cell Res.*, 1984; 155: 241-251.
Sébire, G. et al.,"In Vitro Production of IL-6, IL-1β, and Tumor Necrosis Factor-α by Human Embryonic Microglial and Neural Cells," *J. Immunol.*, 1993; 150(4):1517-1523.
Seiji, T. et al., Possibility of Regenerative Medicine Using Human Amniotic Cells, *Regenerative Medicine*, 2002; 1(2):79-85. English Language Abstract.
Sethe, S. et al., "Aging of Mesenchymal Stem Cells," *Ageing Research Reviews*, 2006; 5:91-116.
Seyfried, D. et al., "Effects of Intravenous Administration of Human Bone Marrow Stromal Cells After Intracerebral Hemorrhage in Rats," *J Neurosurg*, 2006; 104:313-318.
Seyfried, D. et al., "Improvement in Neurological Outcome after Administration of Atorvastatin Following Experimental Intracerebral Hemorrhage in Rats," *J Neurosuig*, 2004; 101:104-107.
Seyfried DM et al., "Mannitol enhances delivery of marrow stromal cells to the brain after experimental intracerebral hemorrhage," *Brain Res.*, 2008; 1224:12-19.
Shake et al., "Mesenchymal stem cell implantation in a swine myocardial infarct model: engraftment and functional effects," Ann Thorac Surg, 2002; 73:1919-1926.
Shani, M., "Tissue-Specific Expression of Rat Myosin Light-Chain 2 Gene in Transgenic Mice," *Nature*, 1985; 314:283-286.
Shimizu, T. et al., "Cell Sheet Engineering for Myocardial Tissue Reconstruction," *Biomaterials*, 2003; 24:2309-2316.
Shimizu, T. et al., "Fabrication of Pulsatile Cardiac Tissue Grafts Using a Novel 3-Dimensional Cell Sheet Manipulation Technique and Temperature-Responsive Cell Culture Surfaces," *Circulation Research*, 2002; 90:e40-e48.
Shuto, T. et al., "Dexamethasone Stimulates Osteoclast-Like Cell Formation By Inhibiting Granulocyte-Macrophage Colony-Stimulating Factor Production In Mouse Bone Marrow Cultures," *Endocrinology*, 1994; 134(3):1121-1126.
Simard, A.R., "Bone marrow-derived microglia play a critical role in restricting senile plaque formation in Alzheimer's disease," *Neuron*, 2006; 49:549-502.
Siminoff, R. et al., "Properties of Reptilian Cutaneous Mechanoreceptors," *Exp. Neurol.*, 1968; 20:403-414.
Song, H. et al., "Astroglia Induce Neurogenesis From Adult Neutral Stem Cells," *Nature*, 2002; 417:39-44.
Sordillo, L.M. et al., "Culture of Bovine Mammary Epithelial Cells in D-Valine Modified Medium: Selective Removal of Contaminating Fibroblasts," *Cell Biol. Int. Rep.*, 1988; 12(5):354-365.
Street, C.N. et al., "Stem Cells: A Promising Source of Pancreatic Islets for Transplantation In Type 1 Diabetes," *Curr. Top Dev. Biol.*, 2003; 58:111-136.
Stroemer et al., "Enhanced Neocortical Neural Sprouting, Synaptogenesis, and Behavioral Recovery with D-Amphetamine Therapy after Neocortical Infarction in Rats," *Stroke*, 1998; 29:2381-2395.
Stroemer et al., "Neocortical Neural Sprouting, Synaptogenesis, and Behavioral Recovery After Neocortical Infarction in Rats," *Stroke*, 1995; 26:2135-2144.
Sugaya, K., et al., "Practical Issues in Stem Cell Therapy for Alzheimer's Disease," *Current Alzheimer Research*, 2007; 4:370-377.
Sun et al. "Physical manipulation of calcium oscillations facilitates osteodifferentiation of human mesenchymal stem cells", *FASEB Journal*, 2007, 21:1471-1480.
Svendsen, C.N. "The Amazing Astrocyte," *Nature*, 2005; 417:29-32.
Svendsen, C.N. et al., "Long-Term Survival of Human Central Nervous System Progenitor Cells Transplanted Into A Rat Model of Parkinson's Disease," *Experim. Neurol.*, 1997; 148:135-146.
Swanson, R.A. et al., "A Semiautomated Method for Measuring Brain Infarct Volume," *J. Cereb. Blood Flow Metab.*, 1990; 10:290-293.
Swift, G.H. et al., "Tissue-Specific Expression of the Rat Pancreatic Elastase I Gene in Transgenic Mice," *Cell*, 1984; 38:639-646.
Szpak et al., "Border Zone Neovascularization in Cerebral Ischemic Infarct," *Folia Neuropathol*, 1999; 37(4):264-268. (Abstract only).
Tamura, A. et al., "Focal cerebral ischemia in the rat: 1. Description of technique and early neuropathological consequences following middle cerebral artery occlusion," *J Cereb Blood Flow Met*, 1981; 1:53-60.
Tao, W., "Application of Encapsulated Cell Technology for Retinal Degenerative Disease," *Expert. Opin. Biol. Ther.*, 2006; 6(7): 717-726.
Taylor, D.A. et al., "Regenerating Functional Myocardium: Improved Performance After Skeletal Myoblast Transplantation," *Nature Medicine*, 1998; 4(8):929-1200.

(56) References Cited

OTHER PUBLICATIONS

Taylor, D.A. et al., "Cardiac Chimerism As a Mechanism for Self-Repair: Does It Happen and If So To What Degree?" *Circulation*, 2002; 106:2-4.
Thorsby, E. et al., "Role of HLA Molecules in the Induction of Alloimmune Responses: Clinical Significance in the Cyclosporine Era," *Transplant Proc.*, 2004; 36(Suppl 2S):16S-21S.
Timmermans, F. et al., "Stem Cells for the Heart, Are We There Yet?" *Cardiology*, 2003; 100(4):176-185.
Toma, C. et al., "Human Mesenchymal Stem Cells Differentiate to a Cardiomyocyte Phenotype in the Adult Murine Heart," *Circulation*, 2002; 105:93-98.
Tomita, M. et al., "Bone Marrow-Derived Stem Cells Can Differentiate Into Retinal Cells in Injured Rat Retina," *Stem Cells*, 2002; 20:279-283.
Tremain, N. et al.,"MicroSAGE Analysis of 2,353 Expressed Genes in a Single Cell-Derived Colony of Undifferentiated Human Mesenchymal Stem Cells Reveals mRNAs of Multiple Cell Lineages," Stem Cells, 2001; 19:408-418.
Tresco, P.A. et al., "Cellular Transplants As Sources for Therapeutic Agents," *Advanced Drug Delivery Reviews*, 2000; 42:3-27.
Turner, D., "The Human Leucocyte Antigen (HLA) System," *Vox Sang.*, 2004; 87(Suppl 1):S87-S90.
Turner, J.F., "Inherited Retinal Dystrophy in the RCS Rat: Prevention of Photoreceptor Degeneration by Pigment Epithelial Cell Transplantation," *Exp. Eye Res.*, 1988; 47:911-917.
Tusher, V.G. et al., "Significance Analysis of Microarrays Applied to the bnizing Radiation Response," *PNAS*, 2001; 98(9):5116-5121.
Ujike, H. et al.,"Gene Expressbn Related b Synaptogenesis, Neuritogenesis, and MAP Kinase in Behavioral Sensitization to Psychostimulants," *Ann. N.Y. Acad. Sci.*, 2002; 965:55-67.
Ulloa-Montoya, F. et al., "Culture Systems for Pluripotent Stem Cells," *Journal of Bioscience and Bioengineering*, 2005; 100(1):12-27.
"Unigene Entry for Hs.522632, Homo Sapiens TMP Metallopeptidase Inhibitor 1 (TIMP1)," printed from http://www.ncbi.nlm.nih.gov/UniGene on Oct. 12, 2006.
Urbich, C. et al.,"Endothelial Progenitor Cells Characterization and Role in Vascular Biology," *Circ. Res.*, 2004; 95:343-353.
Vajsar, J. et al.,"Walker-Warburg Syndrome," *Orphanet Journal of Rare Diseases*, 2006; 1:29.
Van Hoffelen, S.J. et al., "Incorporation of Murine Brah Progenitor Cells Into the Developing Mammalian Retina," *Invest. Ophthalmol. Vis. Sci.*, 2003; 44(1):426-434.
Vassliopoulos, G. et al., "Transplanted Bone Marrow Regenerates Liver by Cell Fusion," *Nature*, 2003; 422:901-904.
Vendrame, M. et al., "Infusion of human umbilical cord blood cells in a rat model of stroke dose-dependently rescues behavioral deficits and reduces infarct volume," *Stroke*, 2004; 35:2390-2395.
Vendrame, M. et al., "Intravenous administration of human umbilical cord blood (HUCB) cells in a rat model of stroke: a dose dependent study," *Society for Neuroscience Abstract*, 2003; Presentation No. 844.11.
Verma, I. M. et al., "Gene Therapy—Promises, Problems and Prospects," *Nature*, 1997; 389:239-242.
Vermot-Desroches, C. et al., "Heterogeneity of Antigen Expressbn Among Human Umbilical Cord Vascular Endothelial Cells: Identification of Cell Subsets by Co-Expression of Haemopoietic Antigens," *Immunol. Lett.*, 1995; 48:1-9.
Villegas-Perez, M.P. et al., "Influences of Peripheral Nerve Grafts on the Survival and Regrowth of Axotomized Retinal Ganglion Cells in Adult Rats," *J. Neurosci.*, 1988; 8(1):265-280.
Villegas-Perez, M.P. et al., "Rapid and Protracted Phases of Retinal Ganglion Cell Loss Follow Axotomy in the Optic Nerve of Adult Rats," *J. Neurobiology*, 1993; 24(1):23-36.
Voeglin, et al., "Effects of local continuous release of brain derived neurotrophic factor (BDNF) on peripheral nerve regeneration in a rat model." *Exp. Neurol*, 2006: 199:348-353.
von Koskull, H. et al., "Inductbn of Cytokeratin Expression in Human Mesenchymal Cells," *J. Cell Physiol.*, 1987; 133:321-329.

Walboomers, X .F. et al., "Cell and Tissue Behavior on Micro-Grooved Surfaces," *Odontology*, 2001; 89:2-11.
Walter, D. H. et al., "Statin Therapy Accelerates Reendothelialization a Novel Effect Involving Mobilization and Incorporation of Bone Marrow-Derived Endothelial Progenitor Cells," *Circulation*, 2002; 105:3 017-3 024.
Wang, D. et al., "Synthesis and Characterization of a Novel Degradable Phosphate-Containing Hydrogel," *Biomaterials*, 2003; 24:3969-3980.
Wang, X. et al., "Cell Fusion Is the Principal Source of Bone-Marrow-Derived Hepatocytes," *Nature*, 2003; 422:897-900.
Wang, Y. et al., "Enhanced Recovery of Hematopoietic Progenitor and Stem Cells from Cultivated, Postpartum Human Placenta," *Blood*, 2001; 98(11): 183a (Abstract 769).
Wegman, A. et al., "Nonsteroidal Anti-Inflammatory Drugs or Acetaminophen for Osteoarthritis of the Hip or Knee? A Synstematic Review of Evidence and Guidelines," *J. Rheumatol.*, 2004; 31(2):344-354.
Weiss, M.L. et al., "Transplantation of Porcine Umbilical Cord Matrix Cells Into the Rat Brain," *Exp. Neur.*, 2003; 182:288-299.
Weiss, M.L. et al., "Human Umbilical Cord Matrix Stem Cells: Preliminary Characterization and Effect of Transplantation in a Rodent Model of Parkinson's Disease," *Stem Cells*, 2006; 24:781-792.
Wenning, G.K. et al., "Neural Transplantation in Animal Models of Multiple System Atrophy: A Review," *J. Nueral Transm.*, 1999; Suppl.(55):103-113.
Williams, J.T. et al., "Cells Isolated From Adult Human Skeletal Muscle Capable of Differentiating Into Multiple Mesodermal Phenotypes," *Am. Surg.* 1999; 65(1):22-6.
Winkler et al., "Lack of Long-Term Effects After Beta-Amyloid Protein Injections in Rat Brain," *Neurobiolo. Aging*, 1994; 15(5):601-607.
Wobus, A.M. et al., "Retinoic Acid Accelerates Embryonic Stem Cell-Derived Cardiac Differentiation and Enhances Development of Ventricular Cardiomyocytes," *J. Mol. Cell Cardiol.*, 1997; 29:1525-1539.
Wolford, L.M. et al., "Considerations in Nerve Repair," *BUMC Proceedings*, 2003; 16(2):152-156.
Woodbury, D., etal., "Adult Rat and Human Bone Marrow Stromal Cells Differentiate Into Neurons," *J. Neurosci. Res.*, 2000; 61:364-370.
Wulf, G.G. et al.,"Mesengenic Progenitor Cells Derived From Human Placenta," *Tissue Engineering*, 2004; 10(7/8):1136-1147.
Xi, G, et al., "Mechanisms of Edema Formation After Intracerebral Hemorrhage Effects of Extravasated Red Blood Cells on Blood Flow and Blood-Brain Barrier Integrity," *Stroke*, 2001; 32:2932-2938.
Xu, C. et al., "Characterization and Enrichment of Candbmyocytes Derived From Human Embryonic Stem Cells," *Circ. Res.*, 2002; 91:501-508.
Xu, Y. et al., "Dopamine, in the Presence of Tyrosinase, Covalently Modifies and Inactivates Tyrosine Hydroxylase," *J. Neurosci. Res.*, 1998; 54:691-697.
Yamashima, T., "Implication of Cysteine Proteases Calpain, Cathepsin and Caspase in Ischemic Neuronal Death of Primates," *Progress in Neurobiology*, 2000; 62:273-295.
Yang, C. et al., "Enhancement of Neovascularization With Cord Blood CD13 3+ Cell-Derived Endothelial Progenitor Cell Transplantation," *Thrombosis and Haemostasis*, 2004; 91:1202-1212.
Yang, D. et al.,"Therapeutic effect of human umbilical tissue-derived cell treated in Rats in experimental intracereberal hemorrhage", *Brain Research*, 2012; 1444:1-10.
Yang, H. et al.,"Region-Specific Differentiation of Neural Tube-Derived Neuronal Restricted Progenitor Cells After Heterotopic Transplantation," *PNAS*, 2000; 97(24):13366-13371.
Ye Q. et al., "Recovery of Placental-Derived Adherent Cells With Mesenchymal Stem Cell Characteristics", *Blood*, 2001; 98(11 Part 2):147B (Abstract No. 4260).
Yip, H.K., et al., "Axonal Regeneration of Retinal Ganglion Cells: Effect of Trophic Factors," *Prog. Retin Eye Res.*, 2000; 1 9(5):559-575.

(56) References Cited

OTHER PUBLICATIONS

Yokoo, T. et al.,"Stem Cell Gene Therapy for Chronic Renal Failure," *Curr Gene Ther.*, 2003; 3:387-394.
Yu, M. et al., "Mid-Trimester Fetal Blood-Derived Adherent Cells Share Characteristics Similar to Mesenchymal Stem Cells But Full-Term Umbilical Cord Blood Does Not," *British J. of Haematology*, 2004; 124:666-675.
Zangani, D. et al., "Multiple Differentiation Pathways of Rat Mammary Stromal Cells In Vitro: Acquisition of a Fibroblast, Adipocyte or Endothelial Phenotype Is Dependent on Hormonal and Extracellular Matrix Stimulation," *Differentiation*, 1999; 64:91-101.
Zhang, L. et al., "A Test for Detecting Long-Term Sensorimotor Dysfunction in the Mouse after Focal Cerebral lschemia," *J. Neurosci. Methods*, 2002; 117:207-214.
Zhang, S. et al.,"In Vitro Differentiation of Transplantable Neural Precursors From Human Embryonic Stem Cells," *Nature Biotechnology*, 2001; 19:1129-1133.
Zhang, X. et al.,"Efficient Adeno-Associated Virus-Mediated Gene Expression in Human Placenta-Derived Mesenchymal Cells," *Microbiol. Immunol.*, 2003; 47(1):109-116.
Zhang, Y. et al., "Comparison of Mesenchymal Stem Cells from Human Placenta and Bone Marrow," *Chinese Medical Journal*, 2004; 117(6):882-887.
Zhang, Z.G. et al., "Correlation of VEGF and Angiopoietin Expression with Disruption of Blood-Brain Barrier and Angiogenesis after Focal Cerebral lschemia," *J. Cereb. Blood Flow Metab.*, 2002; 22(4):379-392.
Zhang, Z.G. et al., "Magnetic resonance imaging and neurosphere therapy of stroke in rat," *Ann Neurol.*, 2003; 53(2):259-263.
Zimmerman, S. et al., "Lack of Telomerase Activity in Human Mesenchymal Stem Cells," *Leukemia*, 2003; 17:1146-1149.
Zuloff-Shani, A. et al., "Macrophage Suspensions Prepared From a Blood Unit for Treatment of Refractory Human Ulcers," *Transfus. Apheresis Sci.*, 2004; 30:163-167.
In the U.S. Patent and Trademark Office, Non-Final Office Action in re: U.S. Appl. No. 14/444,689 dated Mar. 24, 2015, 9 pages.
In the U.S. Patent and Trademark Office, Final Office Action in re: U.S. Appl. No. 11/317,574 dated Apr. 1, 2015, 12 pages.
In the U.S. Patent and Trademark Office, Final Office Action in re: U.S. Appl. No. 11/617,346 dated Apr. 15, 2015, 21 pages.
In the U.S. Patent and Trademark Office, Non-Final Office Action in re: U.S. Appl. No. 12/337,439 dated Mar. 5, 2015, 19 pages.
In the U.S. Patent and Trademark Office, Final Office Action in re: U.S. Appl. No. 13/111,933 dated Mar. 19, 2015, 25 pages.
In the U.S. Patent and Trademark Office, Non-Final Office Action in re: U.S. Appl. No. 12/642,774 dated Jun. 25, 2015 11 pages.
In the U.S. Patent and Trademark Office, Final Office Action in re: U.S. Appl. No. 13/471,095 dated Jun. 12, 2015, 10 pages.
In the U.S. Patent and Trademark Office, Final Office Action in re: U.S. Appl. No. 14/152,649 dated Jul. 10, 2015, 7 pages.
In the U.S. Patent and Trademark Office, Final Office Action in re: U.S. Appl. No. 13/111,933 dated Jul. 15, 2015, 31 pages.
In the U. S. Patent and Trademark Office, Final Office Action in re: U.S. Appl. No. 12/337,439 dated Jul. 16, 2015, 23 pages.
In the U.S. Patent and Trademark Office, Final Office Action in re: U.S. Appl. No. 11/617,346 dated Aug. 4, 2015, 18 pages.
In the U.S Patent and Trademark Office, Final Office Action in re: U.S. Appl. No. 12/339,872 dated Aug. 3, 2015, 14 pages.
In the U.S. Patent and Trademark Office, Non-Final Office Action in re: U.S. Appl. No. 12/642,775 dated Aug. 24, 2015, 38 pages.
In the U.S. Patent and Trademark Office, Non-Final Office Action in re: U.S. Appl. No. 10/877,446 dated Sep. 3, 2015, 82 pages.
In the U.S. Patent and Trademark Office, Non-Final Office Action in re: U.S. Appl. No. 11/321,864 dated Sep. 2, 2015, 11 pages.
In the U.S. Patent and T ademark Office Non-Final Office Action in re: U.S. Appl. No. 12/389,305 dated Sep. 4, 2015, 63 pages.
In the U.S. Patent and Trademark Office, Non-Final Office Action in re: U.S. Appl. No. 11/316,104 dated Sep. 8, 2015, 63 pages.
In the U.S. Patent and Trademark Office, Non-Final Office Action in re: U.S. Appl. No. 14/152,649 dated Oct. 27, 2015, 7 pages.
In the U.S. Patent and Trademark Office, Final Office Action in re: U.S. Appl. No. 10/876,998 dated Dec. 22, 2015, 21 pages.
In the U.S. Patent and Trademark Office, Final Office Action in re: U.S. Appl. No. 11/321,864 dated Dec. 22, 2015, 15 pages.
In the U.S. Patent and Trademark Office, Non-Final Office Action in re: U.S. Appl. No. 11/317,574 dated Jan. 6, 2015, 11 pages.
In the U.S. Patent and Trademark Office, Final Office Action in re: U.S. Appl. No. 11/322,372 dated Jan. 6, 2015, 27 pages.
In the U.S. Patent and Trademark Office, Non-Final Office Action in re: U.S. Appl. No. 13/471,095 dated Mar. 22, 2016, 17 pages.
In the U. S. Patent and Trademark Office, Final Office Action in re: U.S. Appl. No. 12/337,439 dated Mar. 17, 2016 29 pages.
In the U. S. Patent and Trademark Office, Final Office Action in re: U.S. Appl. No. 11/315,969 dated Apr. 21, 2016 20 pages.
In the U. S. Patent and Trademark Office, Non-Final Office Action in re: U.S. Appl. No. 14/705,680 dated May, 19, 2016 68 pages.
In the U. S. Patent and Trademark Office, Final Rejection in re: U.S. Appl. No. 10/876,998 dated May 20, 2016 21 pages.
In the U. S. Patent and Trademark Office, Final Office Action in re: U.S. Appl. No. 12/389,305 dated May 24, 2016 21 pages.
In the U. S. Patent and Trademark Office, Final Office Action in re: U.S. Appl. No. 11/316,104 dated May 24, 2016 24 pages.
In the U. S. Patent and Trademark Office, Non-Final Office Action in re: U.S. Appl. No. 10/877,446 dated May 24, 2016 36 pages.
In the U.S. Patent and Trademark Office, Non-Final Office Action in re: U.S. Appl. No. 11/322,372 dated May 31, 2016, 29 pages.
In the U.S. Patent and Trademark Office, Final Office Action in re: U.S. Appl. No. 11/317,574 dated May 31, 2016, 18 pages.
Baksh, D. et al., "Adult mesenchymal stem cells: characterization, differentiation, and application in cell and gene therapy", *J Cell Mol Med.*, 2004; 8(3):301-16.
Broxmeyer, H.E. et al.,"Growth characteristics and expansion of human umbilical cord blood and estimation of its potential for transplantation in adults," *PNAS*, 1992; 89(9): 4109-4113.
Chen, K. et al., "Human umbilical cord mesenchymal stem cells hUC-MSCs exert immunosuppressive activities through a PGE2-dependent mechanism," *Clinical Immunology*, 2010, 135; 448-458.
Kern, S. et al.,"Comparative analysis of mesenchymal stem cells from bone marrow, umbilical cord blood, or adipose tissue," *Stem Cells*, 2006; 24(5):1294-301.
Leventhal, C. et al. "Endothelial trophic support for neuronal production and recruitment from the adult mammalian subependyma," *Molecular and Cellular Neuroscience*, 1999; 13; 450-464.
Lu, L.L. et al., "Isolation and characterization of human umbilical cord mesenchymal stem cells with hematopoiesis-supportive function and other potentials," *Haematologica*, 2006;91(8):1017-26.
Mankikar, S.D., "Stem Cells: A New Paradigm in Medical Therapeutics," *Journal of Long-Term Effects of Medical Implants*, 2010; 20:219-250.
Otsuka, a. etal. "Lipopolysaccharide augments HLA-A,B,C molecule expression but inhibits interferon-gamma-induced HLA-DR molecule expression on cultured human endothelial cells," *Immunology*, 1991; 73; 428-432.
Xu, Y et al., "Umbilical Cord-Derived Mesenchymal Stem Cells Isolated by a Novel Explantation Technique Can Differentiate into Functional Endothelial Cells and Promote Revascularization," *Stem Cells and Development*, 2010, 19(10): 1511-1522.
Zhao, Q.H. et al., "Biological characteristics of human umbilical cord-derived mesenchymal stem cells and their differentiation into chondrogenic and osteogenic cells," *Zhonghua Yi Xue Za Zhi.*, 2011;91(5):317-21 (Abstract only).
In the U.S. Patent and Trademark Office, Final Office Action in re: U.S. Appl. No. 14/152,649 dated Jun. 14, 2016, 6 pages.
In the U.S. Patent and Trademark Office, Final Office Action in re: U.S. Appl. No. 11/317,574 dated Jul. 7, 2016, 9 pages.
Wakitani, S. et al., "Mesenchymal cell-based repair of large, full-thickness defects of articular cartilage", *J Bone Joint Surg Am*, 1994 ; 76(4): 579-592.
Weiss, M.L. et al., "Stem Cells in the Umbilical Cord," *Stem Cell Rev.*, 2006; 2(2):155-162.

* cited by examiner

HUTC AS THERAPY FOR ALZHEIMER'S DISEASE

CROSS-REFERENCE TO RELATED APPLICATIONS

This application is a divisional application of U.S. patent application Ser. No. 12/748,170, filed Mar. 26, 2010 (now U.S. Pat. No. 8,722,034, issued May 13, 2014), which claims benefit to U.S. Provisional Patent Application No. 61/163,619, filed Mar. 26, 2009, the contents of which are incorporated by reference in their entirety.

BACKGROUND

1. Field of the Invention

The present invention relates generally to compositions, methods and kits for treating Alzheimer's disease by administration of cells or cell derivatives. In particular, the invention provides administering cells or cell derivatives to a patient to reduce the accumulation of plaque proteins as well as provide support factors to reduce neuronal cell death. The invention also provides administering cells or cell derivatives to a patient to treat symptoms of Alzheimer's disease.

2. Description of Related Art

Alzheimer's disease is the most common cause of dementia in North America and Europe. Generally, Alzheimer's disease is a common and complex disorder characterized by adult-onset progressive dementia. The disease usually begins after age 65, and the risk of Alzheimer's disease increases with age. Indeed, approximately 10 percent of all persons over the age of 70 have significant memory loss and more than half of these individuals have Alzheimer's disease. The prevalence of dementia in individuals over the age of 85 is estimated to be about 25-45%. Further, Alzheimer's disease is believed to be the fourth leading cause of death in elderly adults.

A record number of people are becoming elderly in the next few decades. Unless effective methods for prevention and treatment are developed by the pharmaceutical and medical industries, Alzheimer's disease may reach epidemic proportions by the middle of the next century. Because of increasing longevity, the occurrence of Alzheimer's disease in the elderly presents a tremendous medical, economic and social problem facing the health care industry today.

Alzheimer's disease is a degenerative disease of the brain from which there is no recovery. The disease attacks nerve cells in all parts of the cortex of the brain, as well as some of the surrounding structures and tissues. Typically, Alzheimer's disease begins with subtle and poorly recognized failure of memory. The early symptoms of Alzheimer's disease may be overlooked because such symptoms resemble signs of natural aging. These symptoms include forgetfulness, loss of concentration, unexplained weight loss and motor problems, including mild difficulties in walking. In healthy individuals, similar symptoms can result from fatigue, grief or depression, illness, vision or hearing loss, the use of alcohol with certain medications, or simply the inability to remember complex details at one time. Accompanying sensory problems, such as hearing loss and a decline in reading ability, as well as general physical debility indicate a short survival time. Other symptoms include confusion, poor judgment, language disturbance, agitation, withdrawal, and hallucinations. Some patients may develop seizures, Parkinsonian-type features, decreased muscle tone, myoclonus, incontinence and mutism. The patient may also exhibit symptoms such as inability to perform routine tasks, loss of language skills, inability to plan, and personality changes. Over time, these changes become so severe and impairing that the patient loses all memory and mental functioning to the point of complete central nervous system (CNS) collapse and cessation of regulated circulatory and respiratory function.

Clinically, Alzheimer's disease is a neuropathological disease. Recognized clinical signs include progressive dementia and cerebral cortical atrophy, which can be established by neuroimaging studies. In addition, neuropathological findings usually include microscopic A-beta amyloid neuritic plaques, intraneuronal neurofibrillary tangles and amyloid angiopathy. Studies indicate that Alzheimer's disease is associated with cerebral cortical atrophy, histological findings of beta amyloid plaques and findings of intraneuronal neurofibrillary tangles within the cortical regions of the brain.

Neurofibrillary tangles are tangled fibers, which are the damaged remains of microtubules, within the cortical region of the brain, that support the structure allowing the flow of nutrients through nerve cells (neurons). Beta amyloid is an insoluble protein which is a fragment of a larger protein (APP). APP itself appears to be important in nerve protection. Should the enzyme involved in cutting APP into fragments of beta amyloid fail to function, APP has been shown to form sticky patches called neuritic plaques, which decrease neuronal function and signal transmission within the brain. Generally, such neuritic plaques are found on the outside of nerve cells surrounded by debris of dying neurons.

In addition, high levels of beta amyloid are associated with reduced levels of the neurotransmitter acetylcholine. Neurotransmitters are chemical messengers in the brain that transmit various signals, messages, and neurochemical information within the various regions of the CNS. Acetylcholine is part of the cholinergic system, which is essential for memory and learning, and is progressively destroyed in patients suffering from Alzheimer's disease. Thus, it is theorized that beta amyloid in the form of neuritic plaques causes a decrease in the neurotransmitter, acetylcholine, leading to progression of Alzheimer's disease.

Currently, Alzheimer's disease treatment is based on managing disease symptomology for each individual's disease progression. Although there are drugs for treating Alzheimer's disease, there is no cure for the disease. Treatments include drugs that alter neurotransmitter availability in the CNS. For instance, some drugs increase acetylcholine in the brain, such as acetylcholinesterase inhibitors, work as dopamine receptor antagonist, and noncompetitive NMDA receptor antagonists. Other drugs are used to treat the aggression and psychosis of Alzheimer's patients.

Currently available treatments have side effects, including nausea, diarrhea, hepatotoxicity, abdominal cramping, ulcers, gastrointestinal bleeding, orthostatic hypotension, drowsiness, dizziness, sexual dysfunction, and insomnia. At times, the side effects are so severe that the physician ceases treatment.

Given the current limitations in treating Alzheimer's disease, there exists a need for alleviating Alzheimer's disease symptoms in individuals that is cost effective, has minimal potential for side effects, and positively increases memory, cognitive function, and ability to perform daily living activities.

SUMMARY OF THE INVENTION

Figure 1:
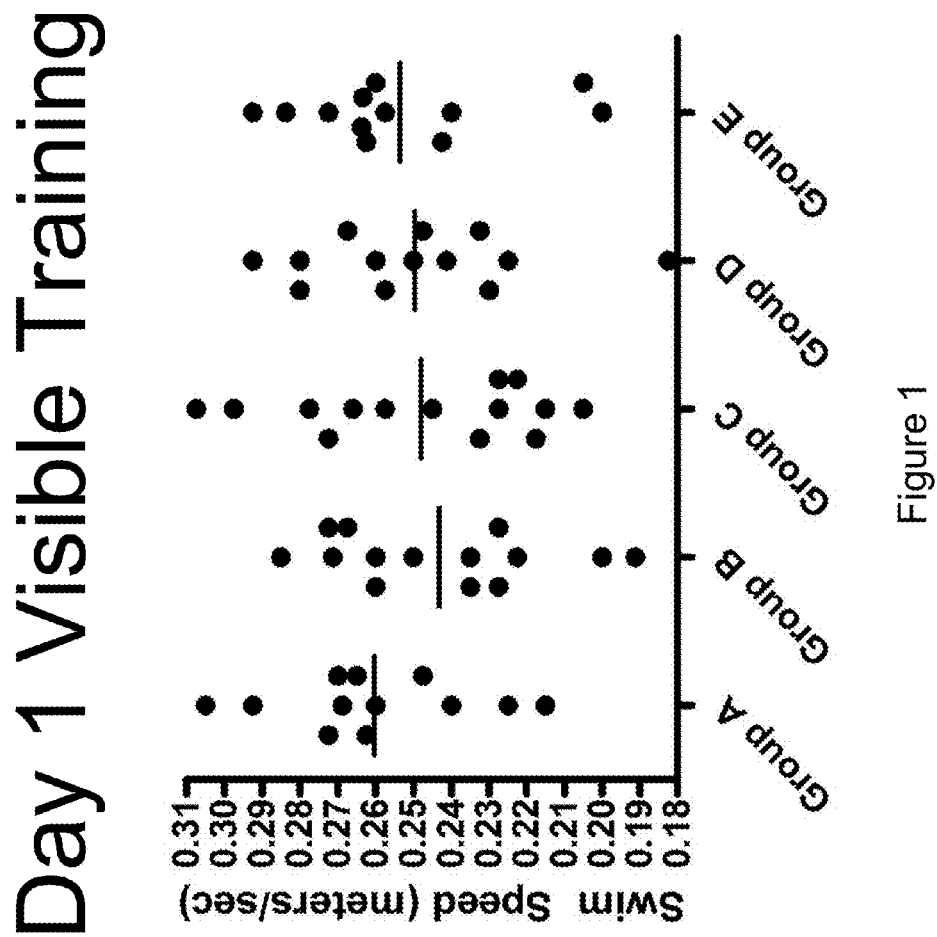
FIG. 1 shows the results of Morris Water Maze testing across all treatment groups for one day in a visible platform test evaluated by swim speed.

The problems presented are solved by the compositions, methods and kits of the illustrative embodiments described herein. These embodiments provide methods for treating Alzheimer's disease, or the symptoms of Alzheimer's disease, by administering a cell, population of cells or cell derivatives. While not wishing to be bound by any mechanism of action, the inventors believe that cells or cell derivatives administered to an Alzheimer's patient reduce the prevalence of the plaque, not only reducing senile plaque progression, but also increasing neuroprotection. Further, the inventors believe that administration of the cell or cell derivatives facilitates plaque removal by a phagocytic mechanism. The present invention is based, at least in part, on the discovery that cells, including stem cells and/or postpartum-derived cells derived from human placental or umbilical cord tissue ("hUTC"), can be administered locally or systemically to a patient with Alzheimer's disease. In particular, the present invention relates to administration of hUTC or hUTC derivatives to patients with Alzheimer's disease.

Specific embodiments of the invention are directed to the treatment of the signs/symptoms of Alzheimer's disease, including forgetfulness, loss of concentration, unexplained weight loss and motor problems, difficulties in walking, hearing loss, decline in reading or linguistic ability, confusion, poor judgment, agitation, withdrawal, hallucinations, seizures, Parkinsonian-type features, decreased muscle tone, myoclonus, incontinence, mutism, inability to perform routine tasks, inability to plan, and personality changes.

In one embodiment, the invention pertains to a method of treating a subject having Alzheimer's disease by administering a population of cells in an amount effective, such that the Alzheimer's disease is treated. In another embodiment, the cells administered are postpartum-derived cells. In some embodiments, the postpartum-derived cells are derived from human placental, and in other embodiments the postpartum-derived cells are derived from umbilical cord tissue. In another embodiment, the cells administered are stem cells. In one embodiment, the cells are hUTC.

In another embodiment, the invention pertains to a method of treating a subject having signs and/or symptoms of Alzheimer's disease by administering a population of cells in an amount effective, such that the signs and/or symptoms of Alzheimer's disease are treated. In another embodiment, the cells administered are postpartum-derived cells. In some embodiments, the postpartum-derived cells are derived from human placental, and in other embodiments the postpartum-derived cells are derived from umbilical cord tissue. In another embodiment, the cells administered are stem cells. In one embodiment, the cells are hUTC.

In some embodiments, the population of cells is administered in a single injection. In other embodiments, the population of cells is administered in more than one injection. In one embodiment, the cells are administered to the CNS via cerebral spinal fluid (CSF). In another embodiment, the cells are administered locally to the CNS at the area of plaque formation. In another embodiment, the cells are administered locally to a region of brain involved in memory and learning, including but not limited to, amygdale, striatum, mammillary bodies such as the hippocampus and diencephalons, temporal cortex, thalamus, hypothalamus, peripheral cortex, and neocortex.

The administration site may be any that is determined by the medical professional to be best effective, and thus may be at, proximal, or distal to the site of plaque formation.

The cell administration may be by any means, including but not limited to, into the CSF, cerebral tissue, and the like. The delivery may also occur by syringes with needles and/or catheters with or without pump devices. The delivery may include use of pharmaceutically acceptable carriers such as saline, collagen, cross-linked collagen, hyaluronic acid, synthetic polymer based systems, liquids, hydrogels, or scaffolds. In addition, some embodiments include use of one or more growth factors injected in parallel, sequentially, or formulated directly into one or more pharmaceutically acceptable carriers.

In some embodiments, the population of cells is administered with at least one other agent, including but not limited to, selected extracellular matrix components, microcarriers, microparticulate systems including anti-apoptotic agents, anti-inflammatory compounds, immunosuppressive or immunomodulatory agents, anti-oxidants, and other factors to enhance cell survival, proliferation and other cell functions. In one embodiment, the composition further comprises at least one of the agents or factors selected from the group consisting of neurotrophic factors.

In some embodiments, the cells are pre-treated with electrical stimulation prior to administration.

In other embodiments, the cells are modified to express one or more genes that enhance neural cell survival, differentiation or phagocytic activity of the cells.

In all embodiments, cell derivatives such as lysate or conditioned media, may be co-administered with, or administered instead of, the instant population of cells.

Other embodiments of the invention feature compositions and kits for treating a patient with Alzheimer's disease comprising at least a population of cells and a pharmaceutically acceptable carrier. Other composition and kit embodiments may include other agents, growth factors, and compounds such as anti-apoptotic agents, anti-inflammatory compounds, immunosuppressive or immunomodulatory agents, anti-oxidants, and other factors to enhance cell survival, proliferation and other cell functions. The pharmaceutical compositions and kits are designed and/or formulated for practicing the methods of the invention as outlined above and below.

Other objects, features, and advantages of the illustrative embodiments will become apparent with reference to the drawings and detailed description that follow.

DETAILED DESCRIPTION OF THE INVENTION

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

To better clarify the invention, the following definitions are provided.

The terms "plaque site," "neuritic plaque," "neural injury" and "site of neural damage" as used herein are interchangable and generally refer to an area of the central nervous system where amyloid plaques have accumulated on or adjacent to neural tissue of an individual, and may include but not limited to, connective tissue and vascular tissue. The terms may further refer to areas of any tissue that are not necessarily wounded or defected, but are instead areas in which it is desired to reduce growth of plaques. The term may also refer to nervous tissue that while having no apparent plaque formation, clinical observations, prior research or current individual patient's indicate the presence of an abnormality in neural tissue function, as observed by alternations in memory, learning, motor function, audiovisual function, linguistics function, and the like.

The terms "individual," "patient" or "subject" as used herein generally refer to any form of animal, including mammals, such as humans and monkeys, who are treated with the pharmaceutical or therapeutic compositions or in accordance with the methods described. The term "xenogeneic" as used herein refers to administration or administration of cells from a donor of one species into a subject of a different species.

The terms "treat," "treating" or "treatment" as used herein generally refer to amelioration or reduction in any symptom of Alzheimer's disease, reduction in plaque formation, and diminishing of plaques, for a period of time following administration of a population of cells into a subject suffering from Alzheimer's disease. The amelioration or reduction also includes any objective or subjective parameter such as abatement, remission, diminishing of symptoms or making the Alzheimer's disease more tolerable to the patient, slowing in the rate of degeneration or decline, making the final point of degeneration less debilitating, improving a subject's physical or mental well-being, or prolonging the length of survival. The treatment or amelioration of symptoms can be based on objective or subjective parameters; including the results of a physical examination or neurological examination The terms "effective period," "effective period of time" or "effective conditions" refer generally to a period of time or other controllable conditions (e.g., temperature, humidity for in vitro methods), necessary or preferred for an agent or pharmaceutical composition to achieve its intended result.

The term "effective amount" as used herein generally refers to a concentration or amount of a compound, material, or composition, as described herein, that is effective to achieve a particular biological result. Such results include, but are not limited to, the improvement of, and/or decrease in symptoms of, Alzheimer's disease for a patient. Such effective activity may be achieved, for example, by administering the cells and/or compositions of the present invention to patients with Alzheimer's disease. With respect to the population of cells as administered to a patient, an effective amount may range from 300,000 to 2 million cell/kg local administration and 0.16 million cell/kg-10 million cell/kg when delivered systemically. It is appreciated that the number of cells administered will vary depending on the specifics of the area of treatment, including but not limited to, the size or total volume/surface area to be treated, and proximity of the site of administration to the location of the region to be treated, method of delivery, i.e., such as delivery to the CSF versus intra-neural treatment, and the like.

The term "stem cell" as used herein generally refers to undifferentiated cells defined by the ability of a single cell both to self-renew, and to differentiate to produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following administration, and to contribute substantially to most, if not all, tissues following injection into blastocysts. The stem cells may come from any source, including but not limited to, embryonic and fetal sources, postpartum tissues such as the umbilical cord and placenta, and adipose cells. Stem cells can be classified according to their developmental potential as totipotent, pluripotent, multipotent, oligopotent and unipotent. Stem cells can also be categorized based on the source from which they are obtained, and include adult stem cells, embryonic stem cells, fetal stem cells and postpartum stem cells.

As used here, the term "embryonic tissue" generally refers to a tissue originating from the embryo (which in humans refers to the period from fertilization to about six weeks of development). Further the term "fetal tissue" refers to tissue originating from the fetus, which in humans refers to the period from about six weeks of development to parturition and "extraembryonic tissue" refers to tissue associated with, but not originating from, the embryo or fetus. Extraembryonic tissues include extraembryonic membranes (chorion, amnion, yolk sac and allantois), umbilical cord and placenta (which itself forms from the chorion and the maternal decidua basalis).

As used herein the phrase "neural cell" includes both nerve cells (i.e., neurons, e.g., uni-, bi-, or multipolar neurons) and their precursors and glial cells (e.g., macroglia such as oligodendrocytes, Schwann cells, and astrocytes, or microglia) and their precursors.

The term "progenitor cell" as used herein generally refers to a cell with the capacity to create progeny that are more differentiated than it, and yet retains the capacity to replenish the pool of progenitors. By that definition, stem cells themselves are also progenitor cells, as are the more immediate precursors to terminally differentiated cells. When referring to the cells of the present invention, as described in greater detail below, this broad definition of "progenitor cells" may be used. In a narrower sense, a progenitor cell is often defined as a cell that is intermediate in the differentiation pathway, i.e., it arises from a stem cell and is intermediate in the production of a mature cell type or subset of cell types. This type of progenitor cell is generally not able to self-renew. Accordingly, if this type of cell is referred to herein, it will be referred to as a "non-renewing progenitor cell" or as an "intermediate progenitor or precursor cell."

As used herein, the phrase "differentiation" generally means the process by which an unspecialized ("uncommitted") or less specialized cell acquires the features of a specialized cell, such as a nerve cell or a muscle cell, for example. A differentiated cell is one that has taken on a more specialized ("committed") position within the lineage of a cell. The term committed, when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. De-differentiation refers to the process by which a cell reverts to a less specialized (or committed) position within the lineage of a cell. As used herein, the lineage of a cell defines the heredity of the cell, i.e. which cells it came from and what cells it can give rise to. The lineage of a cell places the cell within a hereditary scheme of development and differentiation.

The cells used in the present invention may include what is termed "postpartum cells" or "postpartum-derived cells." These cells may be umbilicus-derived cells or placenta-derived cells. In addition, the cells may be described as being stem or progenitor cells, the latter term being used in the broad sense. The term "derived" is used to indicate that the cells have been obtained from their biological source and grown or otherwise manipulated in vitro (e.g., cultured in a growth medium to expand the population and/or to produce a cell line). The in vitro manipulations of umbilical stem cells and the unique features of the umbilicus-derived cells of the present invention are described in detail below. Further, "hUTC" as used herein generally refers to human umbilical cord derived cells, and is the same as human umbilical tissue derived cells.

A "population" or "population of cells" generally refers to two or more cells. A population of cells can be obtained from the same or different source(s), e.g., the same donor or several different donors. Moreover, the cells in a population are not necessarily of the same cell type. A population of cells can include a mixture of, for example, both umbilical-derived and placenta-derived cells.

The term "isolate" as used herein generally refers to a cell which has been separated from its natural environment. This term includes gross physical separation from its natural environment, e.g., removal from the donor animal. In preferred embodiments, an isolated cell is not present in a tissue, i.e., the cell is separated or dissociated from the neighboring cells with which it is normally in contact. Preferably, cells are administered as a cell suspension. As used herein, the phrase "cell suspension" includes cells which have been dissociated, e.g., by subjecting a piece of tissue to gentle tritration, which are in contact with a medium.

As used herein, the term "growth medium" generally refers to a medium sufficient for the culturing of postpartum-derived cells. In particular, one medium for the culturing of the cells of the invention comprises Dulbecco's Modified Essential Media (DMEM). Particularly preferred is DMEM-low glucose (DMEM-LG) (Invitrogen, Carlsbad, Calif.). The DMEM-LG is preferably supplemented with serum, most preferably fetal bovine serum or human serum. Typically, 15% (v/v) fetal bovine serum (e.g. defined fetal bovine serum, Hyclone, Logan Utah) is added, along with antibiotics/antimycotics (preferably 100 Unit/milliliter penicillin, 100 milligrams/milliliter streptomycin, and 0.25 microgram/milliliter amphotericin B; Invitrogen, Carlsbad, Calif.), and 0.001% (v/v) 2-mercaptoethanol (Sigma, St. Louis Mo.). In some cases different growth media are used, or different supplementations are provided, and these are normally indicated in the text as supplementations to growth medium. In certain chemically-defined media the cells may be grown without serum present at all. In such cases, the cells may require certain growth factors, which can be added to the medium to support and sustain the cells. Presently preferred factors to be added for growth on serum-free media include one or more of bFGF, EGF, IGF-I, and PDGF. In more preferred embodiments, two, three or all four of the factors are add to serum free or chemically defined media. In other embodiments, LIF is added to serum-free medium to support or improve growth of the cells.

A "cell derivative" refers to conditioned medium or cell lysate.

A "conditioned medium" is a medium in which a specific cell or population of cells has been cultured, and then removed. When cells are cultured in a medium, they may secrete cellular factors that can provide trophic support to other cells. Such trophic factors include, but are not limited to hormones, cytokines, extracellular matrix (ECM), proteins, vesicles, antibodies, and granules. The medium containing the cellular factors is the conditioned medium.

The term "primary cell culture" is a culture of cells, tissues, or organs taken directly from an organism(s) before the first subculture.

The term "cell line" generally refers to a population of cells formed by one or more subcultivations of a primary cell culture. Each round of subculturing is referred to as a passage. When cells are subcultured, they are referred to as having been "passaged." A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore, the number of population doublings of a culture may be greater than the passage number. The expansion of cells (i.e., the number of population doublings) during the period between passaging depends on many factors, including but not limited to the seeding density, substrate, medium, growth conditions, and time between passaging.

The terms "pharmaceutically acceptable carrier" or "pharmaceutically acceptable medium" as used herein generally refers to reagents, cells, compounds, materials, compositions, and/or dosage forms that are not only compatible with the cells and other agents to be administered therapeutically, but also are, within the scope of sound medical judgment, suitable for use in contact with the tissues of human beings and animals without excessive toxicity, irritation, allergic response, or other complication commensurate with a reasonable benefit/risk ratio.

As described in greater detail herein, pharmaceutically acceptable carriers suitable for use in the present invention include liquids, semi-solid (e.g., gels) and solid materials (e.g., cell scaffolds and matrices, tubes sheets and other such materials as known in the art and described in greater detail herein). These semi-solid and solid materials may be designed to resist degradation within the body (non-biodegradable) or they may be designed to degrade within the body (biodegradable, bioerodable). A biodegradable material may further be bioresorbable or bioabsorbable, i.e., it may be dissolved and absorbed into bodily fluids (water-soluble implants are one example), or degraded and ultimately eliminated from the body, either by conversion into other materials or breakdown and elimination through natural pathways. The biodegradation rate can vary according to the desired release rate once implanted in the body.

The term "matrix" as used herein generally refers to a mixture of biodegradable and/or bioresorbable materials that are administrated with the cells to a patient. In one embodiment, the matrix provides for sustained release of neurotrophic factors or other agents used in conjunction with the cells and may provide a structure for developing tissue growth in the patient. In other embodiments, the matrix simply provides a temporary scaffold for the developing tissue. The matrix can be in particulate form (macroparticles greater than 10 microns in diameter or microparticles less than 10 microns in diameter), or can be in the form of a structurally stable, three-dimensional implant (e.g., a scaffold). The matrix can be a slurry or hydrogel, or alternatively, can be a three dimensional structure.

The term "scaffold" as used herein generally refers to a three dimensional porous structure that provides a template for cell growth. A scaffold is made of biodegradable and/or bioresorbable materials that degrade over time within the body. The length of time taken for the scaffold to degrade may depend upon the molecular weight of the materials. Thus, higher molecular weight material may result in polymer scaffold which retain their structural integrity for longer periods of time; while lower molecular weights result in both slower release and shorter scaffold lives. The scaffold may be made by any means known in the art. Examples of polymers which can be used to form the scaffold include natural and synthetic polymers. In some embodiments of the invention, the scaffold may be infused with, coated with, or comprised of a population of cells, growth factors, or other nutrients to promote cell growth. In some preferred embodiments, the scaffold contains growth inducing agents including neurotrophins. Further, the growth inducing agents may be synthetic or naturally produced, and may be a fragment, derivative or analog of a growth inducing agent.

"Neurotrophic factor" or "trophic factor" is defined as a substance that promotes survival, growth, proliferation and/or maturation of a cell, or stimulates increased activity of a cell.

SPECIFIC EMBODIMENTS

For all embodiments of the invention, an individual diagnosed with Alzheimer's disease, or exhibiting symptoms of Alzheimer's disease, is administered a population of cells in an amount effective to treat the Alzheimer's disease, or its symptoms. Specific embodiments of the invention are directed to local administration of a population of cells to facilitate plaque removal by phagocytic mechanisms and/or active endogenous mechanisms to reduce the progression of plaque formation, and stimulate and support neural tissue growth and/or healing. The cells may be any discussed below, including stem cells, postpartum-derived cells, umbilical-derived or placenta-derived cells. In one embodiment, the cells are hUTC. A more detailed explanation of preferred cells is described in the below specification. Some embodiments are to compositions administered to the individual, where the composition includes a population of cells, and a pharmaceutically acceptable carrier. Such compositions can be used in kits for making, using, and practicing such methods and pharmaceutical compositions as described and exemplified herein. The kits can further contain devices to help facilitate administration of the population of cells, such as, for example, needles, tubes, micropipette, and the like. In one embodiment, the kit comprises at least one population of cells, a construct, and an injection device.

Further, in some embodiments, the kits can also be coupled with imaging devices that indicate the exact placement of the cells.

In one embodiment, the population of cells is administered to an individual diagnosed with Alzheimer's disease, where the administration is to an area of known plaque formation in the CNS. The Alzheimer's disease may be diagnosed by any means known in the art, including measurement of amyloid beta and tau, or its precursors, fragments, or metabolic compounds in CSF. Alzheimer's may also be diagnosed by measurement of isoprosanes in the individual's fluids, including urine and blood. Other diagnostic methods may include use of brain imaging techniques, for example, magnetic resonance imaging (MRI) to examine brain atrophy, positron emission topography (PET) to image the plaques and tangles of Alzheimer's Disease, and functional MRI (fMRI) to measure oxygen levels in the blood in the hippocampus or other memory and/or learning areas of the brain.

The exact type of cells that make up the population of cells administered is dependent upon the discretion of the medical professional. In one embodiment, the cells administered are postpartum-derived cells. In some embodiments, the postpartum-derived cells are derived from human placental tissue, and in other embodiments the postpartum-derived cells are derived from umbilical cord tissue. In another embodiment, the cells administered are stem cells. In one preferred embodiment, the cells are hUTC. A detailed description of the types of cells suitable for this invention is described below.

The population of cells may administered at, proximal, or distal to an area of the brain where plaques have accumulated on, or adjacent to, neural tissue of an individual. Such areas of the brain may include any involved in memory and learning, including but not limited to, amygdale, straitum, mammillary bodies such as the hippocampus and diencephalons, temporal cortex, thalamus, hypothalamus, peripheral cortex, and neocortex. The exact administration site may be any that is determined by the medical professional to be best effective. In another embodiment, the population of cells is administered directly to the CSF.

The cell administration may be administered by any means determined by the medical professional to be most effective, and can include use of a catheter, syringe, shunt, stent, microcatheter, pump, implantation with a device, or implantation with a scaffold. Further, the cell administration may be by intranasal delivery, intravascular delivery, intracerebral injection and intraventricular injection. In one embodiment, the population of cells may only be administered in only one injection. In some embodiments, the population of cells is administered more in more than one injection. In yet another embodiment, a pump is used to ensure slow, continuous administration of the population of cells.

Pharmaceutical compositions comprising the population of cells can be formulated as liquids, semisolids (e.g., gels) or solids (e.g., matrices, scaffolds and the like). Liquid compositions are formulated for administration by any acceptable route known in the art to achieve delivery of the population of cells to the target neural tissues. Typically, these include injection or infusion, either in a diffuse fashion, or targeted to the site of neurotic plaque formation. For instance, in one embodiment, the population of cells is administered by direct stereotaxic injection, e.g., needle. The needle may be any size to facilitate movement of cells through the hollow bore. The needle may be inserted directly through a bore in the skull, through the neural tissue of the brain to the neural site of interest, or alternatively the needle may be used with a device to ease guidance of the needle to the tissue site, such as, for example, a guide wire. The needle and guidance device can be either preassembled or delivered to the trained practitioner, the trained practitioner may assemble the device himself just prior to or during use.

In an alternate embodiment, a delivery catheter may be used to deliver the population of cells can be inserted into a delivery device which facilitates introduction by e.g., injection, of the cells into the subjects. Such delivery devices include tubes, e.g., catheters, for injecting cells and fluids into the body of a recipient subject. In one embodiment, the cells of the invention can be introduced into the subject at a desired location using a micropipette. The cells of the invention can be inserted into such a delivery device, e.g., a micropipette or syringe, in the form of a solution, e.g., a cell suspension. In addition, the cells of the invention can be administered in a guidance channel (e.g., polyacrylonitrile/polyvinylchloride (PAN/PVC) guidance channels), such as those described in Bunge et al., J Neurology, 1994; 241: S19-S21.

The population of cells or compositions and/or matrices comprising the cells may be delivered to the site via a micro catheter, intracatheterization, or via a mini-pump. The vehicle excipient or carrier can be any of those known to be pharmaceutically acceptable for administration to a patient, particularly locally at the site at which cellular differentiation is to be induced.

Conditioned Media and Cell Lysates

In one embodiment, conditioned media is administered to the individual in addition to, or instead of cells. In another embodiment, cell lysate is administered to the individual in addition to, or instead of cells. In yet another embodiment, conditioned media and cell lysate are administered to the individual in addition to, or instead of cells.

Conditioned medium from cultured PPDCs may be used in vitro and in vivo. Use of the PPDC or other conditioned medium may allow the beneficial trophic factors secreted by the PPDCs to be used allogeneically in a patient without introducing intact cells that could trigger rejection, or other adverse immunological responses. Conditioned medium is prepared by culturing cells in a culture medium, then removing the cells from the medium.

Conditioned medium prepared from population of postpartum-derived cells may be used as is, further concentrated, for example, by ultrafiltration or lyophilization, or even dried, partially purified, combined with pharmaceutically-acceptable carriers or diluents as are known in the art, or combined with other compounds such as biologicals, for example pharmaceutically useful protein compositions. Conditioned medium may be used in vitro or in vivo, alone or combined with autologous or syngeneic live cells, for example. The conditioned medium, if introduced in vivo, may be introduced locally at a site of treatment, or remotely to provide needed cellular growth or trophic factors to a patient.

According to embodiments of the present invention, a stable and scalable process is provided to manufacture reduced serum hUTC-conditioned media. Briefly, the method includes the culture of hUTC under reduced serum conditions. Subsequently the hUTC are washed and grown in serum-free basal media. After approximately 24 hours, the conditioned media is collected, filtered and concentrated by use of an approximately 5 kDa or similar molecular weight cut-off membrane.

Human umbilical tissue-derived cells (hUTC) may be isolated by following the methods described in U.S. Patent Publication Nos. 2005/0054098 and 2005/0058631, which are incorporated by reference in their entirety. The isolated cells may then be grown in static culture by following the methods as described in U.S. Patent Publication Nos. 2005/0054098 and 2005/0058631 until the time at which the conditioned media is prepared.

The conditioned media may be prepared at any population doubling of the cells. In another embodiment, the conditioned media is prepared from about population doubling population doubling 20 to about population doubling 44. In yet another embodiment, conditioned media is prepared at about population doubling 30.

The conditioned media is prepared by first isolating the cells from a standard culture media that cells were grown in. Cells are then seeded in static culture at any seeding density. In one embodiment the cells are seeded at a density of from about 1,000 cells per cm squared to about 10,000 cells per cm squared. In yet another embodiment, the cells were seeded at a density of about 5,000 cells per cm squared.

Following cell seeding, at approximately 5,000 cells/cm$^2$, the cells are weaned from the standard culture media having a bovine serum content of about 15% by reducing the bovine serum content in the media in increments until the cells are grown only in basal media. The bovine serum may be reduced in increments of about 5 to about 60%. In one embodiment, the bovine serum is reduced in increments of about 50% (i.e., 15%, 7.5%, 3.25%, and 0% bovine serum in the media). The cells are allowed to grow in each reduced serum media for about 1 to about 3 passages. In one embodiment, the cells are grown in each reduced serum media for about 2 passages. Prior to adding the final reduced bovine serum media, the cells are seeded at approximately 10,000 cells/cm$^2$. When the basal media (0% bovine serum) is added to the cells, the cells are kept in the media for no more than 24 hours.

The conditioned media is then isolated from the cells and filtered using an approximately 0.22 micron or similar filter. The filter may or may not be sterilized. The filtered conditioned media is then concentrated using an approximately 5K cut off filter or similar device. The filtrate is discarded while the concentrated conditioned media retained on the filter is collected.

In another embodiment, the isolated hUTC are grown in microcarrier bead culture following the methods as described in U.S. Patent Publication No. 2008/0166328, which is incorporated by reference in its entirety (See Examples) until the time at which the conditioned media is prepared.

The conditioned media may be prepared at any population doubling of the cells. In another embodiment, the conditioned media is prepared from about population doubling 20 to about population doubling 44. In yet another embodiment, conditioned media is prepared at about population doubling 30.

Following cell seeding, at approximately 10,000 cells/cm$^2$ in microcarrier bead culture, the standard culture media is added to the cells and cultured for about 2 days. Subsequently, the standard culture media is removed and replaced with basal media. Alternately, the microcarrier bead culture may be weaned from the standard culture media similarly to the static culture. When the basal media (0% bovine serum) is added to the cells, the cells are kept in the media for no more than 24 hours.

The conditioned media is then isolated from the cells and filtered using an approximately 0.22 micron or similar filter. The filter may or may not be sterilized. The filtered conditioned media is then concentrated using an approximately 5K cut off filter or similar device. The filtrate is discarded while the concentrated conditioned media retained on the filter is collected.

Conventional conditioned media, although rich in proteins from the cultured cell type is also rich in proteins from the bovine serum present in the media. The conditioned media prepared by the methods described above is concentrated in human proteins. The bovine proteins are present in an amount that is below detection of standard characterization methods, such as SDS-PAGE and Western Blot analysis. The below-detection amounts of bovine protein in the conditioned media are advantageous due to the subsequent reduced risk for transmission of bovine diseases and virus as well as reduced risk for xenoimmune reaction.

Cell lysates may be prepared by any means known to the practitioner. In one embodiment, whole cell lysates are prepared, e.g., by disrupting cells without subsequent separation of cell fractions. In another embodiment, a cell membrane fraction is separated from a soluble fraction of the cells by routine methods known in the art, e.g., centrifugation, filtration, or similar methods. Use of soluble cell fractions in vivo allows the beneficial intracellular milieu to be used in a patient without triggering rejection or an adverse response. Methods of lysing cells are well-known in the art and include various means of freeze-thaw disruption, osmotic disruption, mechanical disruption, enzymatic disruption (e.g., hyaluronidase, dispase, proteases, and nucleases (for example, deoxyribonuclease and ribonuclease)), or chemical disruption (non-ionic detergents such as, for example, alkylaryl polyether alcohol (TRITON® X-100), octylphenoxy polyethoxy-ethanol (Rohm and Haas Philadelphia, Pa.), BRIJ-35, a polyethoxyethanol lauryl ether (Atlas Chemical Co., San Diego, Calif.), polysorbate 20 (TWEEN 20®), a polyethoxyethanol sorbitan monolaureate (Rohm and Haas), polyethylene lauryl ether (Rohm and Haas); and ionic detergents such as, for example, sodium dodecyl sulphate, sulfated higher aliphatic alcohols, sulfonated alkanes and sulfonated alkylarenes containing 7 to 22 carbon atoms in a branched or unbranched chain), or combinations thereof. Such cell lysates may be prepared from cells directly in their growth medium and thus containing secreted growth factors and the like, or may be prepared from cells washed free of medium in, for example, PBS or other solution. Washed cells may be resuspended at concentrations greater than the original population density if preferred. Cell lysates prepared from populations of postpartum-derived cells may be used as is, further concentrated, by for example, ultrafiltration or lyophilization, or even dried, partially purified, combined with pharmaceutically acceptable carriers or diluents as are known in the art, or combined with other compounds such as biologicals, for example pharmaceutically useful protein compositions. In some embodiments, cellular membranes are removed from the lysate, for example by centrifugation, to yield a membrane fraction and supernate fraction. The membrane fraction or the supernate may be used according to the methods of the invention. In some embodiments, cellular debris is removed by treatment with a mild detergent rinse, such as EDTA, CHAPS or a zwitterionic detergent. Cell lysates may be used in vitro or in vivo, alone or, for example, with cells. The cell lysates, if introduced in vivo, may be introduced locally at a site of treatment, or remotely to provide, for example needed cellular growth factors to a patient.

The amounts and/or ratios of proteins may be adjusted by mixing the PPDC product of the invention with cells or with ECM or cell fraction of one or more other cell types. In addition, biologically active substances such as proteins, growth factors and/or drugs, can be incorporated into the PPDC product formulation. Exemplary biologically active substances include anti-inflammatory agents and growth factors which promote healing and tissue repair. Cells may be co-administered with the PPDC products of the invention.

The above described process for preparing PPDC products is preferably carried out under sterile conditions using sterile materials.

Agents or Compounds Administered

The cells or cell derivatives of the present invention can be incubated and/or treated at any stage in their preparation for administration with a number of agents or factors. These agents or factors aid in promoting the survival, growth, differentiation, and/or integration of the cells in vitro and/or in the recipient subject. Alternatively, the agents or factors aid in reducing plaque formation, promote plaque degradation, or aid in the treatment of the symptoms of Alzheimer's disease. For cell, cell lysate, and conditioned media administration, the cells may be incubated/treated with the additional agents or compounds at any time during dissection, limited digestion, dissociation, plating, and/or production of cell suspensions.

The administration of additional agents can begin prior to the administration cells or cell derivatives, can begin at the time of administration, or can begin after administration. The administration of additional agents can be limited in duration (e.g., can consist of a single administration of the agent) or can be of prolonged duration (e.g., can be given to the subject repeatedly over a long period of time).

In some embodiments, one or more compounds or components are administered in parallel, sequentionally or formulated directly with the population of cells or cell derivates. Examples of other components that may be administered include, but are not limited to: (1) other neurotrophic factors such as brain derived neurotrophic factor, ciliary neurotrophic factor, neurotrophin-3, neurotrophin 4/5, nerve growth factor, acidic fibroblast growth factor, basic fibroblast growth factor, platelet-derived growth factor, thyrotropin releasing hormone, epidermal growth factor, amphiregulin, transforming growth factor, transforming growth factor, insulin-like growth factor; (2) selected extracellular matrix components, such as one or more types of collagen known in the art, and/or growth factors, platelet-rich plasma, and drugs (alternatively, postpartum derived cells may be genetically engineered to express and produce growth factors); (3) anti-apoptotic agents (e.g., erythropoietin (EPO), EPO mimetibody, thrombopoietin, insulin-like growth factor (IGF)-I, IGF-II, hepatocyte growth factor, caspase inhibitors); (4) anti-inflammatory compounds (e.g., p38 MAP kinase inhibitors, TGF-beta inhibitors, statins, IL-6 and IL-1 inhibitors, Pemirolast, Tranilast, Remicade (Centocor, Inc., Malvern, Pa.), Sirolimus, and non-steroidal anti-inflammatory drugs (NSAIDS) (such as Tepoxalin, Tolmetin, and Suprafen); (5) immunosuppressive or immunomodulatory agents, such as calcineurin inhibitors, mTOR inhibitors, antiproliferatives, corticosteroids and various antibodies; (6) local anesthetics; and (7) other angiogenic factors, angiogenic drugs, or myoregenerative or myooprotective factors or drugs.

In one embodiment, such agents or factors are administered after the cells or cell derivatives of the invention have been administered therein. In some instances, for example, these agents can minimize or counteract detrimental effects on the cells resulting from the procedures used to prepare the cells for administration. For example, cells may experience cellular trauma and/or hypoxia which lead to the production of reactive oxygen species (ROS) such as superoxide radical anion, hydrogen peroxide, and the hydroxyl free radical. ROS are known to adversely affect cell function, most likely by affecting a variety of membrane and intracellular components including ion channels, membrane lipids, transport mechanisms such as the Na/K ATPase and Na/glutamate exchange transport and cytosolic enzymes such as glutamine synthase. In addition, ROS provoke membrane lipid peroxidation, and consequently may reduce the survival of the cells in the administers.

To minimize and/or counteract the adverse effects of these types of oxidative stress during preparation for administration, the cells of the present invention can be incubated and/or treated with antioxidants at any stage during the preparation. Examples of such antioxidants include the enzyme antioxidants superoxide dismutase (SOD) and glutathione peroxidase and agents which promote glutathione formation, e.g. N-acetyl cysteine (NAC). Other antioxidants includes lazaroids, e.g., U-74389G and U-83836E, which are aminosteroids that are designed to localize in the cell membrane and inhibit lipid peroxidation while scavenging free radicals. Other examples of antioxidants which can be added to the cell cultures and cell suspensions include TGF, vitamin E, vitamin C, beta carotene, and other compounds which scavenge ROS, inhibit the production of ROS, and/or inhibit lipid peroxidation.

Antioxidant enzymes, such as SOD, scavenge ROS and prevent the reaction of superoxide with nitric oxide to form peroxynitrite anion, which has been shown to be toxic to cultured cells. These enzymes can be incubated with the cells of the invention as described above. Another method of introducing these enzymes into the cellular preparations of the present invention is to genetically modify the cells to contain the nucleic acid encoding such enzymes. The genetically modified cells can then produce agents which enhance the survival, growth, and differentiation of the grafted cells in the recipient subject. For example, cells of the invention can be transfected with the human gene for Cu/Zn superoxide dismutase, a pivotal enzyme in the detoxification of oxygen free radicals, which results in the transfected cells expressing SOD and, consequently, efficiently detoxify ROS generated during tissue preparation and implantation to thereby increase administered cells survival.

In addition, the oxidative environment of the cells in vitro can be modified to inhibit cellular oxidative stress. For example, before administration, the partial pressure of oxygen in the cellular environment can be decreased from the normal oxygen partial pressure, i.e., approximately 150 torr O2, to a decreased oxygen partial pressure, i.e., 38 torr O2 (about 5% O2). This method of decreasing oxidative stress can be combined with treatment of the cells with one or more of the above-described antioxidants.

Inhibitors of NOS, such as gangliosides, FK506, and cyclosporine A, can be added to the cell preparations to inhibit the production of NO, thereby decreasing the production of peroxynitrite and its derivatives. Superoxide dismutase is another agent which can decrease the adverse effects of overproduction of NO and the toxic effects it mediates.

To prevent trauma and its associated adverse effects, e.g., membrane peroxidation, free radical induced cell damage induced by preparation of the cells of the invention for implantation, the cells of the invention can be transfected with nucleic acids encoding antiapoptotic gene products such as the bcl-2 and/or the crmA gene product. Further, the transfected cells of the invention can be treated with agents which upregulate the expression or function of these gene products, e.g., TGF1 and TGF3 which upregulate the expression of bcl-2, nerve growth factor (NGF) and platelet-derived growth factor (PDGF). Further, the cells of the invention can also be transfected with nucleic acid encoding these factors.

To further promote the survival of the cells of the invention in the recipient subject, the cells can be administered in conjunction with an angiogenic agent or transfected with nucleic acid encoding an angiogenic agent. Upon administration, the angiogenic agent promotes the ingrowth of blood vessels into the population of cells. As a result of this vessel ingrowth, the administered cells obtain sufficient nutrients to proliferate and survive within the recipient subject. Many growth factors exhibit angiogenic activity. For example, vascular endothelial growth factor (VEGF), PDGF, acidic and basic fibroblast growth factor (FGF), epidermal growth factor (EGF), and K-FGF possess angiogenic activity and can be used in the methods of the invention to encourage blood vessel ingrowth into the administered cells of the invention.

Other factors, such as neurotrophic factors, which contribute to neural development, nerve fiber formation, and maintenance of neurons can be added to the cells of the invention in vitro during preparation for administration and/or to the cell suspension itself for introduction into the individual subject along with the cells of the invention. The cells of the invention can also be genetically modified to produce such neurotrophic factors as described herein. The neurotrophic factor which is added to the cells of the present invention can be selected based on the presence of its receptors on the cells which are to be administered. For example, mesencephalic cells possess receptors for the following neurotrophic factors: glial cell line-derived neurotrophic factor (GDNF), which promotes the survival of, morphological differentiation of, and high affinity dopamine uptake in mesencephalic cells; brain-derived neurotrophic factor (BDNF); ciliary neurotrophic factor (CNTF), which prevents axotomy induced degeneration of mesencephalic cells; midkine, which promotes the survival and differentiation of mesencephalic cells; EGF, which increases survival and maturation of mesencephalic cells; insulin-like growth factor I and II and insulin; acidic FGF; basic FGF, which induce a significant increase in the number of neurite-bearing cells as well as in the degree of their fiber network; neurotrophin-3 (NT-3) and neurotrophin 4/5 (NT-4/5); and transforming growth factor-2 (TGF2) and transforming growth factor-3 (TGF3).

Neurotrophic factors which promote the survival of neural cells can be selected based on the presence of receptors on the cells. Receptors for basic FGF, BDNF, NT-3 and NT-4/5 can be found on certain neural cells. Thus, in one embodiment, the cells of the invention can be transfected with the nucleic acids encoding one or more of these factors. In another embodiment, one or more of these factors can be added to the preparation of neural cells prior to administration. These neurotrophic factors enhance the survival of the cells of the invention in the recipient subject. Similarly, neurotrophic factors which exhibit specificity for cortical cells, and consequently, which can be used to promote the survival of such cell upon engraftment into a recipient subject, include nerve growth factor (NGF), which prevents, for example, atrophy of axotomized forebrain cholinergic neurons; BDNF, and NT-3 and NT-4/5.

In another embodiment, the neurotrophic factors described herein can be used together or in combination with other compounds, such as neurotransmitters, to augment their neurotrophic effects. In addition, it is contemplated that various combinations of neurotrophic factors described herein can act synergistically and, therefore, can be used together to promote survival of the administered cells of the invention.

Certain drugs also possess neurotrophic activity. Examples of such drugs include FK506 and cyclosporin A which block the neurotoxicity elicited by glutamate acting at N-methyl-D-aspartate (NMDA) receptors by, for example, augmenting phosphorylated levels of NOS. As phosphorylated NOS inhibits its catalytic activity, these drugs effectively reduce NO formation and prevent the neurotoxic effects of NMDA on these cells. Other drugs which possess neurotrophic activity and can be used in the present invention are those small molecules which bind to the same binding proteins as FK506 and/or cyclosporin A and, therefore, mediate similar neuroprotective effects. In one embodiment, these drugs are administered to the subject in addition to the population of cells to treat chronic pain and/or spasticity.

In one embodiment, combinations of one or more of the above-described agents and factors can be used to promote survival of the cells of the invention prior to or after the cells are administered into recipient subjects. For example, cells of the present invention can be contacted with one or more of the agents or factors described herein to promote survival of the cells in vitro and/or in vivo. In another embodiment, the cells of the invention can be transfected with the nucleic acid of one or more of the agents or factors described herein and also contacted with one or more of the agents or factors described herein. Moreover, although many of the neurotrophic factors described herein are specific for a particular cell type, the association of these factors with such a cell type does not exclude the use of that factor with a different cell type.

Treatment of the cells of the invention with the agents or factors described herein can occur simultaneously or sequentially. In addition, some embodiments include use of one or more agents or factors either injected in parallel or sequentially with cell administration, or formulated directly into one or more pharmaceutically acceptable carriers.

In one embodiment, the cells are pre-treated with electrical stimulation prior to administration. The exposure of hUTC to an electric field may improve the repair of target tissues by increasing the proliferation and viability of hUTC. Electrical stimulation may also enhance the secretion of trophic factors, the expression of extracellular matrix (ECM) proteins, and the engraftment of implanted hUTC. In addition, the electrical stimulation may mobilize or induce the resident cells at the implant site to initiate the repair process.

The hUTC may be electrically stimulated by the application of an electric field using a single dose, a sustained dose, or multiple doses for different lengths of time. The stimulation can be done prior to or after implantation of hUTC. It is conceivable that different parameters of electrical stimulation will be used to optimize the effects hUTC. Electrical stimulation may also be applied to cells or tissue grown in a three-dimensional environment or bioreactor.

In another aspect of the invention, cells or minced tissue may be combined with a source of microcurrent. The microcurrent couple be delivered to the cells as a galvanic couple of particulates of zinc and copper (0.01 microns-0.1 microns) as energy source or other elements capable of generating microcurrent. Alternatively, the galvanic couple of copper and zinc or other elements could be incorporated into polymer microcarriers/scaffolds and cells would be combined with microcarriers/scaffolds for transplantation.

If the population of cells used by the medical practitioner is postpartum derived cells, then administration with allogeneic, or even xenogeneic, cells may be tolerated in some instances as these cells have been shown not to stimulate allogeneic PBMCs in a mixed lymphocyte reaction. Accordingly, it is recognized that the cells themselves provide an immunosuppressant effect, thereby preventing host rejection of the administered population of cells. In such instances, pharmacological immunosuppression during cell therapy may not be necessary.

However, in other instances it may be desirable or appropriate to pharmacologically immunosuppress a patient prior to initiating cell therapy. This may be accomplished through the use of systemic or local immunosuppressive agents, or it may be accomplished by delivering the cells in an encapsulated device, as described above. These and other means for reducing or eliminating an immune response to the administered cells are known in the art. As an alternative, the population of cells may be genetically modified to reduce their immunogenicity, as mentioned above.

In addition, survival of an administered population of cells in a living patient can be determined through the use of a variety of scanning techniques, e.g., computerized axial tomography (CAT or CT) scan, magnetic resonance imaging (MRI) or positron emission tomography (PET) scans. Determination of cell survival can also be done post mortem by removing the neural tissue and surrounding tissues, and examining it visually or through a microscope. Alternatively, cells can be treated with stains that are specific for neural tissue, or its surrounding tissues. Administered cells can also be identified by prior incorporation of tracer dyes such as rhodamine- or fluorescein-labeled microspheres, fast blue, ferric microparticles, bisbenzamide or genetically introduced reporter gene products, such as beta-galactosidase or beta-glucuronidase.

In another embodiment, the administration of the population of cells to treat Alzheimer's disease can be coupled with administration of traditional drugs used to treat Alzheimer's disease, or the symptoms of Alzheimer's disease. In certain subjects, such combination therapies may result in optimal amelioration of symptoms. The drugs that may also be administered with the population of cells includes any drugs used to treat the symptoms of forgetfulness, loss of concentration, weight loss, motor function issues, hearing loss, decline in reading or linguistic ability, confusion, poor judgment, agitation, withdrawal, hallucinations, seizures, Parkinsonian-type features, decreased muscle tone, myoclonus, incontinence, mutism, and psychotic disorders.

The dosage forms and regimes for administering the population of cells or any of the other therapeutic or pharmaceutical compositions described herein are developed in accordance with good medical practice, taking into account the condition of the individual patient, e.g., nature and extent of the neural injury or damage, age, sex, body weight and general medical condition, and other factors known to medical practitioners. Thus, the effective amount of a pharmaceutical composition to be administered to a patient is determined by these considerations as known in the art.

In another embodiment, agents which inhibit T cell activity in the subject can be administered in addition to the subject cells. As used herein, an agent which inhibits T cell activity is defined as an agent which results in removal or destruction of T cells within a subject or inhibits T cell functions within the subject, thus the T cells may still be present in the subject but are in a non-functional state, such that they are unable to proliferate or elicit or perform effector functions, such as cytokine production, cytotoxicity etc. The term "T cell" encompasses mature peripheral blood T lymphocytes. The agent which inhibits T cell activity may also inhibit the activity or maturation of immature T cells.

Pharmaceutically Acceptable Carriers

Further, the population of cells can be administered in any physiologically compatible carrier, such as a buffered saline solution. Pharmaceutically acceptable carriers and diluents are discussed within this disclosure, including but not limited to, saline, aqueous buffer solutions, solvents and/or dispersion media. The use of such carriers and diluents is well known in the art. Other examples include liquid media, for example, Dulbeccos Modified Eagle's Medium (DMEM), sterile saline, sterile phosphate buffered saline, Leibovitz's medium (L15, Invitrogen, Carlsbad, Calif.), dextrose in sterile water, and any other physiologically acceptable liquid. The solution is preferably sterile and fluid to the extent that easy syringability exists. Preferably, the solution is stable under the conditions of manufacture and storage and preserved against the contaminating action of microorganisms such as bacteria and fungi through the use of, for example, parabens, chlorobutanol, phenol, ascorbic acid, thimerosol, and the like. Solutions of the invention can be prepared by using a pharmaceutically acceptable carrier or diluent and, as required, other ingredients enumerated above, followed by filtered sterilization, and then incorporating the population of cells as described herein.

Pharmaceutical compositions of the invention may include preparations made from cells that are formulated with a pharmaceutically acceptable carrier or medium. Suitable pharmaceutically acceptable carriers include any discussed within this disclosure, including but not limited to, water, salt solution (such as Ringer's solution), alcohols, oils, gelatins, polyvinyl pyrrolidine, carbohydrates such as lactose, amylose, or starch, fatty acid esters, and hydroxymethylcellulose. Such preparations can be sterilized, and if desired, mixed with auxiliary agents such as lubricants, preservatives, stabilizers, wetting agents, emulsifiers, salts for influencing osmotic pressure, buffers, and coloring agents. Pharmaceutical carriers suitable for use in the present invention are known in the art and are described, for example, in Pharmaceutical Sciences ($17^{t1}$ Ed., Mack Pub. Co., Easton, Pa.) and WO 96/05309, which is incorporated by reference in its entirety.

In one preferred embodiment, the population of cells is administered in an artificial CSF. Artificial CSF compatible with the invention include any which contain the proper agent stability, solubility and pharmacokinetics for delivery to the brain. One exemplary CSF solution includes NaCl, KCl, $CaCl_2 \times 2$ $H_2O$ and $MgCl_2 \times 6$ $H_2O$ in the approximate measurements of about 8.66 g, 0.224 g, 0.204 g, and 0.163 g, respectively, per 500 ml $ddH_2O$. Another exemplary CSF solution includes $Na_2HPO_4 \times 7$ $H_2O$ and $NaH_2PO_4 \times H_2O$ in the approximate measurements of about 0.214 and 0.027, respectively, per 500 ml $ddH_2O$. Another exemplary CSF solution includes a ratio (in mM) of about 187.5 Na:2.6 K:1.1 Ca:1.1 Mg:0.8 P:119 Cl:23.3 $HCO_3$. In one preferred embodiment, the CSF solution mimics real CSF electrolyte concentration, and thus has the approximate concentration in mM of 154 Na:3.0 K:1.3 Ca:0.9 Ca:0.9 Mg:0.4 P:136 Cl:24.1 $HCO_3$.

Cells in a semi-solid or solid carrier may also be prepared and surgical implanted at the site of neurotic plaque formation. It will be appreciated that liquid compositions also may be administered by surgical procedures. In particular embodiments, semi-solid or solid pharmaceutical compositions may comprise semi-permeable gels, matrices, cellular scaffolds and the like, which may be non-biodegradable or biodegradable. For example, in certain embodiments, it may be desirable or appropriate to sequester the exogenous cells from their surroundings, yet enable the cells to secrete and deliver biological molecules (e.g. neurotropin factors) to surrounding cells. In these embodiments, cells may be formulated as autonomous implants comprising postpartum derived cells surrounded by a non-degradable, selectively permeable barrier that physically separates the administered cells from host tissue. Such implants are sometimes referred to as "immunoprotective," as they have the capacity to prevent immune cells and macromolecules from killing the administered cells in the absence of pharmacologically induced immunosuppression. In other embodiments, different varieties of degradable gels and networks are utilized for the pharmaceutical compositions of the invention. For example, degradable materials particularly suitable include any discussed within this disclosure, including but not limited to, biocompatible polymers, such as poly(lactic acid), poly (lactic acid-co-glycolic acid), methylcellulose, hyaluronic acid, collagen, and the like.

In another embodiment, one or more hydrogels are used for the pharmaceutical compositions. The one or more hydrogels may include collagen, atelocollagen, fibrin constructs, hydrophilic vinyl and acrylic polymers, polysaccharides such as calcium alginate, and poly(ethylene oxide). Further, the hydrogel may be formed of poly(2-hydroxyethyl methacrylate), poly(acrylic acid), self-assembling peptides (e.g., RAD 16), poly(methacrylic acid), poly(N-vinyl-2-pyrrolidinone), poly(vinyl alcohol) and their copolymers with each other and with hydrophobic monomers such as methyl methacrylate, vinyl acetate, and the like. Also preferred are hydrophilic polyurethanes containing large poly (ethylene oxide) blocks. Other preferred materials include hydrogels comprising interpenetrating networks of polymers, which may be formed by addition or by condensation polymerization, the components of which may comprise hydrophilic and hydrophobic monomers such as those just enumerated. In situ-forming degradable networks are also suitable for use in the invention (see, e.g., Anseth, K S et al. (2002) *J. Controlled Release* 78:199-209; Wang, D. et al., (2003) *Biomaterials* 24:3969-3980; U.S. Patent Publication 2002/0022676 to He et al., which are all incorporated by reference in their entireties). These in situ forming materials are formulated as fluids suitable for injection, then may be induced to form a hydrogel by a variety of means such as change in temperature, pH, and exposure to light in situ or in vivo.

In other embodiments, the pharmaceutical composition comprises a biocompatible matrix made of natural, modified natural or synthetic biodegradable polymers, including homopolymers, copolymers and block polymers, as well as combinations thereof. Examples of suitable biodegradable polymers or polymer classes include any biodegradable polymers discussed within this disclosure, including but not limited to, fibrin, collagen types I, II, III, IV and V, elastin, gelatin, vitronectin, fibronectin, laminin, thrombin, poly (aminoacid), oxidized cellulose, tropoelastin, silk, ribonucleic acids, deoxyribonucleic acids; proteins, polynucleotides, gum arabic, reconstituted basement membrane matrices, starches, dextrans, alginates, hyaluron, chitin, chitosan, agarose, polysaccharides, hyaluronic acid, poly(lactic acid), poly(glycolic acid), polyethylene glycol, decellularized tissue, self-assembling peptides, polypeptides, glycosaminoglycans, their derivatives and mixtures thereof. Suitable polymers also include poly(lactide) (PLA) which can be formed of L(+) and D(−) polymers, polyhydroxybutyrate, polyurethanes, polyphoshazenes, poly(ethylene glycol)-poly(lactide-co-glycolide) co-polymer, degradable polycyanoacrylates and degradable polyurethanes. For both glycolic acid and lactic acid, an intermediate cyclic dimer is may be prepared and purified prior to polymerization. These intermediate dimers are called glycolide and lactide, respectively.

Other useful biodegradable polymers or polymer classes include, without limitation, aliphatic polyesters, poly(alkylene oxalates), tyrosine derived polycarbonates, polyiminocarbonates, polyorthoesters, polyoxaesters, polyamidoesters, polyoxaesters containing amine groups, polypropylene fumarate), polyfumarates, polydioxanones, polycarbonates, polyoxalates, poly(alpha-hydroxyacids), poly(esters), polyurethane, poly(ester urethane), poly(ether urethane), polyanhydrides, polyacetates, polycaprolactones, poly(orthoesters), polyamino acids, polyamides and blends and copolymers thereof. Additional useful biodegradable polymers include, without limitation stereopolymers of L- and D-lactic acid, copolymers of bis(para-carboxyphenoxy) propane and sebacic acid, sebacic acid copolymers, copolymers of caprolactone, poly(lactic acid)/poly(glycolic acid)/polyethyleneglycol copolymers, copolymers of polyurethane and poly(lactic acid), copolymers of alpha-amino acids, copolymers of alpha-amino acids and caproic acid, copolymers of alpha-benzyl glutamate and polyethylene glycol, copolymers of succinate and poly(glycols), polyphosphazene, poly(hydroxyalkanoates) and mixtures thereof. Binary and ternary systems also are contemplated.

In general, the materials used to form a matrix are desirably configured so that it has mechanical properties that are suitable for the intended application, remains sufficiently intact until tissue has in-grown and healed, does not invoke an inflammatory or toxic response, is metabolized in the body after fulfilling its purpose, is easily processed into the desired final product to be formed, demonstrates acceptable shelf-life, and is easily sterilized.

In another embodiment, the population of cells is administered by use of a scaffold. The composition, shape, and porosity of the scaffold may be any described above. These three-dimensional biomaterials contain the living cells attached to the scaffold, dispersed within the scaffold, or incorporated in an extracellular matrix entrapped in the scaffold. Once implanted into the target region of the body, these implants become integrated with the host tissue, wherein the administered cells gradually become established. Non-limiting examples of scaffolds that may be used in the present invention include textile structures such as weaves, knits, braids, meshes, non-wovens, and warped knits; porous foams, semi-porous foams, perforated films or sheets, microparticles, beads, and spheres and composite structures being a combination of the above structures. Nonwoven mats may, for example, be formed using fibers comprised of a synthetic absorbable copolymer of glycolic and lactic acids (PGA/PLA), sold under the tradename VICRYL sutures (Ethicon, Inc., Somerville, N.J.). Foams, composed of, for example, poly(epsilon-caprolactone)/poly (glycolic acid) (PCL/PGA) copolymer, formed by processes such as freeze-drying, or lyophilized, as discussed in U.S. Pat. No. 6,355,699 (Bruder et al., which is incorporated by reference in its entirety), also may be utilized. In another embodiment, the framework is a felt, which can be composed of a multifilament yarn made from a bioabsorbable material. The yarn is made into a felt using standard textile processing techniques consisting of crimping, cutting, carding and needling. In another embodiment, cells are seeded onto foam scaffolds that may be used as composite structures. In many of the abovementioned embodiments, the framework may be molded into a useful shape, such as to fill a tissue void. Furthermore, it will be appreciated that the population of cells may be cultured on pre-formed, non-degradable surgical or implantable devices.

In another embodiment, before administration, the population of cells is incubated in the presence of one or more factors, or under conditions, that stimulate stem cell differentiation. Such factors are known in the art and the skilled artisan will appreciate that determination of suitable conditions for differentiation can be accomplished with routine experimentation. Optimization of such conditions can be accomplished by statistical experimental design and analysis; for example, response surface methodology allows simultaneous optimization of multiple variables, for example in a biological culture. Presently preferred factors include, but are not limited to, growth or trophic factors, chemokines, cytokines, cellular products, demethylating agents, and other stimuli which are now known or later determined to stimulate differentiation. Alternatively, the composition administered to the patient includes a population of cells with one or more factors that stimulate cell differentiation, where the cell differentiation occurs in vitro at the tissue site.

Stem Cells and Postpartum Derived Cells, Including hUTC

The description of the isolation and characterization of the preferred hUTC of the invention may be found in U.S. Patent Publication Nos. 2005/0032209, 2005/0058631 and 2005/0054098 which are incorporated in their entirety.

In some embodiments, the cells are stem cells. As noted above, stem cells are undifferentiated cells defined by the ability of a single cell both to self-renew and to differentiate to produce progeny cells, including self-renewing progenitors, non-renewing progenitors, and terminally differentiated cells.

In one preferred embodiment, the stem cells are postpartum derived cells. To isolate postpartum derived cells, a mammalian placenta or umbilical cord is recovered upon or shortly after termination of either a full-term or pre-term pregnancy, for example, after expulsion of after birth. The postpartum tissue may be transported from the birth site to a laboratory in a sterile container such as a flask, beaker, culture dish, or bag. The container may have a solution or medium, including but not limited to a salt solution, such as Dulbecco's Modified Eagle's Medium (DMEM) (also known as Dulbecco's Minimal Essential Medium) or phosphate buffered saline (PBS), or any solution used for transportation of organs used for administration, such as University of Wisconsin solution or perfluorochemical solution. One or more antibiotic and/or antimycotic agents, such as but not limited to penicillin, streptomycin, amphotericin B, gentamicin, and nystatin, may be added to the medium or buffer. The postpartum tissue may be rinsed with an anticoagulant solution such as heparin-containing solution. It is preferable to keep the tissue at about 4-10° C. prior to extraction of cells. It is even more preferable that the tissue not be frozen prior to extraction of cells.

The postpartum derived cells are preferably isolated in an aseptic environment. The umbilical cord may be separated from the placenta by means known in the art. Alternatively, the umbilical cord and placenta are used without separation. Blood and debris are preferably removed from the postpartum tissue prior to isolation of postpartum derived cells. For example, the postpartum tissue may be washed with buffer solution, including but not limited to phosphate buffered saline. The wash buffer also may comprise one or more antimycotic and/or antibiotic agents, including but not limited to penicillin, streptomycin, amphotericin B, gentamicin, and nystatin.

Postpartum tissue comprising a whole placenta or a fragment or section thereof is disaggregated by mechanical force (mincing or shear forces). The isolation procedure may also utilize an enzymatic digestion process. Many enzymes are known in the art to be useful for the isolation of individual cells from complex tissue matrices to facilitate growth in culture. Digestion enzymes range from weakly digestive (e.g. deoxyribonucleases and the neutral protease, dispase) to strongly digestive (e.g. papain and trypsin), and are available commercially. A non-exhaustive list of enzymes compatible herewith includes mucolytic enzyme activities, metalloproteases, neutral proteases, serine proteases (such as trypsin, chymotrypsin, or elastase), and deoxyribonucleases. Presently preferred are enzyme activities selected from metalloproteases, neutral proteases and mucolytic activities. For example, collagenases are known to be useful for isolating various cells from tissues. Deoxyribonucleases can digest single-stranded DNA and can minimize cell-clumping during isolation. Preferred methods involve enzymatic treatment with, for example, collagenase and dispase, or collagenase, dispase, and hyaluronidase. In certain embodiments, a mixture of collagenase and the neutral protease dispase are used in the dissociating step. More specific embodiments employ digestion in the presence of at least one collagenase from *Clostridium histolyticum*, and either of the protease activities, dispase and thermolysin. Still other embodiments employ digestion with both collagenase and dispase enzyme activities. Also utilized are methods that include digestion with a hyaluronidase activity in addition to collagenase and dispase activities. The skilled artisan will appreciate that many such enzyme treatments are known in the art for isolating cells from various tissue sources. For example, the enzyme blends for tissue disassociation sold under the trade name LIBERASE™ (Roche, Indianapolis, Ind.) are suitable for use in the instant methods. Other sources of enzymes are known, and the skilled artisan may also obtain such enzymes directly from their natural sources. The skilled artisan is also well-equipped to assess new or additional enzymes or enzyme combinations for their utility in isolating the cells of the invention. Preferred enzyme treatments are 0.5, 1, 1.5, or 2 hours long or longer. In other preferred embodiments, the tissue is incubated at 37° C. during the enzyme treatment of the dissociation step.

In some embodiments of the invention, postpartum tissue is separated into sections comprising various aspects of the tissue, such as neonatal, neonatal/maternal, and maternal aspects of the placenta, for instance. The separated sections then are dissociated by mechanical and/or enzymatic dissociation according to the methods described herein. Cells of neonatal or maternal lineage may be identified by any means known in the art, for example, by karyotype analysis or in situ hybridization for a Y chromosome.

Methods for the selection of the most appropriate culture medium, medium preparation, and cell culture techniques are well known in the art and are described in a variety of sources, including Doyle et al., (eds.), 1995, CELL & TISSUE CULTURE: LABORATORY PROCEDURES, John Wiley & Sons, Chichester; and Ho and Wang (eds.), 1991, ANIMAL CELL BIOREACTORS, Butterworth-Heinemann, Boston, which are incorporated herein by reference.

After culturing the isolated cells or tissue fragments for a sufficient period of time, postpartum derived cells will have grown out, either as a result of migration from the postpartum tissue or cell division, or both. In some embodiments of the invention, postpartum derived cells are passaged, or removed to a separate culture vessel containing fresh medium of the same or a different type as that used initially, where the population of cells can be mitotically expanded. The cells of the invention may be used at any point between passage 0 and senescence. The cells preferably are passaged between about 3 and about 25 times, more preferably are passaged about 4 to about 12 times, and preferably are passaged 10 or 11 times. Cloning and/or subcloning may be performed to confirm that a clonal population of cells has been isolated.

In some aspects of the invention, the different cell types present in postpartum tissue are fractionated into subpopulations from which the postpartum derived cells can be isolated. Fractionation or selection may be accomplished using standard techniques for cell separation including, but not limited to, enzymatic treatment to dissociate postpartum tissue into its component cells, followed by cloning and selection of specific cell types, including but not limited to selection based on morphological and/or biochemical markers; selective growth of desired cells (positive selection), selective destruction of unwanted cells (negative selection); separation based upon differential cell agglutinability in the mixed population as, for example, with soybean agglutinin; freeze-thaw procedures; differential adherence properties of the cells in the mixed population; filtration; conventional and zonal centrifugation; centrifugal elutriation (counter-streaming centrifugation); unit gravity separation; counter-current distribution; electrophoresis; and fluorescence activated cell sorting (FACS). Suitable clonal selection and cell separation techniques are described in Freshney, 1994, CULTURE OF ANIMAL CELLS: A MANUAL OF BASIC TECHNIQUES, 3rd Ed., Wiley-Liss, Inc., New York, which is incorporated by reference in its entirety.

The culture medium is changed as necessary, for example, by carefully aspirating the medium from the dish, for example, with a pipette, and replenishing with fresh medium. Incubation is continued until a sufficient number or density of cells accumulates in the dish. The original explanted tissue sections may be removed and the remaining cells trypsinized using standard techniques or using a cell scraper. After trypsinization, the cells are collected, removed to fresh medium and incubated as above. In some embodiments, the medium is changed at least once at approximately 24 hours post-trypsinization to remove any floating cells. The cells remaining in culture are considered to be postpartum derived cells.

Postpartum derived cells may be cryopreserved. Accordingly, in a preferred embodiment described in greater detail below, postpartum derived cells for autologous transfer (for either the mother or child) may be derived from appropriate postpartum tissues following the birth of a child, then cryopreserved so as to be available in the event they are later needed for administration.

Postpartum-derived cells may be characterized, for example, by growth characteristics (e.g., population doubling capability, doubling time, passages to senescence), karyotype analysis (e.g., normal karyotype; maternal or neonatal lineage), flow cytometry (e.g., FACS analysis), immunohistochemistry and/or immunocytochemistry (e.g., for detection of epitopes), gene expression profiling (e.g., gene chip arrays; polymerase chain reaction (for example, reverse transcriptase PCR, real time PCR, and conventional PCR)), protein arrays, protein secretion (e.g., by plasma clotting assay or analysis of PDC-conditioned medium, for example, by Enzyme Linked ImmunoSorbent Assay (ELISA)), mixed lymphocyte reaction (e.g., as measure of stimulation of PBMCs), and/or other methods known in the art.

Examples of postpartum derived cells derived from placental tissue were deposited with the American Type Culture Collection (ATCC, Manassas, Va.) and assigned ATCC Accession Numbers as follows: (1) strain designation PLA 071003 (P8) was deposited Jun. 15, 2004 and assigned Accession No. PTA-6074; (2) strain designation PLA 071003 (P11) was deposited Jun. 15, 2004 and assigned Accession No. PTA-6075; and (3) strain designation PLA 071003 (P16) was deposited Jun. 16, 2004 and assigned Accession No. PTA-6079. Examples of postpartum-derived cells derived from umbilicus tissue were deposited with the American Type Culture Collection on Jun. 10, 2004, and assigned ATCC Accession Numbers as follows: (1) strain designation UMB 022803 (P7) was assigned Accession No. PTA-6067; and (2) strain designation UMB 022803 (P17) was assigned Accession No. PTA-6068.

In various embodiments, the postpartum derived cells possess one or more of the following growth features (1) they require L-valine for growth in culture; (2) they are capable of growth in atmospheres containing oxygen from about 5% to at least about 20% (3) they have the potential for at least about 40 doublings in culture before reaching senescence; and (4) they attach and expand on a coated or uncoated tissue culture vessel, wherein the coated tissue culture vessel comprises a coating of gelatin, laminin, collagen, polyornithine, vitronectin or fibronectin.

In certain embodiments, the postpartum derived cells possess a normal karyotype, which is maintained as the cells are passaged. Karyotyping is particularly useful for identifying and distinguishing neonatal from maternal cells derived from placenta. Methods for karyotyping are available and known to those of skill in the art.

In other embodiments, the postpartum derived cells may be characterized by production of certain proteins, including (1) production of at least one of tissue factor, vimentin, and alpha-smooth muscle actin; and (2) production of at least one of CD10, CD13, CD44, CD73, CD90, PDGFr-alpha, PD-L2 and HLA-A,B,C cell surface markers, as detected by flow cytometry. In other embodiments, the Postpartum derived cells may be characterized by lack of production of at least one of CD31, CD34, CD45, CD80, CD86, CD117, CD141, CD178, B7-H2, HLA-G, and HLA-DR,DP,DQ cell surface markers, as detected by flow cytometry. Particularly preferred are cells that produce at least two of tissue factor, vimentin, and alpha-smooth muscle actin. More preferred are those cells producing all three of the proteins tissue factor, vimentin, and alpha-smooth muscle actin.

In other embodiments, the postpartum derived cells may be characterized by gene expression, which relative to a human cell that is a fibroblast, a mesenchymal stem cell, or an iliac crest bone marrow cell, is increased for a gene encoding at least one of interleukin 8; reticulon 1; chemokine (C—X—C motif) ligand 1 (melonoma growth stimulating activity, alpha); chemokine (C—X—C motif) ligand 6 (granulocyte chemotactic protein 2); chemokine (C—X—C motif) ligand 3; tumor necrosis factor, alpha-induced protein 3; C-type lectin superfamily member 2; Wilms tumor 1; aldehyde dehydrogenase 1 family member A2; renin; oxidized low density lipoprotein receptor 1; *Homo sapiens* clone IMAGE:4179671; protein kinase C zeta; hypothetical protein DKFZp564F013; downregulated in ovarian cancer 1; and *Homo sapiens* gene from clone DKFZp547k1113.

In yet other embodiments, the postpartum derived cells may be characterized by gene expression, which relative to a human cell that is a fibroblast, a mesenchymal stem cell, or an iliac crest bone marrow cell, is reduced for a gene encoding at least one of: short stature homeobox 2; heat shock 27 kDa protein 2; chemokine (C—X—C motif) ligand 12 (stromal cell-derived factor 1); elastin (supravalvular aortic stenosis, Williams-Beuren syndrome); *Homo sapiens* mRNA; cDNA DKFZp586M2022 (from clone DKFZp586M2022); mesenchyme homeo box 2 (growth arrest-specific homeo box); sine oculis homeobox homolog 1 (*Drosophila*); crystallin, alpha B; disheveled associated activator of morphogenesis 2; DKFZP586B2420 protein; similar to neuralin 1; tetranectin (plasminogen binding protein); src homology three (SH3) and cysteine rich domain; cholesterol 25-hydroxylase; runt-related transcription factor 3; interleukin 11 receptor, alpha; procollagen C-endopeptidase enhancer; frizzled homolog 7 (*Drosophila*); hypothetical gene BC008967; collagen, type VIII, alpha 1; tenascin C (hexabrachion); iroquois homeobox protein 5; hephaestin; integrin, beta 8; synaptic vesicle glycoprotein 2; neuroblastoma, suppression of tumorigenicity 1; insulin-like growth factor binding protein 2, 36 kDa; *Homo sapiens* cDNA F1112280 fis, clone MAMMA1001744; cytokine receptor-like factor 1; potassium intermediate/small conductance calcium-activated channel, subfamily N, member 4; integrin, beta 7; transcriptional co-activator with PDZ-binding motif (TAZ); sine oculis homeobox homolog 2 (Drosophila); KIAA1034 protein; vesicle-associated membrane protein 5 (myobrevin); EGF-containing fibulin-like extracellular matrix protein 1; early growth response 3; distal-less homeo box 5; hypothetical protein FlJ20373; aldo-keto reductase family 1, member C3 (3-alpha hydroxysteroid dehydrogenase, type II); biglycan; transcriptional co-activator with PDZ-binding motif (TAZ); fibronectin 1; proenkephalin; integrin, beta-like 1 (with EGF-like repeat domains); *Homo sapiens* mRNA full length insert cDNA clone EUROIMAGE 1968422; EphA3; KIAA0367 protein; natriuretic peptide receptor C/guanylate cyclase C (atrionatriuretic peptide receptor C); hypothetical protein FlJ14054; *Homo sapiens* mRNA; cDNA DKFZp564B222 (from clone DKFZp564B222); BCL2/adenovirus E1B 19 kDa interacting protein 3-like; AE binding protein 1; and cytochrome c oxidase subunit VIIa polypeptide 1 (muscle).

In other embodiments, the postpartum derived cells may be characterized by secretion of at least one of MCP-1, IL-6, IL-8, GCP-2, HGF, KGF, FGF, HB-EGF, BDNF, TPO, MIP1a, RANTES, and TIMP1. In some embodiments, the postpartum derived cells may be characterized by lack of secretion of at least one of TGF-beta2, ANG2, PDGFbb, MIP1b, I309, MDC, and VEGF, as detected by ELISA.

In some preferred embodiments, the postpartum derived cells are derived from umbilical cord tissue substantially free of blood, are capable of self-renewal and expansion in culture, require L-valine for growth, can grow in at least about 5% oxygen, and comprise at least one of the following characteristics: potential for at least about 40 doublings in culture; attachment and expansion on a coated or uncoated tissue culture vessel that comprises a coating of gelatin, laminin, collagen, polyornithine, vitronectin, or fibronectin; production of vimentin and alpha-smooth muscle actin; production of CD10, CD13, CD44, CD73, and CD90; and, expression of a gene, which relative to a human cell that is a fibroblast, a mesenchymal stem cell, or an iliac crest bone marrow cell, is increased for a gene encoding interleukin 8 and reticulon 1. In some embodiments, such postpartum derived cells do not produce CD45 and CD117.

In preferred embodiments, the cell comprises two or more of the above-listed growth, protein/surface marker production, gene expression or substance-secretion characteristics. More preferred are those cells comprising three, four, five or more of the characteristics. Still more preferred are postpartum-derived cells comprising six, seven, eight or more of the characteristics. Still more preferred presently are those cells comprising all of above characteristics.

Among cells that are presently preferred for use with the invention in several of its aspects are postpartum cells having the characteristics described above and more particularly those wherein the cells have normal karyotypes and maintain normal karyotypes with passaging, and further wherein the cells express each of the markers CD10, CD13, CD44, CD73, CD90, PDGFr-alpha, and HLA-A,B,C, wherein the cells produce the immunologically-detectable proteins which correspond to the listed markers. Still more preferred are those cells which in addition to the foregoing do not produce proteins corresponding to any of the markers CD31, CD34, CD45, CD117, CD141, or HLA-DR,DP,DQ, as detected by flow cytometry.

Certain cells having the potential to differentiate along lines leading to various phenotypes are unstable and thus can spontaneously differentiate. Presently preferred for use with the invention are cells that do not spontaneously differentiate, for example along myoblast, skeletal muscle, vascular smooth muscle, pericyte, hemangiogenic, angiogenic, vasculogenic, or vascular endothelial lines. Preferred cells, when grown in growth medium, are substantially stable with respect to the cell markers produced on their surface, and with respect to the expression pattern of various genes, for example as determined using a medical diagnostic test sold under the trade name GENECHIP (Affymetrix, Inc., Santa Clara, Calif.). The cells remain substantially constant, for example in their surface marker characteristics over passaging, through multiple population doublings.

Another aspect of the invention features use of populations of the postpartum derived cells described above. In some embodiments, the cell population is heterogeneous. A heterogeneous cell population of the invention may comprise at least about 5%, 10%, 20%, 30%, 40%, 50%, 60%, 70%, 80%, 90%, or 95% postpartum derived cells of the invention. The heterogeneous cell populations of the invention may further comprise stem cells or other progenitor cells, such as myoblasts or other muscle progenitor cells, hemangioblasts, or blood vessel precursor cells, or it may further comprise fully differentiated neural cells. In some embodiments, the population is substantially homogeneous, i.e., comprises substantially only postpartum derived cells (preferably at least about 96%, 97%, 98%, 99% or more postpartum derived cells). The homogeneous cell population of the invention may comprise umbilicus- or placenta-derived cells. Homogeneous populations of umbilicus-derived cells are preferably free of cells of maternal lineage. Homogeneous populations of placenta-derived cells may be of neonatal or maternal lineage. Homogeneity of a cell population may be achieved by any method known in the art, for example, by cell sorting (e.g., flow cytometry) or by clonal expansion in accordance with known methods. Thus, preferred homogeneous postpartum derived cell populations may comprise a clonal cell line of postpartum-derived cells. Such populations are particularly useful when a cell clone with highly desirable functionality has been isolated.

In one embodiment, the cells are postpartum derived cells that are administered as undifferentiated cells, i.e., as cultured in growth medium. Alternatively, the postpartum derived cells may be administered following exposure in culture to conditions that stimulate differentiation toward a desired neural tissue.

In one preferred embodiment, the cells are hUTC.

Further, the population of cells may include more than one type of cell. Indeed, some embodiments include administration of cells which surround and support the neural cell such as vascular tissue.

Genetically Modified Cells

Cells used in the invention may also be genetically modified to produce therapeutically useful gene products, to produce agents to facilitate or support neural tissue survival, differentiation, phagocytic activity, or to produce factors to recruit progenitor cells to the area of neuritic plaques.

Genetic modification may be accomplished using any of a variety of vectors including, but not limited to, integrating viral vectors, e.g., retrovirus vector or adeno-associated viral vectors; non-integrating replicating vectors, e.g., papilloma virus vectors, SV40 vectors, adenoviral vectors; or replication-defective viral vectors. Other methods of introducing DNA into cells include the use of liposomes, electroporation, a particle gun, or by direct DNA injection.

For instance, the cells may be genetically engineered to express and/or secrete a foreign molecule (e.g., a heterologous molecule not normally made by the cell) or to modify the production of a molecule to treat chronic pain. Such molecules can be produced by the cells upon introduction of heterologous nucleic acid molecules using techniques which are well known in the art.

In one embodiment, the cells of the invention can be modified to express the receptor of a neurotransmitter. In another embodiment, the cells of the invention are modified to produce a neurotransmitter. In yet another embodiment, the cells of the invention are modified to produce a fragment of a neurotransmitter, including but not limited to a fragment from the C' terminus or N' terminus. In another embodiment a foreign molecule enhances the neuroregenerative capacity of the administered cells, aids in reestablishing sensorineural communication of GABA interneurons, and/or aids in reestablishment of the excitatory/inhibitory neurotransmitter balance in the subject.

In yet another embodiment, the cells are genetically engineered to express and/or secret foreign molecules that promote success of administration (e.g., by downmodulation of an immune response in the subject), and/or promote survival or function of the administered cells. Exemplary molecules include, e.g., a neurotrophic factor, or a neuroprotective agent.

In yet another embodiment, unmodified or modified cells can be introduced together with other types of cells genetically modified to perform a useful function. For example, in order to promote growth of neurons the cells can be administered together with other cells which secrete or have been modified to secrete, for example, a neurotrophic factor. Examples of cells that act as carriers of transgenes to a subject include fibroblasts, adrenal chromaffin cells, astrocytes, and myoblasts. Such cells, for example fibroblasts and glial cells, can also be used to deliver retroviruses containing genes such as the herpes simplex thymidine kinase gene, the gene products of which are targets for other therapeutic drugs or agents such as ganciclovir to target cells.

Hosts cells may be transformed or transfected with DNA controlled by or in operative association with, one or more appropriate expression control elements such as promoter or enhancer sequences, transcription terminators, polyadenylation sites, among others, and a selectable marker. Any promoter may be used to drive the expression of the inserted gene. For example, viral promoters include, but are not limited to, the CMV promoter/enhancer, SV 40, papillomavirus, Epstein-Barr virus or elastin gene promoter. In some embodiments, the control elements used to control expression of the gene of interest can allow for the regulated expression of the gene so that the product is synthesized only when needed in vivo. If transient expression is desired, constitutive promoters are preferably used in a non-integrating and/or replication-defective vector. Alternatively, inducible promoters could be used to drive the expression of the inserted gene when necessary. Inducible promoters include, but are not limited to, those associated with metallothionein and heat shock proteins.

Following the introduction of the foreign DNA, engineered cells may be allowed to grow in enriched media and then switched to selective media. The selectable marker in the foreign DNA confers resistance to the selection and allows cells to stably integrate the foreign DNA as, for example, on a plasmid, into their chromosomes and grow to form foci which, in turn, can be cloned and expanded into cell lines. This method can be advantageously used to engineer cell lines that express the gene product.

The cells of the invention may be genetically engineered to "knock out" or "knock down" expression of factors that promote inflammation or rejection at the implant site. Negative modulatory techniques for the reduction of target gene expression levels or target gene product activity levels are discussed below. "Negative modulation," as used herein, refers to a reduction in the level and/or activity of target gene product relative to the level and/or activity of the target gene product in the absence of the modulatory treatment. The expression of a gene native to a neural cell, or progenitor cells thereof, can be reduced or knocked out using a number of techniques including, for example, inhibition of expression by inactivating the gene using the homologous recombination technique. Typically, an exon encoding an important region of the protein (or an exon 5' to that region) is interrupted by a positive selectable marker, e.g., neo, preventing the production of normal mRNA from the target gene and resulting in inactivation of the gene. A gene may also be inactivated by creating a deletion in part of a gene, or by deleting the entire gene. By using a construct with two regions of homology to the target gene that are far apart in the genome, the sequences intervening the two regions can be deleted as described by Mombaerts et al., 1991, *Proc. Nat. Acad. Sci. U.S.A.* 88:3084-3087, which is incorporated by reference in its entirety. Antisense, DNAzymes, ribozymes, small interfering RNA (siRNA) and other such molecules that inhibit expression of the target gene can also be used to reduce the level of target gene activity. For example, antisense RNA molecules that inhibit the expression of major histocompatibility gene complexes (HLA) have been shown to be most versatile with respect to immune responses. Still further, triple helix molecules can be utilized in reducing the level of target gene activity. These techniques are described in detail by L. G. Davis et al. (eds), 1994, BASIC METHODS IN MOLECULAR BIOLOGY, 2nd ed., Appleton & Lange, Norwalk, Conn., which is incorporated by reference in its entirety.

Cell Culture

The isolated cells may be used to initiate, or seed, cell cultures. Isolated cells are transferred to sterile tissue culture vessels either uncoated or coated with extracellular matrix or ligands such as laminin, collagen (native, denatured or crosslinked), gelatin, fibronectin, and other extracellular matrix proteins. The cells are cultured in any culture medium capable of sustaining growth of the cells such as, but not limited to, DMEM (high or low glucose), advanced DMEM, DMEM/MCDB 201, Eagle's basal medium, Ham's F10 medium (F10), Ham's F-12 medium (F12), Iscove's modified Dulbecco's medium, Mesenchymal Stem Cell growth medium (MSCGM), DMEM/F12, RPMI 1640, and serum/media free medium sold under the trade name CELL-GRO—FREE (Mediatech, Inc., Herndon, Va.). The culture medium may be supplemented with one or more components including, for example, fetal bovine serum (FBS), preferably about 2-15% (v/v); equine serum (ES); human serum (HS); beta-mercaptoethanol (BME or 2-ME), preferably about 0.001% (v/v); one or more growth factors, for example, platelet-derived growth factor (PDGF), epidermal growth factor (EGF), fibroblast growth factor (FGF), vascular endothelial growth factor (VEGF), insulin-like growth factor-1 (IGF-1), leukocyte inhibitory factor (LIF) and erythropoietin (EPO); amino acids, including L-valine; and one or more antibiotic and/or antimycotic agents to control microbial contamination, such as penicillin G, streptomycin sulfate, amphotericin B, gentamicin, and nystatin, either alone or in combination. The culture medium preferably comprises growth medium.

The cells are seeded in culture vessels at a density to allow cell growth. In a preferred embodiment, the cells are cultured at about 0 to about 5 percent by volume $CO_2$ in air. In some preferred embodiments, the cells are cultured at about 2 to about 25 percent $O_2$ in air, preferably about 5 to about 20 percent $O_2$ in air. The cells preferably are cultured at a temperature of about 25 to about 40° C. and more preferably are cultured at 37° C. The cells are preferably cultured in an incubator. The medium in the culture vessel can be static or agitated, for example, using a bioreactor. In some embodiments, the cells are grown under low oxidative stress (e.g., with addition of glutathione, Vitamin C, Catalase, Vitamin E, N-Acetylcysteine). "Low oxidative stress," as used herein, refers to conditions of no or minimal free radical damage to the cultured cells.

It should be apparent from the foregoing that an invention having significant advantages has been provided. While the invention is shown in only a few of its forms, it is not just limited but is susceptible to various changes and modifications without departing from the spirit thereof. In the spirit of the invention, the below examples are provided.

Example 1 hUTC in an Amyloid Infusion Model of Alzheimer's Disease

The objective of this study was to determine the efficacy of hUTC in an amyloid infusion model of Alzheimer's Disease (AD). The effect of administration of hUTC on memory, amyloid deposit and other measures of efficacy in the brain was evaluated after injection of amyloid protein. The rat amyloid-beta (Abeta) intracerebroventricular infusion can model aspects of AD. High density lipoprotein (HDL), a normal plasma carrier of Abeta, is used to attenuate Abeta aggregation causing Abeta-dependent toxicity and cognitive deficits. The rat in vivo infusion model is a useful, cost-effective method for screening new therapies for AD.

I. Methods & Materials

Sprague Dawley rats were implanted with a cannula and a delivery device. The animal's brains were infused with recombinant amyloid protein (experimental group) or phosphate buffer saline (sham control) for two weeks. The infusions ceased, and the animals were allowed to recover for one week. The cells were prepared at 100,000 cells/µl, and the animals were treated with a single injection via an ICV access cannula, 2 µl of 100,000 cells/µl solution or 5 µl of 100,000 cells/µl solution.

In total, there were five treatment groups:

Group 1 received an inert protein for two weeks then received a single injection of cell vehicle (saline) ("sham control").

Group 2 was treated with inert protein for two weeks and then a single injection of 500,000 hUTC.

Group 3 was treated with recombinant beta amyloid for two weeks and then cell vehicle (saline).

Group 4 was treated with recombinant beta amyloid and then a single injection of 200,000 test cells.

Group 5 treated with recombinant beta amyloid and then a single injection of 500,000 test cells.

The animals were allowed to recover from the procedures and evaluated through Morris Water Maze testing using a 2-meter diameter tank at a water temperature of 26° C., as described by Winkler et al., NeurobiolAging, 1994; 15(5): 601-607, which is incorporated by reference in its entirety. Distal stationary cues are placed around the walls of the room, and no proximal or mobile cues are present as experimenter was not visible to rats during trials. Prior to first trial of each day, the animals were placed on platform for 60 seconds for spatial orientation. The animals were removed from the platform, and heads covered with a drape until they were placed in a random start position, facing the tank wall. Animals were first trained for one and a half days in a visible platform test (4 trials per block, one block in the morning and another block in the afternoon; 3 blocks total). Hidden platform acquisition was then tested over the next five days (4 swim trials per block, two blocks per day). Animals were then given a Probe trial. To perform the Probe trial, the platform is removed from the tank and the rat is placed into the tank for 20 seconds. Long-term memory was tested by three days of acquisition in a reverse hidden platform position (4 trials per block, two blocks per day). This working memory was tested by changing the platform positions on the 6$^{th}$ and 7$^{th}$ days of testing. Following the last block of acquisition, there was another Probe trial. Path lengths and acquisition were determined by HVS image software and video tracking system HVS Image Ltd. (Buckingham, UK).

All animals were sacrificed 10 weeks after initiation of amyloid infusion (7 weeks after the infusion of hUTC). Animals were anesthetized with sodium pentobarbital and a cardiac perfusion with buffer containing protease inhibitors was performed. Tissues were collected for histology. The brains were separated sagittally, and one hemisphere was frozen for immunohistochemistry while the other was submersion fixed in 4% PFA followed by embedding in paraffin wax.

II. Results

On day 1, all treatment groups showed similar performance as evaluated by swim speed. Swim speeds ranged from 0.21 to 0.31 meters per second with means between 0.24 and 0.26. These results indicated no gross motor impairments from the implant procedures. (FIG. 1).

Figure 2:
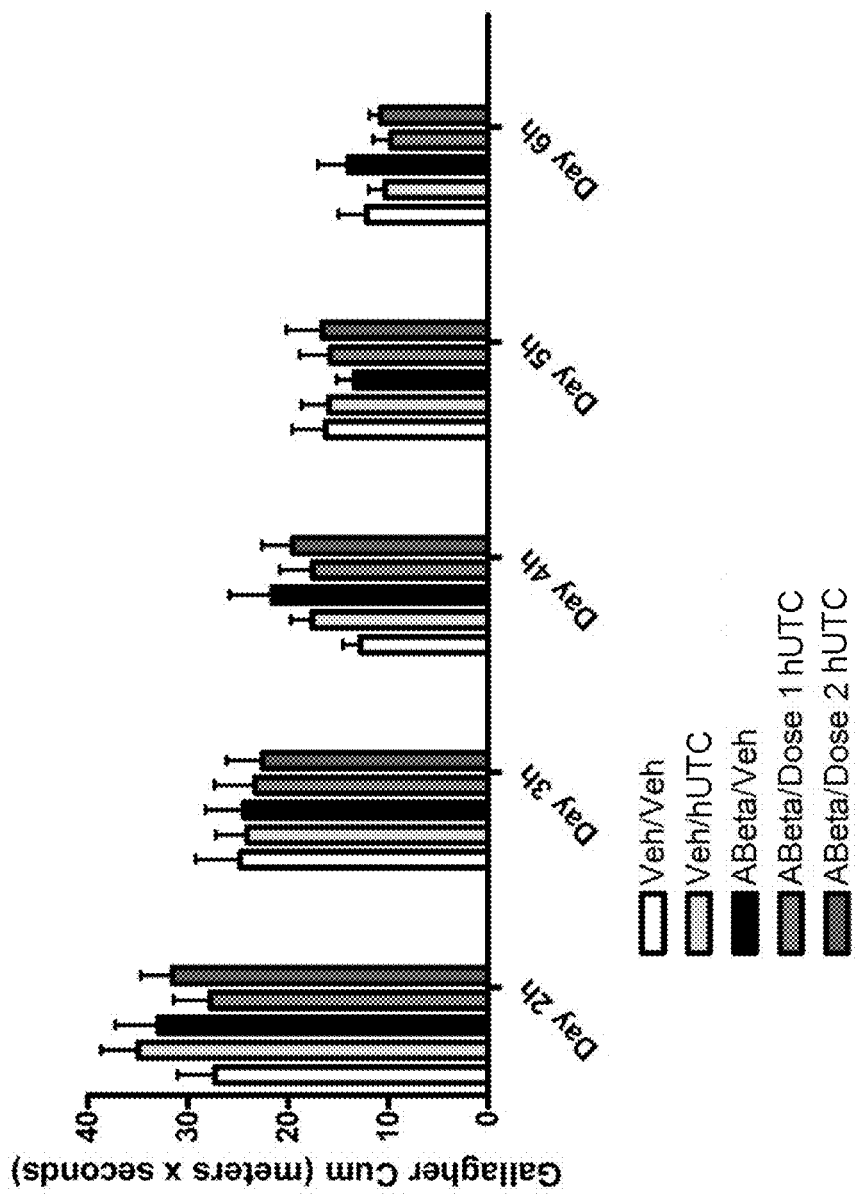
FIG. 2 shows the Gallagher Cumulative test scores for all treatment groups of rats treated with PBS or hUTC for hidden platform acquisition over time.
Figure 3:
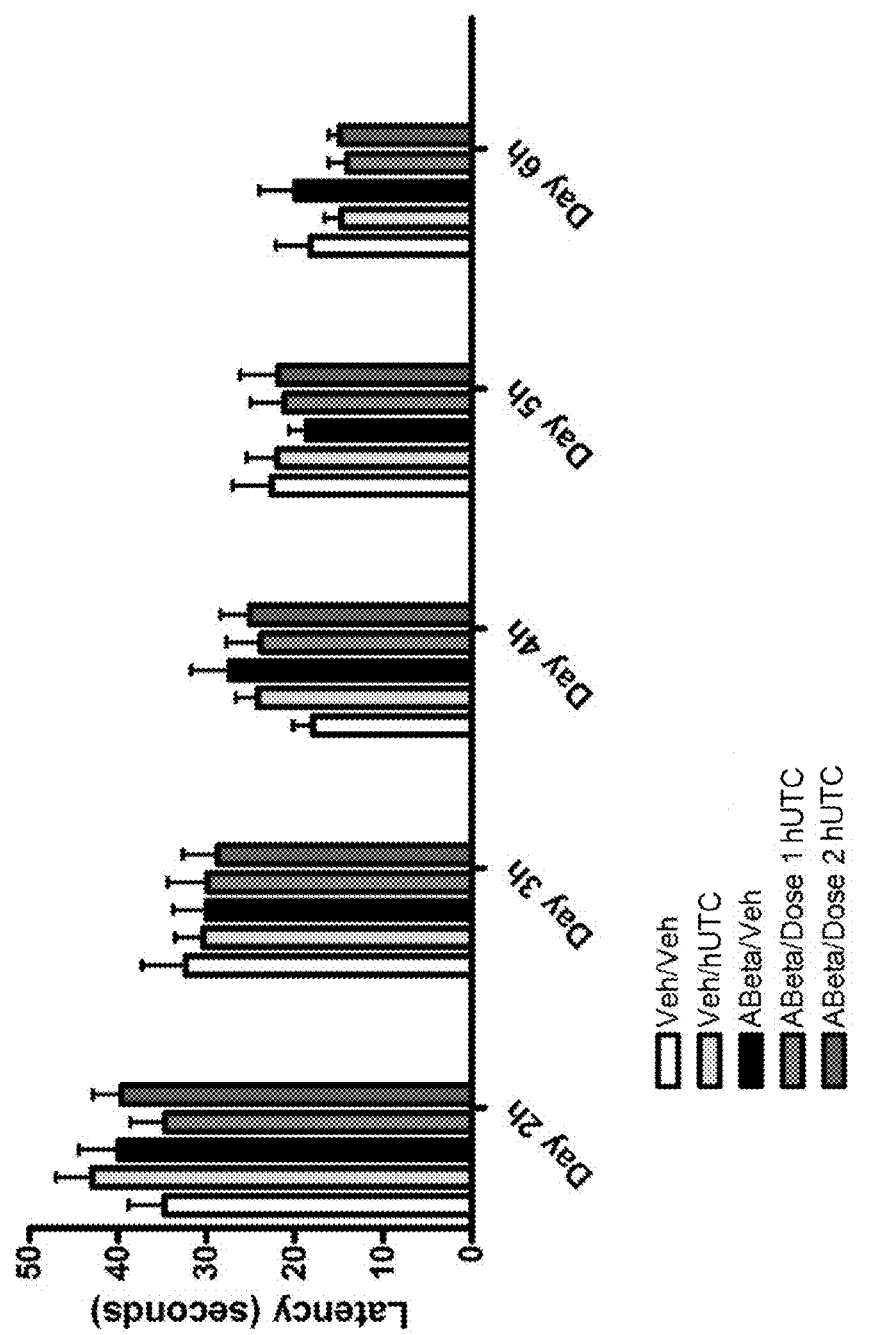
FIG. 3 shows the latency measurements for all treatment groups of rats treated with PBS or hUTC for hidden platform acquisition over time.

Hidden acquisition testing between days 2 through 6 also showed consistent performance across the treatment groups with swim speeds averaging between 0.25 and 0.30 meters per second. Measurements of Latency, that is the time it takes for the rat to find the platform, and scores in the Gallagher Cumulative testing showed consistent measurements across the treatment groups between days 2 and 5. (FIGS. 2 and 3).

Figure 4:
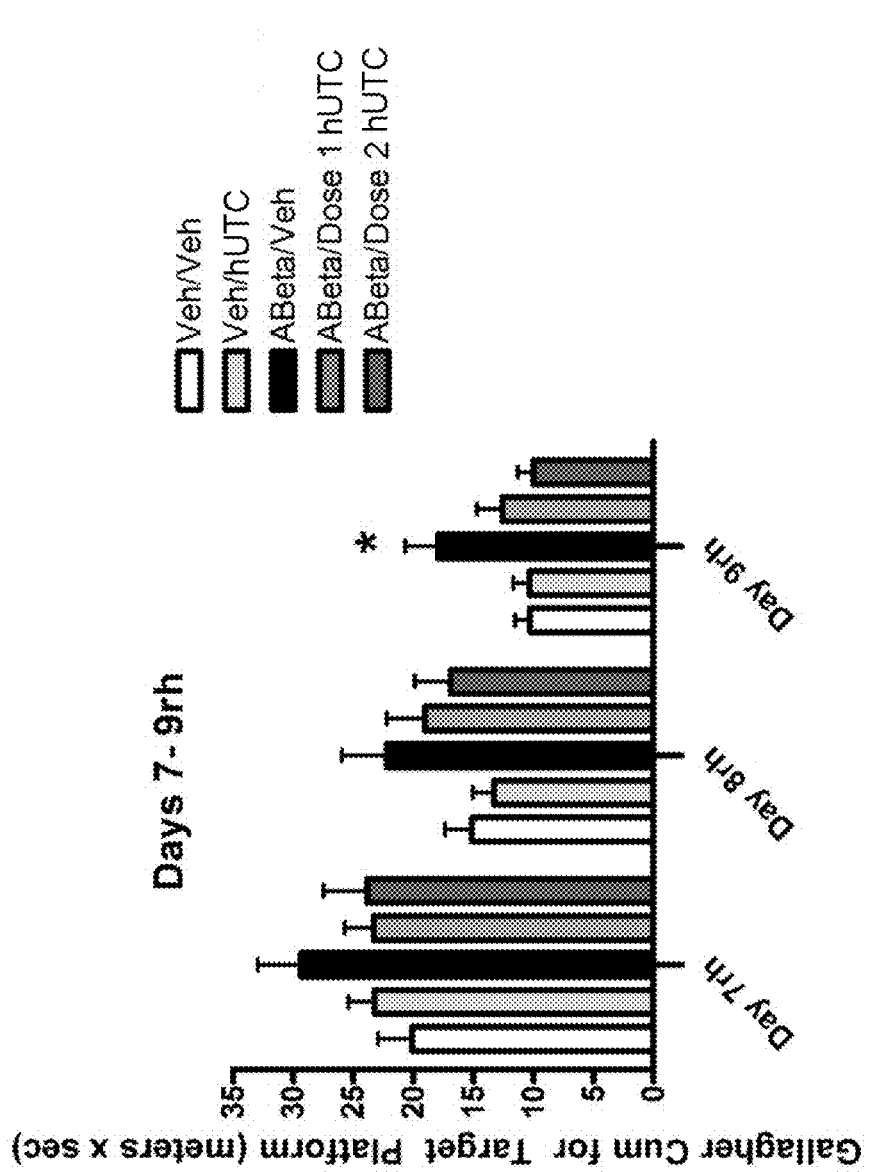
FIG. 4 are the Gallagher Cumulative test scores in reverse hidden platform acquisition for all treatment groups of rats treated with PBS or hUTC at days 7-9.
Figure 5:
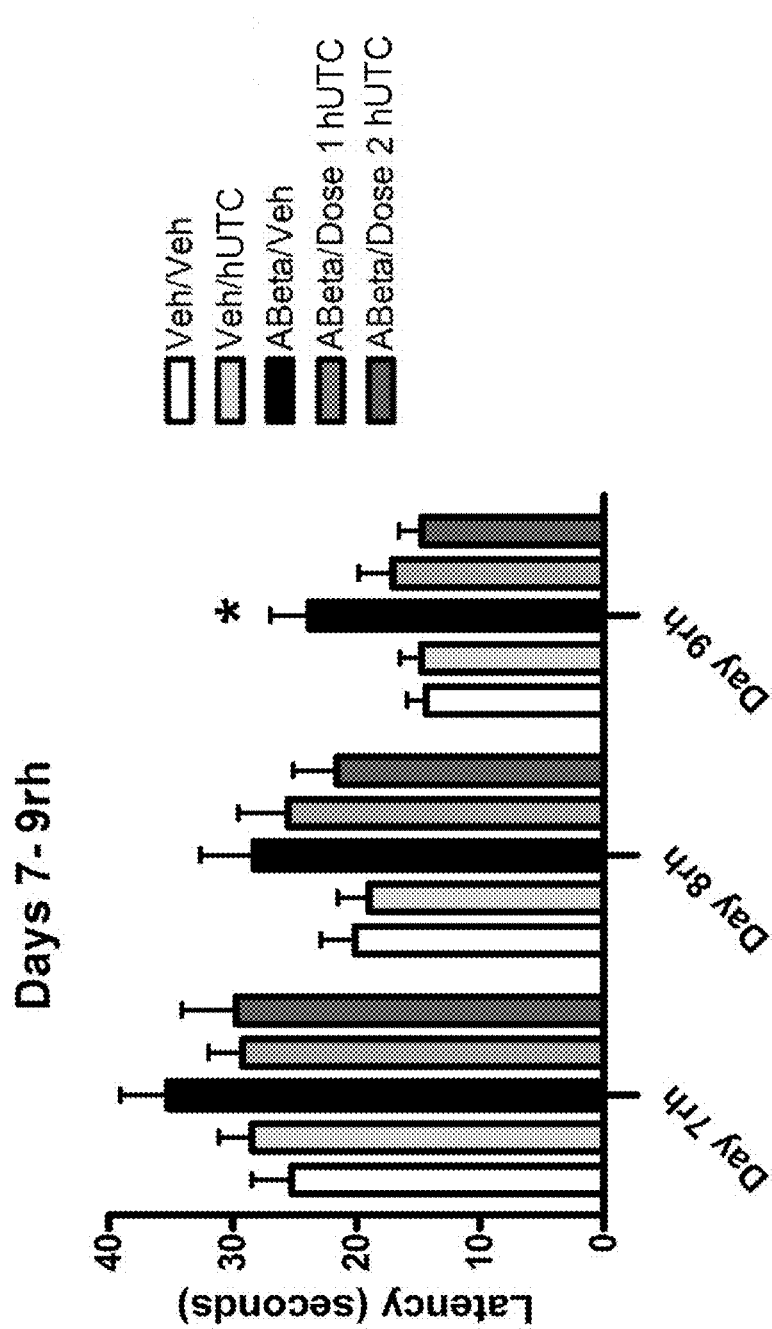
FIG. 5 are the latency measurements in reverse hidden platform acquisition for all treatment groups of rats treated with PBS or hUTC at days 7-9.

On days 5 and 6, Gallagher Cumulative scores are elevated in the Group 3 (amyloid with cell vehicle) animals as compared to the negative control (Group 1 and 2; vehicle with vehicle or vehicle with hUTC) as well as the cell treated cohorts (Groups 4 and 5). (FIG. 3). These differences were sustained through day 9 of the study and reached statistical significance for days 8 and 9. Group 3 scores were significantly higher than groups 1, 2 and 5. (FIG. 4). Similarly for latency measurements, although all groups had reduced latency over time, Group 3 had a significantly higher score than the other controls and treated cohorts. (FIG. 5).

In sum, the results evince amyloid treatment was effective and induced an injury, cell treatment in animals without injury did not elicit any negative response and cell treatment may reduce injury from locally administered amyloid protein.

Example 2 hUTC in a Genetic Model of Alzheimer's Disease

The objective of this study is to determine the efficacy of hUTC in a genetic model of Alzheimer's Disease.

I. Materials & Methods

Rodent models that carry deleted or added genes that may mimic the Alzheimer's Disease phenotype will be used. These animals may carry single or multiple mutations that will induce the accumulation and deposition of proteins in the brain that will lead to the alteration and possible accumulation of several proteins in the brain that will lead to the alteration and possible accumulation of several proteins such as amyloid and tau that accumulate in the brains of AD patients. Examples of these models include but are not limited to APP+PS1 double transgenic mice, presenillin knockout animals. (ApoE transgenic mice.) The accumulation of these proteins leads to the cell death and cognitive dysfunction. hUTC may be administered through direct injection into the brain or through systemic injection. Functional testing such as water maze performance or similar tests may evaluate the pathology and cell efficacy. Cells may be administered through a single injection or after multiple injections. These may be with or without immunosuppression drug therapy. The animals will be evaluated for several weeks after cell injection to clearly evaluate the magnitude and duration of cell efficacy. These animals will be evaluated by histology after necropsy. Tissues may be collected to evaluate amyloid accumulation and the presence of neurofibrillary tangles. Typical evaluations of cell viability and death may also be performed with tests such as TUNEL staining.

II. Results

Experiment will be analyzed using ANOVA. The treatment with hUTC is effective if there is significant improvement on the functional testing compared to controls. This may be established at a single or multiple time points. The histology results may show a reduced prevalence of amyloid or neurofibrillary tangles in cell treated animals as compared to control. This may be alone or observed in conjunction with a reduced prevalence of cells that exhibit key indicators of necrotic or apoptotic cell death such as TUNEL, pyknotic nuclei or active caspases. These markers may suggest that the cell-treated animals may have reduced pathology.

Example 3

Isolation of Cells

Postpartum umbilical cord and placenta were obtained upon birth of either a full term or pre-term pregnancy. Cells were harvested from five separate donors of umbilical cord and placental tissue. Different methods of cell isolation were tested for their ability to yield cells with: 1) the potential to differentiate into cells with different phenotypes, a characteristic common to stem cells, or 2) the potential to provide critical trophic factors useful for other cells and tissues.

Umbilical Cell Isolation.

Umbilical cords were obtained from National Disease Research Interchange (NDR1, Philadelphia, Pa.). The tissues were obtained following normal deliveries. The cell isolation protocols were performed aseptically in a laminar flow hood. To remove blood and debris, the cord was washed in phosphate buffered saline (PBS; Invitrogen, Carlsbad, Calif.) in the presence of penicillin at 100 Units/milliliter and streptomycin at 100 milligrams/milliliter, and amphotericin B at 0.25 micrograms/milliliter (Invitrogen Carlsbad, Calif.). The tissues were then mechanically dissociated in 150 cm$^2$ tissue culture plates in the presence of 50 milliliters of medium (DMEM-Low glucose or DMEM-High glucose; Invitrogen), until the tissue was minced into a fine pulp. The chopped tissues were transferred to 50 milliliter conical tubes (approximately 5 grams of tissue per tube).

The tissue was then digested in either DMEM-Low glucose medium or DMEM-High glucose medium, each containing 100 Units/milliliter, streptomycin at 100 milligrams/milliliter, and amphotericin B at 0.25 micrograms/milliliter and the digestion enzymes. In some experiments an enzyme mixture of collagenase and dispase was used ("C:D") (collagenase (Sigma, St Louis, Mo.), 500 Units/milliliter; and dispase (Invitrogen), 50 Units/milliliter, in DMEM-Low glucose medium). In other experiments a mixture of collagenase, dispase and hyaluronidase ("C:D:H") was used (C:D:H=collagenase, 500 Units/milliliter; dispase, 50 Units/milliliter; and hyaluronidase (Sigma), 5 Units/milliliter, in DMEM-Low glucose). The conical tubes containing the tissue, medium and digestion enzymes were incubated at 37° C. in an orbital shaker (Environ, Brooklyn, N.Y.) at 225 rpm for 2 hrs.

After digestion, the tissues were centrifuged at 150×g for 5 minutes, the supernatant was aspirated. The pellet was resuspended in 20 milliliters of growth medium (DMEM: Low glucose (Invitrogen), 15 percent (v/v) fetal bovine serum (FBS; defined fetal bovine serum; Lot #AND18475; Hyclone, Logan, Utah), 0.001% (v/v) 2-mercaptoethanol (Sigma), penicillin at 100 Units per milliliter, streptomycin at 100 micrograms per milliliter, and amphotericin B at 0.25 micrograms per milliliter; (each from Invitrogen, Carlsbad, Calif.)). The cell suspension was filtered through a 70-micron nylon BD FALCON Cell Strainer (BD Biosciences, San Jose, Calif.). An additional 5 milliliters rinse comprising growth medium was passed through the strainer. The cell suspension was then passed through a 40-micrometer nylon cell strainer (BD Biosciences, San Jose, Calif.) and chased with a rinse of an additional 5 milliliters of growth medium.

The filtrate was resuspended in growth medium (total volume 50 milliliters) and centrifuged at 150×g for 5 minutes. The supernatant was aspirated and the cells were resuspended in 50 milliliters of fresh growth medium. This process was repeated twice more.

After the final centrifugation, supernatant was aspirated and the cell pellet was resuspended in 5 milliliters of fresh growth medium. The number of viable cells was determined using trypan blue staining. Cells were then cultured under standard conditions.

The cells isolated from umbilical cord tissues were seeded at 5,000 cells/cm$^2$ onto gelatin-coated T-75 flasks (Corning Inc., Corning, N.Y.) in growth medium. After two days, spent medium and unadhered cells were aspirated from the flasks. Adherent cells were washed with PBS three times to remove debris and blood-derived cells. Cells were then replenished with growth medium and allowed to grow to confluence (about 10 days from passage 0) to passage 1. On subsequent passages (from passage 1 to 2 etc), cells reached sub-confluence (75-85 percent confluence) in 4-5 days. For these subsequent passages, cells were seeded at 5,000 cells/cm$^2$. Cells were grown in a humidified incubator with 5 percent carbon dioxide at 37° C.

Cells were isolated from umbilical cord tissues in DMEM-Low glucose medium with LIBERASE™ (2.5 milligrams per milliliter, Blendzyme 3™; Roche Applied Sciences, Indianapolis, Ind.) and hyaluronidase (5 Units/milliliter, Sigma). Digestion of the tissue and isolation of the cells was as described for other protease digestions above, however, the LIBERASE™/hyaluronidase mixture was used instead of the C:D or C:D:H enzyme mixture. Tissue digestion with LIBERASE™ resulted in the isolation of cell populations from postpartum tissues that expanded readily.

Procedures were compared for isolating cells from the umbilical cord using differing enzyme combinations. Enzymes compared for digestion included: i) collagenase; ii) dispase; iii) hyaluronidase; iv) collagenase:dispase mixture (C:D); v) collagenase:hyaluronidase mixture (C:H); vi) dispase:hyaluronidase mixture (D:H); and vii) collagenase:dispase:hyaluronidase mixture (C:D:H). Differences in cell isolation utilizing these different enzyme digestion conditions were observed (Table 3-1).

Other attempts were made to isolate pools of cells from umbilical cord by different approaches. In one instance umbilical cord was sliced and washed with growth medium to dislodge the blood clots and gelatinous material. The mixture of blood, gelatinous material and growth medium was collected and centrifuged at 150×g. The pellet was resuspended and seeded onto gelatin coated flasks in growth medium. From these experiments a cell population was isolated that readily expanded.

Cells have also been isolated from cord blood samples attained from NDR1. The isolation protocol used was that of International Patent Application WO 2003/025149 by Ho et al. (Ho, T. W., et al., "Cell Populations Which Co-Express CD49C and CD90," Application No. PCT/US02/29971, which is incorporated by reference in its entirety). Samples (50 milliliter and 10.5 milliliters, respectively) of umbilical cord blood (NDR1, Philadelphia Pa.) were mixed with lysis buffer (filter-sterilized 155 millimolar ammonium chloride, 10 millimolar potassium bicarbonate, 0.1 millimolar EDTA buffered to Ph 7.2 (all components from Sigma, St. Louis, Mo.)). Cells were lysed at a ratio of 1:20 cord blood to lysis buffer. The resulting cell suspension was vortexed for 5 seconds, and incubated for 2 minutes at ambient temperature. The lysate was centrifuged (10 minutes at 200×g). The cell pellet was resuspended in Complete Minimal Essential Medium (Gibco, Carlsbad Calif.) containing 10 percent fetal bovine serum (Hyclone, Logan Utah), 4 millimolar glutamine (Mediatech, Herndon, Va.), penicillin at 100 Units per milliliter and streptomycin at 100 micrograms per milliliter (Gibco, Carlsbad, Calif.). The resuspended cells were centrifuged (10 minutes at 200×g), the supernatant was aspirated, and the cell pellet was washed in complete medium. Cells were seeded directly into either T75 flasks (Corning, N.Y.), T75 laminin-coated flasks, or T175 fibronectin-coated flasks (both Becton Dickinson, Bedford, Mass.).

To determine whether cell populations could be isolated under different conditions and expanded under a variety of conditions immediately after isolation, cells were digested in growth medium with or without 0.001 percent (v/v) 2-mercaptoethanol (Sigma, St. Louis, Mo.), using the enzyme combination of C:D:H, according to the procedures provided above. All cells were grown in the presence of penicillin at 100 Units per milliliter and streptomycin at 100 micrograms per milliliter. Under all tested conditions cells attached and expanded well between passage 0 and 1 (Table 3-2). Cells in conditions 5-8 and 13-16 were demonstrated to proliferate well up to 4 passages after seeding at which point they were cryopreserved.

The combination of C:D:H, provided the best cell yield following isolation, and generated cells that expanded for many more generations in culture than the other conditions (Table 3-1). An expandable cell population was not attained using collagenase or hyaluronidase alone. No attempt was made to determine if this result is specific to the collagenase that was tested.

TABLE 3-1

Isolation of cells from umbilical cord tissue using varying enzyme combinations

| Enzyme Digest | Cells Isolated | Cell Expansion |
|---|---|---|
| Collagenase | X | X |
| Dispase | + (>10 h) | + |
| Hyaluronidase | X | X |
| Collagenase: Dispase | ++ (<3 h) | ++ |
| Collagenase: Hyaluronidase | ++ (<3 h) | + |
| Dispase: Hyaluronidase | + (>10 h) | + |
| Collagenase: Dispase: Hyaluronidase | +++ (<3 h) | +++ |

Key:
+ = good,
++ = very good,
+++ = excellent,
X = no success

Cells attached and expanded well between passage 0 and 1 under all conditions tested for enzyme digestion and growth (Table 3-2). Cells in experimental conditions 5-8 and 13-16 proliferated well up to 4 passages after seeding, at which point they were cryopreserved. All cells were cryopreserved for further analysis.

Nucleated cells attached and grew rapidly. These cells were analyzed by flow cytometry and were similar to cells obtained by enzyme digestion.

The preparations contained red blood cells and platelets. No nucleated cells attached and divided during the first 3 weeks. The medium was changed 3 weeks after seeding and no cells were observed to attach and grow.

Populations of cells could be isolated from umbilical tissue efficiently using the enzyme combination collagenase (a metalloprotease), dispase (neutral protease) and hyaluronidase (mucolytic enzyme which breaks down hyaluronic acid). LIBERASE™, which is a blend of collagenase and a neutral protease, may also be used. Blendzyme 3™, which is collagenase (4 Wunsch units/gram) and thermolysin (1714 casein Units/gram), was also used together with hyaluronidase to isolate cells. These cells expanded readily over many passages when cultured in growth expansion medium on gelatin coated plastic.

Cells were also isolated from residual blood in the cords, but not cord blood. The presence of cells in blood clots washed from the tissue, which adhere and grow under the conditions used, may be due to cells being released during the dissection process.

Example 4

Growth Characteristics of Postpartum-Derived Cells

The cell expansion potential of postpartum-derived cells was compared to other populations of isolated stem cells. The process of cell expansion to senescence is referred to as Hayflick's limit (Hayflick L., The longevity of cultured human cells. *J. Am. Geriatr. Soc.* 22(1):1-12, 1974; Hayflick L., The strategy of senescence. *Gerontologist* 14(1):37-45), 1974).

I. Materials and Methods

Gelatin-Coating Flasks.

Tissue culture plastic flasks were coated by adding 20 milliliters 2% (w/v) gelatin (Type B: 225 Bloom; Sigma, St Louis, Mo.) to a T75 flask (Corning Inc., Corning, N.Y.) for 20 minutes at room temperature. After removing the gelatin

TABLE 3-2

Isolation and culture expansion of postpartum cells under varying conditions:

| Condition | Medium | 15% FBS | BME | Gelatin | 20% O$_2$ | Growth Factors |
|---|---|---|---|---|---|---|
| 1 | DMEM-Lg | Y | Y | Y | Y | N |
| 2 | DMEM-Lg | Y | Y | Y | N (5%) | N |
| 3 | DMEM-Lg | Y | Y | N | Y | N |
| 4 | DMEM-Lg | Y | Y | N | N (5%) | N |
| 5 | DMEM-Lg | N (2%) | Y | N (Laminin) | Y | EGF/FGF (20 ng/ml) |
| 6 | DMEM-Lg | N (2%) | Y | N (Laminin) | N (5%) | EGF/FGF (20 ng/ml) |
| 7 | DMEM-Lg | N (2%) | Y | N (Fibronectin) | Y | PDGF/VEGF |
| 8 | DMEM-Lg | N (2%) | Y | N (Fibronectin) | N (5%) | PDGF/VEGF |
| 9 | DMEM-Lg | Y | N | Y | Y | N |
| 10 | DMEM-Lg | Y | N | Y | N (5%) | N |
| 11 | DMEM-Lg | Y | N | N | Y | N |
| 12 | DMEM-Lg | Y | N | N | N (5%) | N |
| 13 | DMEM-Lg | N (2%) | N | N (Laminin) | Y | EGF/FGF (20 ng/ml) |
| 14 | DMEM-Lg | N (2%) | N | N (Laminin) | N (5%) | EGF/FGF (20 ng/ml) |
| 15 | DMEM-Lg | N (2%) | N | N (Fibronectin) | Y | PDGF/VEGF |
| 16 | DMEM-Lg | N (2%) | N | N (Fibronectin) | N (5%) | PDGF/VEGF | solution, 10 milliliters phosphate-buffered saline (Pbs) (Invitrogen, Carlsbad, Calif.) were added and then aspirated.

Comparison of Expansion Potential of Postpartum-Derived Cells with Other Cell Populations.

For comparison of growth expansion potential the following cell populations were utilized; i) Mesenchymal stem cells (MSC; Cambrex, Walkersville, Md.); ii) Adipose-derived cells (U.S. Pat. No. 6,555,374 B1; U.S. Patent Application US20040058412); iii) Normal dermal skin fibroblasts (cc-2509 lot #9F0844; Cambrex, Walkersville, Md.); and iv) Umbilicus-derived cells. Cells were initially seeded at 5,000 cells/cm$^2$ on gelatin-coated T75 flasks in growth medium. For subsequent passages, cell cultures were treated as follows. After trypsinization, viable cells were counted after trypan blue staining. Cell suspension (50 microliters) was combined with trypan blue (50 microliters, Sigma, St. Louis Mo.). Viable cell numbers were estimated using a hemocytometer.

Following counting, cells were seeded at 5,000 cells/cm$^2$ onto gelatin-coated T 75 flasks in 25 milliliters of fresh growth medium. Cells were grown in a standard atmosphere (5 percent carbon dioxide (v/v)) at 37° C. The growth medium was changed twice per week. When cells reached about 85 percent confluence they were passaged; this process was repeated until the cells reached senescence.

At each passage, cells were trypsinized and counted. The viable cell yield, population doublings [ln(cells final/cells initial)/ln2], and doubling time (time in culture/population doubling) were calculated. For the purposes of determining optimal cell expansion, the total cell yield per passage was determined by multiplying the total yield for the previous passage by the expansion factor for each passage (i.e. expansion factor=cells final/cells initial).

Expansion Potential of Cell Banks at Low Density.

The expansion potential of cells banked at passage 10 was also tested. A different set of conditions was used. Normal dermal skin fibroblasts (cc-2509 lot #9F0844; Cambrex, Walkersville, Md.), umbilicus-derived cells, and placenta-derived cells were tested. These cell populations had been banked at passage 10 previously, having been cultured at 5,000 cells/cm$^2$ at each passage to that point. The effect of cell density on the cell populations following cell thaw at passage 10 was determined. Cells were thawed under standard conditions, counted using trypan blue staining. Thawed cells were then seeded at 1,000 cells/cm$^2$ in growth medium. Cells were grown under standard atmospheric conditions at 37° C. Growth medium was changed twice a week. Cells were passaged as they reached about 85% confluence. Cells were subsequently passaged until senescence, i.e., until they could not be expanded any further. Cells were trypsinized and counted at each passage. The cell yield, population doubling (ln(cells final/cells initial)/ln 2) and doubling time (time in culture)/population doubling). The total cell yield per passage was determined by multiplying total yield for the previous passage by the expansion factor for each passage (i.e., expansion factor=cells final/cells initial).

Expansion of Postpartum-Derived Cells at Low Density from Initial Cell Seeding.

The expansion potential of freshly isolated postpartum-derived cell cultures under low cell seeding conditions was tested in another experiment. Umbilicus-derived and placental-derived cells were isolated as described in a previous example. Cells were seeded at 1,000 cells/cm$^2$ and passaged as described above until senescence. Cells were grown under standard atmospheric conditions at 37° C. Growth medium was changed twice per week. Cells were passaged as they reached about 85% confluence. At each passage, cells were trypsinized and counted by trypan blue staining. The cell yield, population doubling (ln (cell final/cell initial)/ln 2) and doubling time (time in culture/population doubling) were calculated for each passage. The total cell yield per passage was determined by multiplying the total yield for the previous passage by the expansion factor for each passage (i.e. expansion factor=cell final/cell initial). Cells were grown on gelatin and non-gelatin coated flasks.

Expansion of Cells in Low Oxygen Culture Conditions.

It has been demonstrated that low $O_2$ cell culture conditions can improve cell expansion in certain circumstances (Csete, Marie; Doyle, John; Wold, Barbara J.; McKay, Ron; Studer, Lorenz. Low oxygen culturing of central nervous system progenitor cells. US20040005704). In order to determine if cell expansion of umbilicus-derived cells could be improved by altering cell culture conditions, cultures of postpartum-derived cells were grown in low oxygen conditions. Cells were seeded at 5,000 cells/cm$^2$ in growth medium on gelatin coated flasks. Cells were initially cultured under standard atmospheric conditions through passage 5, at which point they were transferred to low oxygen (5% $O_2$) culture conditions.

Other Growth Conditions.

In other experiments cells were expanded on non-coated, collagen-coated, fibronectin-coated, laminin-coated and matrigel-coated plates. Cultures have been demonstrated to expand well on these different matrices.

II. Results

Comparison of Expansion Potential of Postpartum-Derived Cells with Other Cell Populations.

Umbilicus-derived and placental-derived cells expanded for more than 40 passages generating cell yields of >1E17 cells in 60 days. In contrast, MSCs and fibroblasts senesced after <25 days and <60 days, respectively. Although both adipose-derived and omental cells expanded for almost 60 days they generated total cell yields of 4.5E12 and 4.24E13 respectively. Thus, when seeded at 5,000 cells/cm$^2$ under the experimental conditions utilized, postpartum-derived cells expanded much better than the other cell types grown under the same conditions (Table 4-1).

TABLE 4-1

Growth characteristics for different cell populations grown to senescence

| Cell Type | Senescence | Total Population Doublings | Yield (Total Cells) |
|---|---|---|---|
| MSC | 24 d | 8 | 4.72E7 |
| Adipose-derived cell | 57 d | 24 | 4.5E12 |
| Fibroblasts | 53 d | 26 | 2.82E13 |
| Umbilical | 65 d | 42 | 6.15E17 |
| Placental | 80 d | 46 | 2.4E19 |

Expansion of Potential of Cell Banks at Low Density.

Umbilicus-derived, placental-derived and fibroblast cells expanded for greater than 10 passages generating cell yields of >1E11 cells in 60 days (Table 4-2). After 60 days under these conditions, the fibroblasts became senesced; whereas the umbilicus-derived and placental-derived cell populations senesced after 80 days, completing >50 and >40 population doublings respectively.

TABLE 4-2

Growth characteristics for different cell populations using low density growth expansion from passage 10 through senescence

| Cell Type (Passage No.) | Senescence | Total Population Doublings | Yield (Total Cells) |
|---|---|---|---|
| Fibroblast (P10) | 80 days | 43.68 | 2.59E11 |
| Umbilical (P10) | 80 days | 53.6 | 1.25E14 |
| Placental | 60 days | 32.96 | 6.09E12 |

Expansion of Cells in Low Oxygen Culture Conditions.

Cells expanded well under the reduced oxygen conditions, however, culturing under low oxygen conditions does not appear to have a significant effect on cell expansion for postpartum-derived cells. Standard atmospheric conditions have already proven successful for growing sufficient numbers of cells, and low oxygen culture is not required for the growth of postpartum-derived cells.

Summary.

The current cell expansion conditions of growing isolated postpartum-derived cells at densities of about 5,000 cells/cm$^2$, in growth medium on gelatin-coated or uncoated flasks, under standard atmospheric oxygen, are sufficient to generate large numbers of cells at passage 11. Furthermore, the data suggests that the cells can be readily expanded using lower density culture conditions (e.g. 1,000 cells/cm$^2$). Postpartum-derived cell expansion in low oxygen conditions also facilitates cell expansion, although no incremental improvement in cell expansion potential has yet been observed when utilizing these conditions for growth. Presently, culturing postpartum-derived cells under standard atmospheric conditions is preferred for generating large pools of cells. However, when the culture conditions are altered, postpartum-derived cell expansion can likewise be altered. This strategy may be used to enhance the proliferative and differentiative capacity of these cell populations.

Under the conditions utilized, while the expansion potential of MSC and adipose-derived cells is limited, postpartum-derived cells expand readily to large numbers.

Example 5

Growth of Postpartum-derived Cells in Medium Containing D-Valine

It has been reported that medium containing D-valine instead of the normal L-valine isoform can be used to selectively inhibit the growth of fibroblast-like cells in culture (Hongpaisan, Inhibition of proliferation of contaminating fibroblasts by D-valine in cultures of smooth muscle cells from human myometrium. *Cell Biol Int.* 2000; 24:1-7; Sordillo et al., Culture of bovine mammary epithelial cells in D-valine modified medium: selective removal of contaminating fibroblasts. *Cell Biol Int Rep.* 1988; 12:355-64). Experiments were performed to determine whether postpartum-derived cells could grow in medium containing D-valine.

I. Methods & Materials

Placental-derived cells (P3), umbilicus-derived cells (P5) and fibroblasts (P9) were seeded at 5,000 cells/cm$^2$ in gelatin-coated T75 flasks (Corning, Corning, N.Y.). After 24 hours the medium was removed and the cells were washed with phosphate buffered saline (PBS) (Gibco, Carlsbad, Calif.) to remove residual medium. The medium was replaced with a modified growth medium (DMEM with D-valine (special order Gibco), 15% (v/v) dialyzed fetal bovine serum (Hyclone, Logan, Utah), 0.001% (v/v) beta-mercaptoethanol (Sigma), penicillin at 50 Units/milliliter and streptomycin at 50 milligrams/milliliter (Gibco)).

II. Results

Placental-derived, umbilicus-derived cells, and fibroblast cells seeded in the D-valine-containing medium did not proliferate, unlike cells seeded in growth medium containing dialyzed serum. Fibroblasts cells changed morphologically, increasing in size and changing shape. All of the cells died and eventually detached from the flask surface after four weeks. Thus, it may be concluded that postpartum-derived cells require L-valine for cell growth and to maintain long-term viability. L-valine is preferably not removed from the growth medium for postpartum-derived cells.

Example 6

Karyotype Analysis of PPDCs

Cell lines used in cell therapy are preferably homogeneous and free from any contaminating cell type. Human cells used in cell therapy should have a normal number (46) of chromosomes with normal structure. To identify postpartum-derived cell placental and umbilical cord lines that are homogeneous and free from cells of non-postpartum tissue origin, karyotypes of cell samples were analyzed.

I. Materials and Methods

PPDCs from postpartum tissue of a male neonate were cultured in Growth Media. Postpartum tissue from a male neonate (X,Y) was selected to allow distinction between neonatal-derived cells and maternal derived cells (X,X). Cells were seeded at 5,000 cells per square centimeter in growth medium in a T25 flask (Corning, Corning, N.Y.) and expanded to 80% confluence. A T25 flask containing cells was filled to the neck with Growth Media. Samples were delivered to a clinical cytogenetics lab by courier (estimated lab to lab transport time is one hour). Chromosome analysis was performed by the Center for Human & Molecular Genetics at the New Jersey Medical School, Newark, N.J. Cells were analyzed during metaphase when the chromosomes are best visualized. Of twenty cells in metaphase counted, five were analyzed for normal homogeneous karyotype number (two). A cell sample was characterized as homogeneous if two karyotypes were observed. A cell sample was characterized as heterogeneous if more than two karyotypes were observed. Additional metaphase cells were counted and analyzed when a heterogeneous karyotype number (four) was identified.

II. Results

All cell samples sent for chromosome analysis were interpreted by the cytogenetics laboratory staff as exhibiting a normal appearance. Three of the sixteen cell lines analyzed exhibited a heterogeneous phenotype (XX and XY) indicating the presence of cells derived from both neonatal and maternal origins (Table 6-1). Cells derived from tissue Placenta-N were isolated from the neonatal aspect of placenta. At passage zero, this cell line appeared homogeneous XY. However, at passage nine, the cell line was heterogeneous (XX/XY), indicating a previously undetected presence of cells of maternal origin. Each of the cell samples was characterized as homogeneous. (Table 6-1).

TABLE 6-1

Karyotype results of PPDCs.

| Tissue | Passage | Metaphase cells counted | Metaphase cells analyzed | Number of karyotypes | ISCN Karyotype |
|---|---|---|---|---|---|
| Placenta | 22 | 20 | 5 | 2 | 46, XX |
| Umbilical | 23 | 20 | 5 | 2 | 46, XX |
| Umbilical | 6 | 20 | 5 | 2 | 46, XY |
| Placenta | 2 | 20 | 5 | 2 | 46, XX |
| Umbilical | 3 | 20 | 5 | 2 | 46, XX |
| Placenta-N | 0 | 20 | 5 | 2 | 46, XY |
| Placenta-V | 0 | 20 | 5 | 2 | 46, XY |
| Placenta-M | 0 | 21 | 5 | 4 | 46, XY[18]/46, XX[3] |
| Placenta-M | 4 | 20 | 5 | 2 | 46, XX |
| Placenta-N | 9 | 25 | 5 | 4 | 46, XY[5]/46, XX[20] |
| Placenta-N C1 | 1 | 20 | 5 | 2 | 46, XY |
| Placenta-N C3 | 1 | 20 | 6 | 4 | 46, XY[2]/46, XX[18] |
| Placenta-N C4 | 1 | 20 | 5 | 2 | 46, XY |
| Placenta-N C15 | 1 | 20 | 5 | 2 | 46, XY |
| Placenta-N C20 | 1 | 20 | 5 | 2 | 46, XY |
| Placenta-N C22 | 1 | 20 | 5 | 2 | 46, XY |

Key:
N—Neonatal side;
V—villous region;
M—maternal side;
C—clone

Summary.

Chromosome analysis identified placental-derived and umbilicus-derived PPDCs whose karyotypes appear normal as interpreted by a clinical cytogenetic laboratory. Karyotype analysis also identified cell lines free from maternal cells, as determined by homogeneous karyotype.

Example 7

Flow Cytometric Evaluation of Human Postpartum-Derived Cell Surface Markers

Characterization of cell surface proteins or "markers" by flow cytometry can be used to determine a cell line's identity. The consistency of expression can be determined from multiple donors, and in cells exposed to different processing and culturing conditions. Postpartum cell lines isolated from the umbilicus were characterized by flow cytometry, providing a profile for the identification of these cell lines.

I. Materials and Methods

Media and Culture Vessels.

Cells were cultured in growth medium, in plasma-treated T75, T150, and T225 tissue culture flasks (Corning, Corning, N.Y.) until confluent. The growth surfaces of the flasks were coated with gelatin by incubating 2% (w/v) gelatin (Sigma, St. Louis, Mo.) for 20 minutes at room temperature.

Antibody Staining.

Adherent cells in flasks were washed in phosphate buffered saline (PBS); (Gibco, Carlsbad, Mo.) and detached with Trypsin/EDTA (Gibco). Cells were harvested, centrifuged, and resuspended in 3% (v/v) FBS in PBS at a cell concentration of $1 \times 10^7$ per milliliter. In accordance with the manufacture's specifications, antibody to the cell surface marker of interest (see below) was added to 100 microliters of cell suspension and the mixture was incubated in the dark for 30 minutes at 4° C. After incubation, cells were washed with PBS and centrifuged to remove unbound antibody. Cells were resuspended in 500 microliters PBS and analyzed by flow cytometry.

Flow Cytometry Analysis.

Flow cytometry analysis was performed with a FACScalibur™ instrument (Becton Dickinson, San Jose, Calif.).

Antibodies to Cell Surface Markers. The following antibodies to cell surface markers were used.

TABLE 7-1

Antibodies used in characterizing cell surface markers of UDCs.

| Antibody | Manufacture | Catalog Number |
|---|---|---|
| CD10 | BD Pharmingen (San Diego, CA) | 555375 |
| CD13 | BD Pharmingen (San Diego, CA) | 555394 |
| CD31 | BD Pharmingen (San Diego, CA) | 555446 |
| CD34 | BD Pharmingen (San Diego, CA) | 555821 |
| CD44 | BD Pharmingen (San Diego, CA) | 555478 |
| CD45RA | BD Pharmingen (San Diego, CA) | 555489 |
| CD73 | BD Pharmingen (San Diego, CA) | 550257 |
| CD90 | BD Pharmingen (San Diego, CA) | 555596 |
| CD117 | BD Biosciences (San Jose, CA) | 340529 |
| CD141 | BD Pharmingen (San Diego, CA) | 559781 |
| PDGFr-alpha | BD Pharmingen (San Diego, CA) | 556002 |
| HLA-A, B, C | BD Pharmingen (San Diego, CA) | 555553 |
| HLA-DR, DP, DQ | BD Pharmingen (San Diego, CA) | 555558 |
| IgG-FITC | Sigma (St. Louis, MO) | F-6522 |
| IgG-PE | Sigma (St. Louis, MO) | P-4685 |

Placenta- and Umbilical Cord-Derived Cell Comparison.

Placenta-derived cells were compared to umbilical cord-derived cells at passage 8.

Passage to Passage Comparison.

Placenta- and umbilical cord cells were analyzed at passages 8, 15, and 20.

Donor to Donor Comparison.

To compare differences among donors, placenta-derived cells from different donors were compared to each other, and umbilical cord-derived cells from different donors were compared to each other.

Surface Coating Comparison.

Placenta-derived cells cultured on gelatin-coated flasks were compared to placenta-derived cells cultured on uncoated flasks. Umbilical cord-derived cells cultured on gelatin-coated flasks were compared to umbilical cord-derived cells cultured on uncoated flasks.

II. Results

Digestion Enzyme Comparison. Four treatments used for isolation and preparation of cells were compared. Cells derived from postpartum tissue by treatment with 1) collagenase; 2) collagenase/dispase; 3) collagenase/hyaluronidase; and 4) collagenase/hyaluronidase/dispase were compared.

Placental Layer Comparison. Cells isolated from the maternal aspect of placental tissue were compared to cells isolated from the villous region of placental tissue and cells isolated from the neonatal fetal aspect of placenta.

Placenta-Derived Cells were Compared to Umbilical Cord-Derived Cells.

Placenta- and umbilical cord-derived cells analyzed by flow cytometry showed positive for production of CD10, CD13, CD44, CD73, CD90, PDGFr-alpha and HLA-A, B, C, indicated by the increased values of fluorescence relative to the IgG control. These cells were negative for detectable expression of CD31, CD34, CD45, CD117, CD141, and HLA-DR, DP, DQ, indicated by fluorescence values comparable to the IgG control. Variations in fluorescence values of positive curves were accounted. The mean (i.e., CD13) and range (i.e., CD90) of the positive curves showed some variation, but the curves appeared normal, confirming a homogeneous population. Both curves individually exhibited values greater than the IgG control.

Passage to Passage Comparison of Placenta-derived cells.

Placenta-derived cells at passages 8, 15, and 20 analyzed by flow cytometry all were positive for production of CD10, CD13, CD44, CD73, CD 90, PDGFr-alpha and HLA-A, B, C, as reflected in the increased value of fluorescence relative to the IgG control. The cells were negative for production of CD31, CD34, CD45, CD117, CD141, and HLA-DR, DP, DQ having fluorescence values consistent with the IgG control.

Passage to Passage Comparison of Umbilical Cord-Derived Cells.

Umbilical cord-derived cells at passage 8, 15, and 20 analyzed by flow cytometry all expressed CD10, CD13, CD44, CD73, CD 90, PDGFr-alpha and HLA-A, B, C, indicated by increased fluorescence relative to the IgG control. These cells were negative for CD31, CD34, CD45, CD117, CD141, and HLA-DR, DP, DQ, indicated by fluorescence values consistent with the IgG control.

Donor to Donor Comparison of Placenta-Derived Cells.

Placenta-derived cells isolated from separate donors analyzed by flow cytometry each expressed CD10, CD13, CD44, CD73, CD 90, PDGFr-alpha and HLA-A, B, C, with increased values of fluorescence relative to the IgG control. The cells were negative for production of CD31, CD34, CD45, CD117, CD141, and HLA-DR, DP, DQ as indicated by fluorescence value consistent with the IgG control.

Donor to Donor Comparison of Umbilical Cord-Derived Cells.

Umbilical cord-derived cells isolated from separate donors analyzed by flow cytometry each showed positive for production of CD10, CD13, CD44, CD73, CD 90, PDGFr-alpha and HLA-A, B, C, reflected in the increased values of fluorescence relative to the IgG control. These cells were negative for production of CD31, CD34, CD45, CD117, CD 141, and HLA-DR, DP, DQ with fluorescence values consistent with the IgG control.

The Effect of Surface Coating with Gelatin on Placenta-derived Cells.

Placenta-derived cells expanded on either gelatin-coated or uncoated flasks analyzed by flow cytometry all expressed of CD10, CD13, CD44, CD73, CD 90, PDGFr-alpha and HLA-A, B, C, reflected in the increased values of fluorescence relative to the IgG control. These cells were negative for production of CD31, CD34, CD45, CD117, CD141, and HLA-DR, DP, DQ indicated by fluorescence values consistent with the IgG control.

The Effect of Surface Coating with Gelatin on Umbilical Cord-Derived Cells.

Umbilical cord-derived cells expanded on gelatin and uncoated flasks analyzed by flow cytometry all were positive for production of CD10, CD13, CD44, CD73, CD 90, PDGFr-alpha and HLA-A, B, C, with increased values of fluorescence relative to the IgG control. These cells were negative for production of CD31, CD34, CD45, CD117, CD 141, and HLA-DR, DP, DQ, with fluorescence values consistent with the IgG control.

Evaluation of Effect of Enzyme Digestion Procedure Used for Preparation and Isolation of the Cells on the Cell Surface Marker Profile.

Placenta-Derived cells isolated using various digestion enzymes analyzed by flow cytometry all expressed CD10, CD13, CD44, CD73, CD 90, PDGFr-alpha and HLA-A, B, C, as indicated by the increased values of fluorescence relative to the IgG control. These cells were negative for production of CD31, CD34, CD45, CD117, CD141, and HLA-DR, DP, DQ as indicated by fluorescence values consistent with the IgG control.

Placental Layer Comparison.

Cells derived from the maternal, villous, and neonatal layers of the placenta, respectively, analyzed by flow cytometry showed positive for production of CD10, CD13, CD44, CD73, CD90, PDGFr-alpha and HLA-A, B, C, as indicated by the increased value of fluorescence relative to the IgG control. These cells were negative for production of CD31, CD34, CD45, CD117, CD141, and HLA-DR, DP, DQ as indicated by fluorescence values consistent with the IgG control.

Summary.

Analysis of placenta- and umbilical cord-derived postpartum cells by flow cytometry has established of an identity of these cell lines. Placenta- and umbilical cord-derived postpartum cells are positive for CD10, CD13, CD44, CD73, CD90, PDGFr-alpha, HLA-A,B,C and negative for CD31, CD34, CD45, CD117, CD141 and HLA-DR, DP, DQ. This identity was consistent between variations in variables including the donor, passage, culture vessel surface coating, digestion enzymes, and placental layer. Some variation in individual fluorescence value histogram curve means and ranges were observed, but all positive curves under all conditions tested were normal and expressed fluorescence values greater than the IgG control, thus confirming that the cells comprise a homogeneous population which has positive expression of the markers.

Example 8

Analysis of Cells by Oligonucleotide Array

Oligonucleotide arrays were used to compare gene expression profiles of umbilicus- and placenta-derived cells with fibroblasts, human mesenchymal stem cells, and another cell line derived from human bone marrow. This analysis provided a characterization of the postpartum-derived cells and identified unique molecular markers for these cells.

I. Materials and Methods

Isolation and Culture of Cells

Postpartum Tissue-Derived Cells.

Human umbilical cords and placenta were obtained from National Disease Research Interchange (NDR1, Philadelphia, Pa.) from normal full term deliveries with patient consent. The tissues were received and cells were isolated as described in Example 1. Cells were cultured in growth medium on gelatin-coated tissue culture plastic flasks. The cultures were incubated at 37° C. with 5% $CO_2$.

Fibroblasts.

Human dermal fibroblasts were purchased from Cambrex Incorporated (Walkersville, Md.; Lot number 9F0844) and ATCC CRL-1501 (CCD39SK). Both lines were cultured in DMEM/F12 medium (Invitrogen, Carlsbad, Calif.) with 10% (v/v) fetal bovine serum (Hyclone) and penicillin/streptomycin (Invitrogen)). The cells were grown on standard tissue-treated plastic.

Human Mesenchymal Stem Cells (hMSC).

hMSCs were purchased from Cambrex Incorporated (Walkersville, Md.; Lot numbers 2F1655, 2F1656 and 2F1657) and cultured according to the manufacturer's specifications in MSCGM Media (Cambrex). The cells were grown on standard tissue cultured plastic at 37° C. with 5% $CO_2$.

Human Iliac Crest Bone Marrow Cells (ICBM).

Human iliac crest bone marrow was received from NDR1 with patient consent. The marrow was processed according to the method outlined by Ho, et al. (WO03/025149). The marrow was mixed with lysis buffer (155 mM $NH_4Cl$, 10 mM $KHCO_3$, and 0.1 mM EDTA, pH 7.2) at a ratio of 1 part bone marrow to 20 parts lysis buffer. The cell suspension was vortexed, incubated for 2 minutes at ambient temperature, and centrifuged for 10 minutes at 500×g. The supernatant was discarded and the cell pellet was resuspended in Minimal Essential Medium-alpha (Invitrogen) supplemented with 10% (v/v) fetal bovine serum and 4 mM glutamine. The cells were centrifuged again and the cell pellet was resuspended in fresh medium. The viable mononuclear cells were counted using trypan-blue exclusion (Sigma, St. Louis, Mo.). The mononuclear cells were seeded in tissue-cultured plastic flasks at 5×10$^4$ cells/cm$^2$. The cells were incubated at 37° C. with 5% $CO_2$ at either standard atmospheric $O_2$ or at 5% $O_2$. Cells were cultured for 5 days without a media change. Media and non-adherent cells were removed after 5 days of culture. The adherent cells were maintained in culture.

Isolation of mRNA and GENECHIP Analysis.

Actively growing cultures of cells were removed from the flasks with a cell scraper in cold phosphate buffered saline (PBS). The cells were centrifuged for 5 minutes at 300×g. The supernatant was removed and the cells were resuspended in fresh PBS and centrifuged again. The supernatant was removed and the cell pellet was immediately frozen and stored at −80° C. Cellular mRNA was extracted and transcribed into cDNA. cDNA was then transcribed into cRNA and biotin-labeled. The biotin-labeled cRNA was hybridized with Affymetrix GENECHIP HG-U133A oligonucleotide arrays (Affymetrix, Santa Clara, Calif.). The hybridizations and data collection were performed according to the manufacturer's specifications. The hybridization and data collection was performed according to the manufacturer's specifications. Data analyses were performed using "Significance Analysis of Microarrays" (SAM) version 1.21 computer software (Tusher, V. G. et al., 2001, *Proc. Natl. Acad. Sci. USA* 98: 5116-5121). Licenses for the analysis software are available through the Office of Technology Licensing, Stanford University, and more information is available at Stanford University; Tusher, V. G. et al., 2001, Proc. Natl. Acad. Sci. USA 98: 5116-5121.

II. Results

Fourteen different populations of cells were analyzed in this study. The cells along with passage information, culture substrate, and culture media are listed in Table 8-1.

TABLE 8-1

Cells analyzed by the microarray study. The cells lines are listed by their identification code along with passage at the time of analysis, cell growth substrate, and growth media.

| | | | |
|---|---|---|---|
| Umbilical (022803) | 2 | Gelatin | DMEM, 15% FBS, βME |
| Umbilical (042103) | 3 | Gelatin | DMEM, 15% FBS, βME |
| Umbilical (071003) | 4 | Gelatin | DMEM, 15% FBS, βME |
| Placenta (042203) | 12 | Gelatin | DMEM, 15% FBS, βME |
| Placenta (042903) | 4 | Gelatin | DMEM, 15% FBS, βME |

TABLE 8-1-continued

Cells analyzed by the microarray study. The cells lines are listed by their identification code along with passage at the time of analysis, cell growth substrate, and growth media.

| | | | |
|---|---|---|---|
| Placenta (071003) | 3 | Gelatin | DMEM, 15% FBS, βME |
| ICBM (070203) (5% $O_2$) | 3 | Plastic | MEM 10% FBS |
| ICBM (062703) (std $O_2$) | 5 | Plastic | MEM 10% FBS |
| ICBM (062703)(5% $O_2$) | 5 | Plastic | MEM 10% FBS |
| hMSC (Lot 2F1655) | 3 | Plastic | MSCGM |
| hMSC (Lot 2F1656) | 3 | Plastic | MSCGM |
| hMSC (Lot 2F1657) | 3 | Plastic | MSCGM |
| hFibroblast (9F0844) | 9 | Plastic | DMEM-F12, 10% FBS |
| hFibroblast (CCD39SK) | 4 | Plastic | DMEM-F12, 10% FBS |

The data were evaluated by Principle Component Analysis with SAM software as described above. Analysis revealed 290 genes that were expressed in different relative amounts in the cells tested. This analysis provided relative comparisons between the populations.

Table 8-2 shows the Euclidean distances that were calculated for the comparison of the cell pairs. The Euclidean distances were based on the comparison of the cells based on the 290 genes that were differentially expressed among the cell types. The Euclidean distance is inversely proportional to similarity between the expression of the 290 genes.

TABLE 8-2

The Euclidean Distances for the Cell Pairs.
The Euclidean distance was calculated for the cell types using the 290 genes that were expressed differentially between the cell types. Similarity between the cells is inversely proportional to the Euclidean distance.

| Cell Pair | Euclidean Distance |
|---|---|
| ICBM-hMSC | 24.71 |
| Placenta-umbilical | 25.52 |
| ICBM-Fibroblast | 36.44 |
| ICBM-placenta | 37.09 |
| Fibroblast-MSC | 39.63 |
| ICBM-Umbilical | 40.15 |
| Fibroblast-Umbilical | 41.59 |
| MSC-Placenta | 42.84 |
| MSC-Umbilical | 46.86 |
| ICBM-placenta | 48.41 |

Tables 8-3, 8-4, and 8-5 show the expression of genes increased in placenta-derived cells (Table 8-3), increased in umbilical tissue-derived cells (Table 8-4), and reduced in umbilical cord and placenta-derived cells (Table 8-5).

TABLE 8-3

Genes which are specifically increased in expression in the placenta-derived cells as compared to the other cell lines assayed.
Genes Increased in Placenta-Derived Cells

| Probe Set ID | Gene Name | NCBI Accession Number |
|---|---|---|
| 209732_at | C-type (calcium dependent, carbohydrate-recognition domain) lectin, superfamily member 2 (activation-induced) | AF070642 |
| 206067_s_at | Wilms tumor 1 | NM_024426 |
| 207016_s_at | aldehyde dehydrogenase 1 family, member A2 | AB015228 |
| 206367_at | Renin | NM_000537 |
| 210004_at | oxidized low density lipoprotein (lectin-like) receptor 1 | AF035776 |
| 214993_at | *Homo sapiens*, clone IMAGE: 4179671, mRNA, partial cds | AF070642 |

TABLE 8-3-continued

Genes which are specifically increased in expression in the placenta-derived cells as compared to the other cell lines assayed.
Genes Increased in Placenta-Derived Cells

| Probe Set ID | Gene Name | NCBI Accession Number |
|---|---|---|
| 202178_at | protein kinase C, zeta | NM_002744 |
| 209780_at | hypothetical protein DKFZp564F013 | AL136883 |
| 204135_at | downregulated in ovarian cancer 1 | NM_014890 |
| 213542_at | Homo sapiens mRNA; cDNA DKFZp547K1113 (from clone DKFZp547K1113) | AI246730 |

TABLE 8-4

Genes which are specifically increased in expression in umbilical cord-derived cells as compared to the other cell lines assayed.
Genes Increased in Umbilicus-Derived Cells

| Probe Set ID | Gene Name | NCBI Accession Number |
|---|---|---|
| 202859_x_at | Interleukin 8 | NM_000584 |
| 211506_s_at | Interleukin 8 | AF043337 |
| 210222_s_at | reticulon 1 | BC000314 |
| 204470_at | chemokine (C—X—C motif) ligand 1 (melanoma growth stimulating activity | NM_001511 |
| 206336_at | chemokine (C—X—C motif) ligand 6 (granulocyte chemotactic protein 2) | NM_002993 |
| 207850_at | Chemokine (C—X—C motif) ligand 3 | NM_002090 |
| 203485_at | reticulon 1 | NM_021136 |
| 202644_s_at | tumor necrosis factor, alpha-induced protein 3 | NM_006290 |

TABLE 8-5

Genes which were decreased in expression in the umbilical cord and placenta cells as compared to the other cell lines assayed.
Genes Decreased in Umbilicus- and Placenta-Derived Cells

| Probe Set ID | Gene name | NCBI Accession Number |
|---|---|---|
| 210135_s_at | short stature homeobox 2 | AF022654.1 |
| 205824_at | heat shock 27 kDa protein 2 | NM_001541.1 |
| 209687_at | chemokine (C—X—C motif) ligand 12 (stromal cell-derived factor 1) | U19495.1 |
| 203666_at | chemokine (C—X—C motif) ligand 12 (stromal cell-derived factor 1) | NM_000609.1 |
| 212670_at | elastin (supravalvular aortic stenosis, Williams-Beuren syndrome) | AA479278 |
| 213381_at | Homo sapiens mRNA; cDNA DKFZp586M2022 (from clone DKFZp586M2022) | N91149 |
| 206201_s_at | mesenchyme homeobox 2 (growth arrest-specific homeobox) | NM_005924.1 |
| 205817_at | Sine oculis homeobox homolog 1 (Drosophila) | NM_005982.1 |
| 209283_at | crystallin, alpha B | AF007162.1 |
| 212793_at | dishevelled associated activator of morphogenesis 2 | BF513244 |
| 213488_at | DKFZP586B2420 protein | AL050143.1 |
| 209763_at | similar to neuralin 1 | AL049176 |
| 205200_at | Tetranectin (plasminogen binding protein) | NM_003278.1 |
| 205743_at | src homology three (SH3) and cysteine rich domain | NM_003149.1 |
| 200921_s_at | B-cell translocation gene 1, anti-proliferative | NM_001731.1 |
| 206932_at | cholesterol 25-hydroxylase | NM_003956.1 |
| 204198_s_at | runt-related transcription factor 3 | AA541630 |
| 219747_at | hypothetical protein FLJ23191 | NM_024574.1 |
| 204773_at | Interleukin 11 receptor, alpha | NM_004512.1 |
| 202465_at | Procollagen C-endopeptidase enhancer | NM_002593.2 |
| 203706_s_at | Frizzled homolog 7 (Drosophila) | NM_003507.1 |
| 212736_at | hypothetical gene BC008967 | BE299456 |
| 214587_at | Collagen, type VIII, alpha 1 | BE877796 |
| 201645_at | Tenascin C (hexabrachion) | NM_002160.1 |
| 210239_at | iroquois homeobox protein 5 | U90304.1 |
| 203903_s_at | Hephaestin | NM_014799.1 |
| 205816_at | integrin, beta 8 | NM_002214.1 |
| 203069_at | synaptic vesicle glycoprotein 2 | NM_014849.1 |
| 213909_at | Homo sapiens cDNA FLJ12280 fis, clone MAMMA1001744 | AU147799 |
| 206315_at | cytokine receptor-like factor 1 | NM_004750.1 |
| 204401_at | potassium intermediate/small conductance calcium-activated channel, subfamily N, member 4 | NM_002250.1 |
| 216331_at | integrin, alpha 7 | AK022548.1 |
| 209663_s_at | integrin, alpha 7 | AF072132.1 |
| 213125_at | DKFZP586L151 protein | AW007573 |
| 202133_at | transcriptional co-activator with PDZ-binding motif (TAZ) | AA081084 |
| 206511_s_at | Sine oculis homeobox homolog 2 (Drosophila) | NM_016932.1 |
| 213435_at | KIAA1034 protein | AB028957.1 |
| 206115_at | early growth response 3 | NM_004430.1 |
| 213707_s_at | distal-less homeobox 5 | NM_005221.3 |
| 218181_s_at | hypothetical protein FLJ20373 | NM_017792.1 |
| 209160_at | aldo-keto reductase family 1, member C3 (3-alpha hydroxysteroid dehydrogenase, type II) | AB018580.1 |
| 213905_x_at | Biglycan | AA845258 |
| 201261_x_at | Biglycan | BC002416.1 |
| 202132_at | transcriptional co-activator with PDZ-binding motif (TAZ) | AA081084 |
| 214701_s_at | fibronectin 1 | AJ276395.1 |

TABLE 8-5-continued

Genes which were decreased in expression in the umbilical cord and placenta cells as compared to the other cell lines assayed.
Genes Decreased in Umbilicus- and Placenta-Derived Cells

| Probe Set ID | Gene name | NCBI Accession Number |
|---|---|---|
| 213791_at | Proenkephalin | NM_006211.1 |
| 205422_s_at | Integrin, beta-like 1 (with EGF-like repeat domains) | NM_004791.1 |
| 214927_at | *Homo sapiens* mRNA full length insert cDNA clone EUROIMAGE 1968422 | AL359052.1 |
| 206070_s_at | EphA3 | AF213459.1 |
| 212805_at | KIAA0367 protein | AB002365.1 |
| 219789_at | natriuretic peptide receptor C/guanylate cyclase C (atrionatriuretic peptide receptor C) | AI628360 |
| 219054_at | hypothetical protein FLJ14054 | NM_024563.1 |
| 213429_at | *Homo sapiens* mRNA; cDNA DKFZp564B222 (from clone DKFZp564B222) | AW025579 |
| 204929_s_at | vesicle-associated membrane protein 5 (myobrevin) | NM_006634.1 |
| 201843_s_at | EGF-containing fibulin-like extracellular matrix protein 1 | NM_004105.2 |
| 221478_at | BCL2/adenovirus E1B 19 kDa interacting protein 3-like | AL132665.1 |
| 201792_at | AE binding protein 1 | NM_001129.2 |
| 204570_at | cytochrome c oxidase subunit VIIa polypeptide 1 (muscle) | NM_001864.1 |
| 201621_at | neuroblastoma, suppression of tumorigenicity 1 | NM_005380.1 |
| 202718_at | Insulin-like growth factor binding protein 2, 36 kDa | NM_000597.1 |

Tables 8-6, 8-7, and 8-8 show the expression of genes increased in human fibroblasts (Table 8-6), ICBM cells (Table 8-7), and MSCs (Table 8-8).

TABLE 8-6

Genes which were increased in expression in fibroblasts as compared to the other cell lines assayed.
Genes increased in fibroblasts dual specificity phosphatase 2
KIAA0527 protein
*Homo sapiens* cDNA: FLJ23224 fis, clone ADSU02206
dynein, cytoplasmic, intermediate polypeptide 1
ankyrin 3, node of Ranvier (ankyrin G)
inhibin, beta A (activin A, activin AB alpha polypeptide)
ectonucleotide pyrophosphatase/phosphodiesterase 4 (putative function)
KIAA1053 protein
microtubule-associated protein 1A
zinc finger protein 41
HSPC019 protein
*Homo sapiens* cDNA: FLJ23564 fis, clone LNG10773
*Homo sapiens* mRNA; cDNA DKFZp564A072 (from clone DKFZp564A072)
LIM protein (similar to rat protein kinase C-binding enigma)
inhibitor of kappa light polypeptide gene enhancer in B-cells, kinase complex-associated protein
hypothetical protein FLJ22004
Human (clone CTG-A4) mRNA sequence
ESTs, Moderately similar to cytokine receptor-like factor 2; cytokine receptor CRL2 precursor [*Homo sapiens*]
transforming growth factor, beta 2
hypothetical protein MGC29643
antigen identified by monoclonal antibody MRC OX-2

TABLE 8-7

Genes which were increased in expression in the ICBM-derived cells as compared to the other cell lines assayed.
Genes Increased In ICBM Cells cardiac ankyrin repeat protein
MHC class I region ORF
integrin, alpha 10
hypothetical protein FLJ22362
UDP-N-acetyl-alpha-D-galactosamine:polypeptide N-acetylgalactosaminyltransferase 3 (GalNAc-T3)
interferon-induced protein 44
SRY (sex determining region Y)-box 9 (campomelic dysplasia, autosomal sex-reversal)
keratin associated protein 1-1
hippocalcin-like 1
jagged 1 (Alagille syndrome)
proteoglycan 1, secretory granule

TABLE 8-8

Genes which were increased in expression in the MSC cells as compared to the other cell lines assayed.
Genes Increased In MSC Cells interleukin 26
maltase-glucoamylase (alpha-glucosidase)
nuclear receptor subfamily 4, group A, member 2
v-fos FBJ murine osteosarcoma viral oncogene homolog
hypothetical protein DC42
nuclear receptor subfamily 4, group A, member 2
FBJ murine osteosarcoma viral oncogene homolog B
WNT1 inducible signaling pathway protein 1
MCF.2 cell line derived transforming sequence
potassium channel, subfamily K, member 15
cartilage paired-class homeoprotein 1
*Homo sapiens* cDNA FLJ12232 fis, clone MAMMA1001206
*Homo sapiens* cDNA FLJ34668 fis, clone LIVER2000775
jun B proto-oncogene
B-cell CLL/lymphoma 6 (zinc finger protein 51)
zinc finger protein 36, C3H type, homolog (mouse)

Summary.

The present study was performed to provide a molecular characterization of the postpartum cells derived from umbilical cord and placenta. This analysis included cells derived from three different umbilical cords and three different placentas. The study also included two different lines of dermal fibroblasts, three lines of mesenchymal stem cells, and three lines of iliac crest bone marrow cells. The mRNA that was expressed by these cells was analyzed on a GENECHIP oligonucleotide array that contained oligonucleotide probes for 22,000 genes.

The analysis revealed that transcripts for 290 genes were present in different amounts in these five different cell types. These genes include ten genes that are specifically increased in the placenta-derived cells and seven genes specifically increased in the umbilical tissue-derived cells. Fifty-four genes were found to have specifically lower expression levels in placenta and umbilical cord.

The expression of selected genes has been confirmed by PCR, as shown in Example 7. Postpartum-derived cells generally, and umbilical derived cells, in particular, have distinct gene expression profiles, for example, as compared to other human cells, such as the bone marrow-derived cells and fibroblasts tested here.

Example 9

Cell Markers in Postpartum Derived Cells

Gene expression profiles of cells derived from the human placenta and umbilical cord were compared with those of cells derived from other sources using an Affymetrix GENECHIP. Six "signature" genes were identified: oxidized LDL receptor 1, interleukin-8 (IL-8), renin, reticulon, chemokine receptor ligand 3 (CXC ligand 3), and granulocyte chemotactic protein 2 (GCP-2). These "signature" genes were expressed at relatively high levels in umbilicus-derived cells.

The procedures described in this example were conducted to verify the microarray data and compare data for gene and protein expression, as well as to establish a series of reliable assays for detection of unique identifiers for postpartum-derived cells.

I. Methods & Materials

Cells.

Placenta-derived cells (three isolates, including one isolate predominately neonatal (as determined by karyotype analysis), umbilicus-derived cells (four isolates), and Normal Human Dermal Fibroblasts (NHDF; neonatal and adult) were grown in growth medium in gelatin-coated T75 flasks. Mesenchymal Stem Cells (MSCs) were grown in Mesenchymal Stem Cell Growth Medium Bullet kit (MSCGM; Cambrex, Walkerville, Md.).

For IL-8 experiments, cells were thawed from liquid nitrogen and plated in gelatin-coated flasks at 5,000 cells/$cm^2$, grown for 48 hours in growth medium and then grown further for 8 hours in 10 milliliters of serum starvation medium [DMEM-low glucose (Gibco, Carlsbad, Calif.), penicillin (50 Units/milliliter), streptomycin (50 micrograms/milliliter)(Gibco) and 0.1% (w/v) Bovine Serum Albumin (BSA; Sigma, St. Louis, Mo.)]. RNA was then extracted and the supernatants were centrifuged at 150×g for 5 minutes to remove cellular debris. Supernatants were frozen at −80° C. until ELISA analysis.

Cell Culture for ELISA Assay.

Postpartum Cells derived from human placenta and umbilical cord, as well as human fibroblasts derived from human neonatal foreskin, were cultured in growth medium in gelatin-coated T75 flasks. Cells were frozen at passage 11 in liquid nitrogen. Cells were thawed and transferred to 15 milliliter centrifuge tubes. After centrifugation at 150×g for 5 minutes, the supernatant was discarded. Cells were resuspended in 4 milliliters culture medium and counted. Cells were grown in a 75 $cm^2$ flask containing 15 milliliters of growth medium at 375,000 cell/flask for 24 hours. The medium was changed to a serum starvation medium for 8 hours. Serum starvation medium was collected at the end of incubation, centrifuged at 14,000×g for 5 minutes (and stored at −20° C.).

To estimate the number of cells in each flask, 2 milliliters of trypsin/EDTA (Gibco, Carlsbad, Calif.) were added each flask. After cells detached from the flask, trypsin activity was neutralized with 8 milliliters of growth medium. Cells were transferred to a 15 milliliter centrifuge tube and centrifuged at 150×g for 5 minutes. Supernatant was removed and 1 milliliter growth medium was added to each tube to resuspend the cells. Cell number was determined with a hemocytometer.

ELISA Assay.

The amount of IL-8 secreted by the cells into serum starvation medium was analyzed using ELISA assays (R&D Systems, Minneapolis, Minn.). All assays were conducted according to the instructions provided by the manufacturer.

Total RNA isolation.

RNA was extracted from confluent postpartum-derived cells and fibroblasts, or for IL-8 expression, from cells treated as described above. Cells were lysed with 350 microliters buffer RLT containing beta-mercaptoethanol (Sigma, St. Louis, Mo.) according to the manufacturer's instructions (RNeasy® Mini Kit; Qiagen, Valencia, Calif.). RNA was extracted according to the manufacturer's instructions (RNeasy® Mini Kit; Qiagen, Valencia, Calif.) and subjected to DNase treatment (2.7 Units/sample) (Sigma St. Louis, Mo.). RNA was eluted with 50 microliters DEPC-treated water and stored at −80° C. RNA was also extracted from human umbilical cord. Tissue (30 milligrams) was suspended in 700 microliters of buffer RLT containing beta-mercaptoethanol. Samples were mechanically homogenized and the RNA extraction proceeded according to manufacturer's specification. RNA was extracted with 50 microliters of DEPC-treated water and stored at −80° C.

Reverse Transcription.

RNA was reverse-transcribed using random hexamers with the TaqMan™ reverse transcription reagents (Applied Biosystems, Foster City, Calif.) at 25° C. for 10 minutes, 37° C. for 60 minutes, and 95° C. for 10 minutes. Samples were stored at −20° C.

Genes identified by cDNA microarray as uniquely regulated in postpartum cells (signature genes—including oxidized LDL receptor, interleukin-8, renin, and reticulon), were further investigated using real-time and conventional PCR.

Real-Time PCR.

PCR was performed on cDNA samples using gene expression products sold under the tradename ASSAYS-ON-DEMAND (Applied Biosystems) gene expression products. Oxidized LDL receptor (Hs00234028); renin (Hs00166915); reticulon (Hs00382515); CXC ligand 3 (Hs00171061); GCP-2 (Hs00605742); IL-8 (Hs00174103); and GAPDH were mixed with cDNA and TaqMan™ Universal PCR master mix according to the manufacturer's instructions (Applied Biosystems) using a 7000 sequence detection system with ABI Prism 7000 SDS software (Applied Biosystems). Thermal cycle conditions were initially 50° C. for 2 minutes and 95° C. for 10 minutes, followed by 40 cycles of 95° C. for 15 seconds and 60° C. for 1 minute. PCR data were analyzed according to manufacturer's specifications (User Bulletin #2 from Applied Biosystems for ABI Prism 7700 Sequence Detection System).

Conventional PCR.

Conventional PCR was performed using an ABI PRISM 7700 (Perkin Elmer Applied Biosystems, Boston, Mass.) to confirm the results from real-time PCR. PCR was performed using 2 microliters of cDNA solution (1× Taq polymerase (tradename AMPLITAQ GOLD) universal mix PCR reaction buffer (Applied Biosystems) and initial denaturation at 94° C. for 5 minutes. Amplification was optimized for each primer set. For IL-8, CXC ligand 3, and reticulon (94° C. for 15 seconds, 55° C. for 15 seconds and 72° C. for 30 seconds for 30 cycles); for renin (94° C. for 15 seconds, 53° C. for 15 seconds and 72° C. for 30 seconds for 38 cycles); for oxidized LDL receptor and GAPDH (94° C. for 15 seconds, 55° C. for 15 seconds and 72° C. for 30 seconds for 33 cycles). Primers used for amplification are listed in Table 9-1. Primer concentration in the final PCR reaction was 1 micromolar except for GAPDH which was 0.5 micromolar. GAPDH primers were the same as for real-time PCR, except that the manufacturer's TaqMan™ probe was not added to the final PCR reaction. Samples were separated on 2% (w/v) agarose gel and stained with ethidium bromide (Sigma, St. Louis, Mo.). Images were captured on 667 film (Universal Twinpack, VWR International, South Plainfield, N.J.) using a fixed focal-length POLAROID camera (VWR International, South Plainfield, N.J.).

TABLE 9-1

Primers used

| Primer name | Primers |
|---|---|
| Oxidized LDL receptor | S: 5'-GAGAAATCCAAAGAGCAAATGG-3 (SEQ ID NO: 1) |
|  | A: 5'-AGAATGGAAAACTGGAATAGG-3' (SEQ ID NO: 2) |
| Renin | S: 5'-TCTTCGATGCTTCGGATTCC-3' (SEQ ID NO: 3) |
|  | A: 5'-GAATTCTCGGAATCTCTGTTG-3' (SEQ ID NO: 4) |
| Reticulon | S: 5'-TTACAAGCAGTGCAGAAAACC-3' (SEQ ID NO: 5) |
|  | A: 5'-AGTAAACATTGAAACCACAGCC-3' (SEQ ID NO: 6) |
| Interleukin-8 | S: 5'-TCTGCAGCTCTGTGTGAAGG-3' (SEQ ID NO: 7) |
|  | A: 5'-CTTCAAAAACTTCTCCACAACC-3' (SEQ ID NO: 8) |
| Chemokine (CXC) ligand 3 | S: 5'-CCCACGCCACGCTCTCC-3' (SEQ ID NO: 9) |
|  | A: 5'-TCCTGTCAGTTGGTGCTCC-3' (SEQ ID NO: 10) |

Immunofluorescence.

Postpartum-derived cells were fixed with cold 4% (w/v) paraformaldehyde (Sigma-Aldrich, St. Louis, Mo.) for 10 minutes at room temperature. One isolate each of umbilical cord- and placenta-derived cells at passage 0 (P0) (directly after isolation) and passage 11 (P11) (two isolates of Placenta-derived, two isolates of Umbilical cord-derived cells) and fibroblasts (P11) were used. Immunocytochemistry was performed using antibodies directed against the following epitopes:vimentin (1:500, Sigma, St. Louis, Mo.), desmin (1:150; Sigma—raised against rabbit; or 1:300; Chemicon, Temecula, Calif.—raised against mouse), alpha-smooth muscle actin (SMA; 1:400; Sigma), cytokeratin 18 (CK18; 1:400; Sigma), von Willebrand Factor (vWF; 1:200; Sigma), and CD34 (human CD34 Class III; 1:100; DAKOCytomation, Carpinteria, Calif.). In addition, the following markers were tested on passage 11 postpartum-derived cells: anti-human GROalpha—PE (1:100; Becton Dickinson, Franklin Lakes, N.J.), anti-human GCP-2 (1:100; Santa Cruz Biotech, Santa Cruz, Calif.), anti-human oxidized LDL receptor 1 (ox-LDL R1; 1:100; Santa Cruz Biotech), and anti-human NOGO-A (1:100; Santa Cruz, Biotech).

Cultures were washed with phosphate-buffered saline (PBS) and exposed to a protein blocking solution containing PBS, 4% (v/v) goat serum (Chemicon, Temecula, Calif.), and 0.3% (v/v) Triton (Triton X-100; Sigma, St. Louis, Mo.) for 30 minutes to access intracellular antigens. Where the epitope of interest was located on the cell surface (CD34, ox-LDL R1), Triton X-100 was omitted in all steps of the procedure in order to prevent epitope loss. Furthermore, in instances where the primary antibody was raised against goat (GCP-2, ox-LDL R1, NOGO-A), 3% (v/v) donkey serum was used in place of goat serum throughout the process. Primary antibodies, diluted in blocking solution, were then applied to the cultures for a period of 1 hour at room temperature. The primary antibody solutions were removed and the cultures were washed with PBS prior to application of secondary antibody solutions (1 hour at room temperature) containing block along with goat anti-mouse IgG—Texas Red (1:250; Molecular Probes, Eugene, Oreg.) and/or goat anti-rabbit IgG—Alexa 488 (1:250; Molecular Probes) or donkey anti-goat IgG—FITC (1:150, Santa Cruz Biotech). Cultures were then washed and 10 micromolar DAPI (Molecular Probes) applied for 10 minutes to visualize cell nuclei.

Following immunostaining, fluorescence was visualized using an appropriate fluorescence filter on an Olympus inverted epi-fluorescent microscope (Olympus, Melville, N.Y.). In all cases, positive staining represented fluorescence signal above control staining where the entire procedure outlined above was followed with the exception of application of a primary antibody solution (no 1° control). Representative images were captured using a digital color video-camera and ImagePro software (Media Cybernetics, Carlsbad, Calif.). For triple-stained samples, each image was taken using only one emission filter at a time. Layered montages were then prepared using Adobe Photoshop software (Adobe, San Jose, Calif.).

Preparation of Cells for FACS Analysis.

Adherent cells in flasks were washed in phosphate buffered saline (PBS) (Gibco, Carlsbad, Calif.) and detached with Trypsin/EDTA (Gibco, Carlsbad, Calif.). Cells were harvested, centrifuged, and re-suspended 3% (v/v) FBS in PBS at a cell concentration of $1 \times 10^7$/milliliter. One hundred microliter aliquots were delivered to conical tubes. Cells stained for intracellular antigens were permeabilized with Perm/Wash buffer (BD Pharmingen, San Diego, Calif.). Antibody was added to aliquots as per manufacturer's specifications, and the cells were incubated for in the dark for 30 minutes at 4° C. After incubation, cells were washed with PBS and centrifuged to remove excess antibody. Cells requiring a secondary antibody were resuspended in 100 microliter of 3% FBS. Secondary antibody was added as per manufacturer's specification, and the cells were incubated in the dark for 30 minutes at 4° C. After incubation, cells were washed with PBS and centrifuged to remove excess secondary antibody. Washed cells were resuspended in 0.5 milliliter PBS and analyzed by flow cytometry. The following antibodies were used: oxidized LDL receptor 1 (sc-5813; Santa Cruz, Biotech), GROα (555042; BD Pharmingen, Bedford, Mass.), Mouse IgG1 kappa, (P-4685 and M-5284; Sigma), and Donkey against Goat IgG (sc-3743; Santa Cruz, Biotech.).

FACS analysis. Flow cytometry analysis was performed with FACScalibur™ (Becton Dickinson San Jose, Calif.).

II. Results

Results of real-time PCR for selected "signature" genes performed on cDNA from cells derived from human umbilical cord, adult and neonatal fibroblasts, and Mesenchymal Stem Cells (MSCs) indicate that both reticulon and oxidized LDL receptor expression were higher in umbilicus-derived cells as compared to other cells. The data obtained from real-time PCR were analyzed by the AACT method and expressed on a logarithmic scale. No significant differences in the expression levels of CXC ligand 3 and GCP-2 were found between postpartum cells and controls. The results of real-time PCR were confirmed by conventional PCR. Sequencing of PCR products further validated these observations. No significant difference in the expression level of CXC ligand 3 was found between postpartum cells and controls using conventional PCR CXC ligand 3 primers listed in Table 9-1.

The expression of the cytokine, IL-8 in postpartum cells was elevated in both growth medium-cultured and serum-starved postpartum-derived cells. All real-time PCR data were validated with conventional PCR and by sequencing PCR products.

After growth in serum-free media, the conditioned media were examined for the presence of IL-8. The greatest amounts of IL-8 were detected in media in which umbilical cells and some isolates of placenta-derived cells had been grown (Table 9-2). No IL-8 was detected in medium in which human dermal fibroblasts had been grown.

TABLE 9-2

IL-8 protein expression measured by ELISA

| Cell type | IL-8 |
|---|---|
| Human fibroblasts | ND |
| Placenta Isolate 1 | ND |
| UMBC Isolate 1 | 2058.42 ± 144.67 |
| Placenta Isolate 2 | ND |
| UMBC Isolate 2 | 2368.86 ± 22.73 |
| Placenta Isolate3 (normal $O_2$) | 17.27 ± 8.63 |
| Placenta Isolate 3 (low$O_2$, W/O BME) | 264.92 ± 9.88 |

Results of the ELISA assay for interleukin-8 (IL-8) performed on placenta- and umbilical cord-derived cells as well as human skin fibroblasts. Values are presented here are picogram/million cells, n = 2, sem.
ND: Not Detected Placenta-derived cells were also examined for the expression of oxidized LDL receptor, GCP-2, and GROalpha by FACS analysis. Cells tested positive for GCP-2. Oxidized LDL receptor and GRO were not detected by this method.

Placenta-derived cells were also tested for the production of selected proteins by immunocytochemical analysis. Immediately after isolation (passage 0), cells derived from the human placenta were fixed with 4% paraformaldehyde and exposed to antibodies for six proteins: von Willebrand Factor, CD34, cytokeratin 18, desmin, alpha-smooth muscle actin, and vimentin. Cells stained positive for both alpha-smooth muscle actin and vimentin. This pattern was preserved through passage 11. Only a few cells (<5%) at passage 0 stained positive for cytokeratin 18.

Cells derived from the human umbilical cord at passage 0 were probed for the production of selected proteins by immunocytochemical analysis. Immediately after isolation (passage 0), cells were fixed with 4% paraformaldehyde and exposed to antibodies for six proteins: von Willebrand Factor, CD34, cytokeratin 18, desmin, alpha-smooth muscle actin, and vimentin. Umbilical cord-derived cells were positive for alpha-smooth muscle actin and vimentin, with the staining pattern consistent through passage 11.

Placenta-derived cells at passage 11 were also investigated by immunocytochemistry for the production of GROalpha and GCP-2. Placenta-derived cells were GCP-2 positive, but GROalpha production was not detected by this method.

The production of GROalpha, GCP-2, oxidized LDL receptor 1 and reticulon (NOGO-A) in umbilical cord-derived cells at passage 11 was investigated by immunocytochemistry. Umbilical cord-derived cells were GCP-2 positive, but GRO alpha production was not detected by this method. Furthermore, cells were NOGO-A positive.

Summary.

Accordance between gene expression levels measured by microarray and PCR (both real-time and conventional) has been established for four genes: oxidized LDL receptor 1, renin, reticulon, and IL-8. The expression of these genes was differentially regulated at the mRNA level in postpartum-derived cells, with IL-8 also differentially regulated at the protein level. The presence of oxidized LDL receptor was not detected at the protein level by FACS analysis in cells derived from the placenta. Differential expression of GCP-2 and CXC ligand 3 was not confirmed at the mRNA level; however, GCP-2 was detected at the protein level by FACS analysis in the placenta-derived cells. Although this result does not support data originally obtained from the microarray experiment, this may be due to a difference in the sensitivity of the methodologies.

Immediately after isolation (passage 0), cells derived from the human placenta stained positive for both alpha-smooth muscle actin and vimentin. This pattern was also observed in cells at passage 11. These results suggest that vimentin and alpha-smooth muscle actin expression may be preserved in cells with passaging, at least in the growth medium used here.

Cells derived from the human umbilical cord at passage 0 were probed for the expression of alpha-smooth muscle actin and vimentin. and were positive for both. The staining pattern was preserved through passage 11.

In conclusion, the complete mRNA data at least partially verifies the data obtained from the microarray experiments.

Example 10

Immunohistochemical Characterization of PPDC Phenotypes

The phenotypes of cells found within human postpartum tissue (placenta and umbilical cord) was analyzed by immunohistochemistry.

I. Materials & Methods

Tissue Preparation.

Human umbilical cord and placenta tissue was harvested and immersion fixed in 4% (w/v) paraformaldehyde overnight at 4° C. Immunohistochemistry was performed using antibodies directed against the following epitopes (see Table $10^{-1}$): vimentin (1:500; Sigma, St. Louis, Mo.), desmin (1:150, raised against rabbit; Sigma; or 1:300, raised against mouse; Chemicon, Temecula, Calif.), alpha-smooth muscle actin (SMA; 1:400; Sigma), cytokeratin 18 (CK18; 1:400; Sigma), von Willebrand Factor (vWF; 1:200; Sigma), and CD34 (human CD34 Class III; 1:100; DAKOCytomation, Carpinteria, Calif.). In addition, the following markers were tested: anti-human GROalpha-PE (1:100; Becton Dickinson, Franklin Lakes, N.J.), anti-human GCP-2 (1:100; Santa Cruz Biotech, Santa Cruz, Calif.), anti-human oxidized LDL receptor 1 (ox-LDL R1; 1:100; Santa Cruz Biotech), and anti-human NOGO-A (1:100; Santa Cruz Biotech). Fixed specimens were trimmed with a scalpel and placed within OCT embedding compound (Tissue-Tek OCT; Sakura, Torrance, Calif.) on a dry ice bath containing ethanol. Frozen blocks were then sectioned (10 microns thick) using a standard cryostat (Leica Microsystems) and mounted onto glass slides for staining.

Immunohistochemistry.

Immunohistochemistry was performed similar to previous studies (e.g., Messina, et al. (2003) *Exper. Neurol.* 184: 816-829). Tissue sections were washed with phosphate-buffered saline (PBS) and exposed to a protein blocking solution containing PBS, 4% (v/v) goat serum (Chemicon, Temecula, Calif.), and 0.3% (v/v) Triton (Triton X-100; Sigma) for 1 hour to access intracellular antigens. In instances where the epitope of interest would be located on the cell surface (CD34, ox-LDL R1), triton was omitted in all steps of the procedure in order to prevent epitope loss. Furthermore, in instances where the primary antibody was raised against goat (GCP-2, ox-LDL R1, NOGO-A), 3% (v/v) donkey serum was used in place of goat serum throughout the procedure. Primary antibodies, diluted in blocking solution, were then applied to the sections for a period of 4 hours at room temperature. Primary antibody solutions were removed, and cultures washed with PBS prior to application of secondary antibody solutions (1 hour at room temperature) containing block along with goat anti-mouse IgG-Texas Red (1:250; Molecular Probes, Eugene, Oreg.) and/or goat anti-rabbit IgG-Alexa 488 (1:250; Molecular Probes) or donkey anti-goat IgG-FITC (1:150; Santa Cruz Biotech). Cultures were washed, and 10 micromolar DAPI (Molecular Probes) was applied for 10 minutes to visualize cell nuclei.

Following immunostaining, fluorescence was visualized using the appropriate fluorescence filter on an Olympus inverted epifluorescent microscope (Olympus, Melville, N.Y.). Positive staining was represented by fluorescence signal above control staining. Representative images were captured using a digital color videocamera and ImagePro software (Media Cybernetics, Carlsbad, Calif.). For triple-stained samples, each image was taken using only one emission filter at a time. Layered montages were then prepared using Adobe Photoshop software (Adobe, San Jose, Calif.).

TABLE 10-1

Summary of Primary Antibodies Used

| Antibody | Concentration | Vendor |
| --- | --- | --- |
| Vimentin | 1:500 | Sigma, St. Louis, MO |
| Desmin (rb) | 1:150 | Sigma |
| Desmin (m) | 1:300 | Chemicon, Temecula, CA |
| alpha-smooth muscle actin (SMA) | 1:400 | Sigma |
| Cytokeratin 18 (CK18) | 1:400 | Sigma |
| von Willebrand factor (vWF) | 1:200 | Sigma |
| CD34 III | 1:100 | DakoCytomation, Carpinteria, CA |
| GROalpha-PE | 1:100 | BD, Franklin Lakes, NJ |
| GCP-2 | 1:100 | Santa Cruz Biotech |
| Ox-LDL R1 | 1:100 | Santa Cruz Biotech |
| NOGO-A | 1:100 | Santa Cruz Biotech |

II. Results

Umbilical Cord Characterization.

Vimentin, desmin, SMA, CK18, vWF, and CD34 markers were expressed in a subset of the cells found within umbilical cord (data not shown). In particular, vWF and CD34 expression were restricted to blood vessels contained within the cord. CD34+ cells were on the innermost layer (lumen side). Vimentin expression was found throughout the matrix and blood vessels of the cord. SMA was limited to the matrix and outer walls of the artery & vein, but not contained with the vessels themselves. CK18 and desmin were observed within the vessels only, desmin being restricted to the middle and outer layers.

Placenta Characterization.

Vimentin, desmin, SMA, CK18, vWF, and CD34 were all observed within the placenta and regionally specific.

GROalpha, GCP-2, ox-LDL R1, and NOGO-A Tissue Expression.

None of these markers were observed within umbilical cord or placental tissue (data not shown).

Summary.

Vimentin, desmin, alpha-smooth muscle actin, cytokeratin 18, von Willebrand Factor, and CD 34 are expressed in cells within human umbilical cord and placenta. Based on in vitro characterization studies showing that only vimentin and alpha-smooth muscle actin are expressed, the data suggests that the current process of postpartum-derived cell isolation harvests a subpopulation of cells or that the cells isolated change expression of markers to express vimentin and alpha-smooth muscle actin.

Example 11

Secretion of Trophic Factors by Postpartum-Derived Cells

The secretion of selected trophic factors from placenta- and umbilicus-derived PPDCs was measured. Factors were selected that have angiogenic activity (i.e., hepatocyte growth factor (HGF) (Rosen et al. (1997) *Ciba Found. Symp.* 212:215-26), monocyte chemotactic protein 1 (MCP-1) (Salcedo et al. (2000) *Blood* 96; 34-40), interleukin-8 (IL-8) (Li et al. (2003) *J. Immunol.* 170:3369-76), keratinocyte growth factor (KGF), basic fibroblast growth factor (bFGF), vascular endothelial growth factor (VEGF) (Hughes et al. (2004) *Ann. Thorac. Surg.* 77:812-8), tissue inhibitor of matrix metalloproteinase 1 (TIMP1), angiopoietin 2 (ANG2), platelet derived growth factor (PDGFbb), thrombopoietin (TPO), heparin-binding epidermal growth factor (HB-EGF), stromal-derived factor 1alpha (SDF-1alpha)), neurotrophic/neuroprotective activity (brain-derived neurotrophic factor (BDNF) (Cheng et al. (2003) *Dev. Biol.* 258; 319-33), interleukin-6 (IL-6), granulocyte chemotactic protein-2 (GCP-2), transforming growth factor beta2 (TGFbeta2)), or chemokine activity (macrophage inflammatory protein 1alpha (MIP1alpha), macrophage inflammatory protein 1 beta (MIP 1beta), monocyte chemoattractant-1 (MCP-1), Rantes (regulated on activation, normal T cell expressed and secreted), 1309, thymus and activation-regulated chemokine (TARC), Eotaxin, macrophage-derived chemokine (MDC), IL-8).

I. Methods & Materials

Cell culture. PPDCs derived from placenta and umbilical cord, as well as human fibroblasts derived from human neonatal foreskin, were cultured in growth medium on gelatin-coated T75 flasks. Cells were cryopreserved at passage 11 and stored in liquid nitrogen. After thawing, growth medium was added to the cells, followed by transfer to a 15 milliliter centrifuge tube and centrifugation of the cells at 150×g for 5 minutes. The cell pellet was resuspended in 4 milliliters growth medium, and cells were counted. Cells were seeded at 5,000 cells/cm$^2$ in T75 flasks each containing 15 milliliters of growth medium, and cultured for 24 hours. The medium was changed to a serum-free medium (DMEM-low glucose (Gibco), 0.1% (w/v) bovine serum albumin (Sigma), penicillin (50 Units/milliliter) and streptomycin (50 micrograms/milliliter, Gibco)) for 8 hours. Conditioned serum-free medium was collected at the end of incubation by centrifugation at 14,000×g for 5 minutes and stored at −20° C.

To estimate the number of cells in each flask, cells were washed with phosphate-buffered saline (PBS) and detached using 2 milliliters trypsin/EDTA (Gibco). Trypsin activity was inhibited by addition of 8 milliliters growth medium. Cells were centrifuged at 150×g for 5 minutes. The supernatant was removed, and cells were resuspended in 1 milliliter growth medium. Cell number was estimated with a hemocytometer.

ELISA Assay.

Cells were grown at 37° C. in 5% carbon dioxide and atmospheric oxygen. The amount of MCP-1, IL-6, VEGF, SDF-1alpha, GCP-2, IL-8, and TGF-beta2 produced by each cell sample was determined by ELISA (R&D Systems, Minneapolis, Minn.). All assays were performed according to the manufacturer's instructions. Values presented are picograms per milliliter per million cells (n=2, sem).

SEARCHLIGHT Multiplexed ELISA assay.

Chemokines (MIP 1alpha, MIP1beta, MCP-1, Rantes, 1309, TARC, Eotaxin, MDC, IL8), BDNF, and angiogenic factors (HGF, KGF, bFGF, VEGF, TIMP1, ANG2, PDGFbb, TPO, HB-EGF were measured using SEARCHLIGHT Proteome Arrays (Pierce Biotechnology Inc.). The Proteome Arrays are multiplexed sandwich ELISAs for the quantitative measurement of two to sixteen proteins per well. The arrays are produced by spotting a 2×2, 3×3, or 4×4 pattern of four to sixteen different capture antibodies into each well of a 96-well plate. Following a sandwich ELISA procedure, the entire plate is imaged to capture the chemiluminescent signal generated at each spot within each well of the plate. The signal generated at each spot is proportional to the amount of target protein in the original standard or sample.

II. Results

ELISA assay. MCP-1 and IL-6 were secreted by umbilicus-derived PPDCs and dermal fibroblasts (Table 11-1). SDF-1alpha and GCP-2 were secreted by fibroblasts. GCP-2 and IL-8 were secreted by umbilicus-derived PPDCs. TGF-beta2 was not detected from either cell type by ELISA.

TABLE 11-1

ELISA Results: Detection of Trophic Factors

| | MCP-1 | IL-6 | VEGF | SDF-1 | GCP-2 | IL-8 | TGF-beta |
|---|---|---|---|---|---|---|---|
| Fibroblast | 17 ± 1 | 61 ± 3 | 29 ± 2 | 19 ± 1 | 21 ± 1 | ND | ND |
| Umbilical (022803) | 1150 ± 74 | 4234 ± 289 | ND | ND | 160 ± 11 | 2058 ± 145 | ND |
| Umbilical (071003) | 2794 ± 84 | 1356 ± 43 | ND | ND | 2184 ± 98 | 2369 ± 23 | ND |

Key:
ND: Not Detected.,
=/− sem

SEARCHLIGHT Multiplexed ELISA Assay.

TIMP1, TPO, KGF, HGF, FGF, HBEGF, BDNF, MIP 1beta, MCPJ, RANTES, 1309, TARC, MDC, and IL-8 were secreted from umbilicus-derived PPDCs (Tables 11-2 and 11-3). No Ang2, VEGF, or PDGFbb were detected.

TABLE 11-2

SEARCHLIGHT Multiplexed ELISA assay results

| | TIMP1 | ANG2 | PDGFbb | TPO | KGF | HGF | FGF | VEGF | HBEGF | BDNF |
|---|---|---|---|---|---|---|---|---|---|---|
| hFB | 19306.3 | ND | ND | 230.5 | 5.0 | ND | ND | 27.9 | 1.3 | ND |
| U1 | 57718.4 | ND | ND | 1240.0 | 5.8 | 559.3 | 148.7 | ND | 9.3 | 165.7 |
| U3 | 21850.0 | ND | ND | 1134.5 | 9.0 | 195.6 | 30.8 | ND | 5.4 | 388.6 |

Key:
hFB (human fibroblasts),
U1 (umbilicus-derived PPDC (022803)),
U3 (umbilicus-derived PPDC (071003)).
ND: Not Detected.

TABLE 11-3

SEARCHLIGHT Multiplexed ELISA assay results

| | MIP1a | MIP1b | MCP1 | RANTES | I309 | TARC | Eotaxin | MDC | IL8 |
|---|---|---|---|---|---|---|---|---|---|
| hFB | ND | ND | 39.6 | ND | ND | 0.1 | ND | ND | 204.9 |
| U1 | ND | 8.0 | 1694.2 | ND | 22.4 | 37.6 | ND | 18.9 | 51930.1 |
| U3 | ND | 5.2 | 2018.7 | 41.5 | 11.6 | 21.4 | ND | 4.8 | 10515.9 |

Key:
hFB (human fibroblasts),
U1 (umbilicus-derived PPDC (022803)),
U3 (umbilicus-derived PPDC (071003)).
ND: Not Detected.

Summary.

Umbilicus-derived cells secreted a number of trophic factors. Some of these trophic factors, such as HGF, bFGF, MCP-1 and IL-8, play important roles in angiogenesis. Other trophic factors, such as BDNF and IL-6, have important roles in neural regeneration or protection.

Example 12

In Vitro Immunology

Postpartum cell lines were evaluated in vitro for their immunological characteristics in an effort to predict the immunological response, if any, these cells would elicit upon in vivo administration. Postpartum cell lines were assayed by flow cytometry for the expression of HLA-DR, HLA-DP, HLA-DQ, CD80, CD86, and B7-H2. These proteins are expressed by antigen-presenting cells (APC) and are required for the direct stimulation of naïve CD4' T cells (Abbas & Lichtman, CELLULAR AND MOLECULAR IMMUNOLOGY, 5th Ed. (2003) Saunders, Philadelphia, p. 171). The cell lines were also analyzed by flow cytometry for the expression of HLA-G (Abbas & Lichtman, CELLULAR AND MOLECULAR IMMUNOLOGY, 5th Ed. (2003) Saunders, Philadelphia, p. 171), CD178 (Coumans, et. al., (1999) *Journal of Immunological Methods* 224, 185-196), and PD-L2 (Abbas & Lichtman, CELLULAR AND MOLECULAR IMMUNOLOGY, 5th Ed. (2003) Saunders, Philadelphia, p. 171; Brown, et. al. (2003) *The Journal of Immunology* 170, 1257-1266). The expression of these proteins by cells residing in placental tissues is thought to mediate the immuno-privileged status of placental tissues in utero. To predict the extent to which postpartum umbilicus-derived cell lines elicit an immune response in vivo, the cell lines were tested in a one-way mixed lymphocyte reaction (MLR).

I. Materials and Methods

Cell culture. Cells were cultured in growth medium (DMEM-low glucose (Gibco, Carlsbad, Calif.), 15% (v/v) fetal bovine serum (FBS); (Hyclone, Logan, Utah), 0.001% (v/v) betamercaptoethanol (Sigma, St. Louis, Mo.), 50 Units/milliliter penicillin, 50 micrograms/milliliter streptomycin (Gibco, Carlsbad, Calif.)) until confluent in T75 flasks (Corning, Corning, N.Y.) coated with 2% gelatin (Sigma, St. Louis, Mo.).

Antibody Staining.

Cells were washed in phosphate buffered saline (PBS) (Gibco, Carlsbad, Calif.) and detached with Trypsin/EDTA (Gibco, Carlsbad, Calif.). Cells were harvested, centrifuged, and re-suspended in 3% (v/v) FBS in PBS at a cell concentration of $1 \times 10^7$ per milliliter. Antibody (Table 12-1) was added to one hundred microliters of cell suspension as per manufacturer's specifications and incubated in the dark for 30 minutes at 4° C. After incubation, cells were washed with PBS and centrifuged to remove unbound antibody. Cells were re-suspended in five hundred microliters of PBS and analyzed by flow cytometry using a FACSCalibur™ instrument (Becton Dickinson, San Jose, Calif.).

TABLE 12-1

Antibodies

| Antibody | Manufacturer | Catalog Number |
| --- | --- | --- |
| HLA-DRDPDQ | BD Pharmingen (San Diego, CA) | 555558 |
| CD80 | BD Pharmingen (San Diego, CA) | 557227 |
| CD86 | BD Pharmingen (San Diego, CA) | 555665 |
| B7-H2 | BD Pharmingen (San Diego, CA) | 552502 |
| HLA-G | Abcam (Cambridgeshire, UK) | ab 7904-100 |
| CD 178 | Santa Cruz (San Cruz, CA) | sc-19681 |
| PD-L2 | BD Pharmingen (San Diego, CA) | 557846 |
| Mouse IgG2a | Sigma (St. Louis, MO) | F-6522 |
| Mouse IgG1kappa | Sigma (St. Louis, MO) | P-4685 |

Mixed Lymphocyte Reaction.

Cryopreserved vials of passage 10 umbilical cord-derived PPDCs labeled as cell line A and passage 11 placenta-derived PPDCs labeled as cell line B were sent on dry ice to CTBR (Senneville, Quebec) to conduct a mixed lymphocyte reaction using CTBR SOP no. CAC-031. Peripheral blood mononuclear cells (PBMCs) were collected from multiple male and female volunteer donors. Stimulator (donor) allogeneic PBMC, autologous PBMC, and postpartum-derived cell lines were treated with mitomycin C. Autologous and mitomycin C-treated stimulator cells were added to responder (recipient) PBMCs and cultured for 4 days. After incubation, [$^3$H]thymidine was added to each sample and cultured for 18 hours. Following harvest of the cells, radio labeled DNA was extracted, and [$^3$H]-thymidine incorporation was measured using a scintillation counter.

The stimulation index for the allogeneic donor (SIAD) was calculated as the mean proliferation of the receiver plus mitomycin C-treated allogeneic donor divided by the baseline proliferation of the receiver. The stimulation index of the postpartum-derived cells was calculated as the mean proliferation of the receiver plus mitomycin C-treated postpartum-derived cell line divided by the baseline proliferation of the receiver.

II. Results

Mixed Lymphocyte Reaction-Placenta.

Seven human volunteer blood donors were screened to identify a single allogeneic donor that would exhibit a robust proliferation response in a mixed lymphocyte reaction with the other six blood donors. This donor was selected as the allogeneic positive control donor. The remaining six blood donors were selected as recipients. The allogeneic positive control donor and placenta-derived cell lines were treated with mitomycin C and cultured in a mixed lymphocyte reaction with the six individual allogeneic receivers. Reactions were performed in triplicate using two cell culture plates with three receivers per plate (Table 12-2). The average stimulation index ranged from 1.3 (plate 2) to 3 (plate 1) and the allogeneic donor positive controls ranged from 46.25 (plate 2) to 279 (plate 1) (Table 12-3).

TABLE 12-2

Mixed Lymphocyte Reaction Data - Cell Line B (Placenta)
DPM for Proliferation Assay

| Analytical number | Culture System | Replicates 1 | 2 | 3 | Mean | SD | CV |
|---|---|---|---|---|---|---|---|
| Plate ID: Plate 1 | | | | | | | |
| IM03-7769 | Proliferation baseline of receiver | 79 | 119 | 138 | 112.0 | 30.12 | 26.9 |
| | Control of autostimulation (Mitomycin C treated autologous cells) | 241 | 272 | 175 | 229.3 | 49.54 | 21.6 |
| | MLR allogenic donor IM03-7768 (Mitomycin C treated) | 23971 | 22352 | 20921 | 22414.7 | 1525.97 | 6.8 |
| | MLR with cell line (Mitomycin C treated cell type B) | 664 | 559 | 1090 | 771.0 | 281.21 | 36.5 |
| | SI (donor) | | | | 200 | | |
| | SI (cell line) | | | | 7 | | |
| IM03-7770 | Proliferation baseline of receiver | 206 | 134 | 262 | 200.7 | 64.17 | 32.0 |
| | Control of autostimulation (Mitomycin C treated autologous cells) | 1091 | 602 | 524 | 739.0 | 307.33 | 41.6 |
| | MLR allogenic donor IM03-7768 (Mitomycin C treated) | 45005 | 43729 | 44071 | 44268.3 | 660.49 | 1.5 |
| | MLR with cell line (Mitomycin C treated cell type B) | 533 | 2582 | 2376 | 1830.3 | 1128.24 | 61.6 |
| | SI (donor) | | | | 221 | | |
| | SI (cell line) | | | | 9 | | |
| IM03-7771 | Proliferation baseline of receiver | 157 | 87 | 128 | 124.0 | 35.17 | 28.4 |
| | Control of autostimulation (Mitomycin C treated autologous cells) | 293 | 138 | 508 | 313.0 | 185.81 | 59.4 |
| | MLR allogenic donor IM03-7768 (Mitomycin C treated) | 24497 | 34348 | 31388 | 30077.7 | 5054.53 | 16.8 |
| | MLR with cell line (Mitomycin C treated cell type B) | 601 | 643 | a | 622.0 | 29.70 | 4.8 |
| | SI (donor) | | | | 243 | | |
| | SI (cell line) | | | | 5 | | |
| IM03-7772 | Proliferation baseline of receiver | 56 | 98 | 51 | 68.3 | 25.81 | 37.8 |
| | Control of autostimulation (Mitomycin C treated autologous cells) | 133 | 120 | 213 | 155.3 | 50.36 | 32.4 |
| | MLR allogenic donor IM03-7768 (Mitomycin C treated) | 14222 | 20076 | 22168 | 18822.0 | 4118.75 | 21.9 |
| | MLR with cell line (Mitomycin C treated cell type B) | a | a | a | a | a | a |
| | SI (donor) | | | | 275 | | |
| | SI (cell line) | | | | a | | |
| IM03-7768 (allogenic donor) | Proliferation baseline of receiver | 84 | 242 | 208 | 178.0 | 83.16 | 46.7 |
| | Control of autostimulation (Mitomycin treated autologous cells) | 361 | 617 | 304 | 427.3 | 166.71 | 39.0 |
| Cell line type B | Proliferation baseline of receiver | 126 | 124 | 143 | 131.0 | 10.44 | 8.0 |
| | Control of autostimulation (Mitomycin treated autologous cells) | 822 | 1075 | 487 | 794.7 | 294.95 | 37.1 |
| Plate ID: Plate 2 | | | | | | | |
| IM03-7773 | Proliferation baseline of receiver | 908 | 181 | 330 | 473.0 | 384.02 | 81.2 |
| | Control of autostimulation (Mitomycin C treated autologous cells) | 269 | 405 | 572 | 415.3 | 151.76 | 36.5 |
| | MLR allogenic donor IM03-7768 (Mitomycin C treated) | 29151 | 28691 | 28315 | 28719.0 | 418.70 | 1.5 |
| | MLR with cell line (Mitomycin C treated cell type B) | 567 | 732 | 905 | 734.7 | 169.02 | 23.0 |
| | SI (donor) | | | | 61 | | |
| | SI (cell line) | | | | 2 | | |
| IM03-7774 | Proliferation baseline of receiver | 893 | 1376 | 185 | 818.0 | 599.03 | 73.2 |
| | Control of autostimulation (Mitomycin C treated autologous cells) | 261 | 381 | 568 | 403.3 | 154.71 | 38.4 |
| | MLR allogenic donor IM03-7768 (Mitomycin C treated) | 53101 | 42839 | 48283 | 48074.3 | 5134.18 | 10.7 |
| | MLR with cell line (Mitomycin C treated cell type B) | 515 | 789 | 294 | 532.7 | 247.97 | 46.6 |
| | SI (donor) | | | | 59 | | |
| | SI (cell line) | | | | 1 | | |
| IM03-7775 | Proliferation baseline of receiver | 1272 | 300 | 544 | 705.3 | 505.69 | 71.7 |
| | Control of autostimulation (Mitomycin C treated autologous cells) | 232 | 199 | 484 | 305.0 | 155.89 | 51.1 |
| | MLR allogenic donor IM03-7768 (Mitomycin C treated) | 23554 | 10523 | 28965 | 21014.0 | 9479.74 | 45.1 |
| | MLR with cell line (Mitomycin C treated cell type B) | 768 | 924 | 563 | 751.7 | 181.05 | 24.1 |
| | SI (donor) | | | | 30 | | |
| | SI (cell line) | | | | 1 | | |
| IM03-7776 | Proliferation baseline of receiver | 1530 | 137 | 1046 | 904.3 | 707.22 | 78.2 |
| | Control of autostimulation (Mitomycin C treated autologous cells) | 420 | 218 | 394 | 344.0 | 109.89 | 31.9 |
| | MLR allogenic donor IM03-7768 (Mitomycin C treated) | 28893 | 32493 | 34746 | 32044.0 | 2952.22 | 9.2 |
| | MLR with cell line (Mitomycin C treated cell type B) | a | a | a | a | a | a |
| | SI (donor) | | | | 35 | | |
| | SI (cell line) | | | | a | | |

TABLE 12-3

Average stimulation index of placenta cells and an allogeneic donor in a mixed lymphocyte reaction with six individual allogeneic receivers.

| | Recipient | Placenta |
|---|---|---|
| Plate 1 (receivers 1-3) | 279 | 3 |
| Plate 2 (receivers 4-6) | 46.25 | 1.3 |

Mixed Lymphocyte Reaction—Umbilical Cord.

Six human volunteer blood donors were screened to identify a single allogeneic donor that will exhibit a robust proliferation response in a mixed lymphocyte reaction with the other five blood donors. This donor was selected as the allogeneic positive control donor. The remaining five blood donors were selected as recipients. The allogeneic positive control donor and umbilical cord-derived cell lines were mitomycin C-treated and cultured in a mixed lymphocyte reaction with the five individual allogeneic receivers. Reactions were performed in triplicate using two cell culture plates with three receivers per plate (Table 12-4). The average stimulation index ranged from 6.5 (plate 1) to 9 (plate 2) and the allogeneic donor positive controls ranged from 42.75 (plate 1) to 70 (plate 2) (Table 12-5).

control, and negative expression of CD178 and HLA-G, as noted by fluorescence value consistent with the IgG control (data not shown).

TABLE 12-4

Mixed Lymphocyte Reaction Data - Cell Line A (Umbilical cord)
DPM for Proliferation Assay

| Analytical number | Culture System | Replicates | | | Mean | SD | CV |
|---|---|---|---|---|---|---|---|
| | | 1 | 2 | 3 | | | |
| Plate ID: Plate1 | | | | | | | |
| IM04-2478 | Proliferation baseline of receiver | 1074 | 406 | 391 | 623.7 | 390.07 | 62.5 |
| | Control of autostimulation (Mitomycin C treated autologous cells) | 672 | 510 | 1402 | 861.3 | 475.19 | 55.2 |
| | MLR allogenic donor IM04-2477 (Mitomycin C treated) | 43777 | 48391 | 38231 | 43466.3 | 5087.12 | 11.7 |
| | MLR with cell line (Mitomycin C treated cell type A) | 2914 | 5622 | 6109 | 4881.7 | 1721.36 | 35.3 |
| | SI (donor) | | | | 70 | | |
| | SI (cell line) | | | | 8 | | |
| IM04-2479 | Proliferation baseline of receiver | 530 | 508 | 527 | 521.7 | 11.93 | 2.3 |
| | Control of autostimulation (Mitomycin C treated autologous cells) | 701 | 567 | 1111 | 793.0 | 283.43 | 35.7 |
| | MLR allogenic donor IM04-2477 (Mitomycin C treated) | 25593 | 24732 | 22707 | 24344.0 | 1481.61 | 6.1 |
| | MLR with cell line (Mitomycin C treated cell type A) | 5086 | 3932 | 1497 | 3505.0 | 1832.21 | 52.3 |
| | SI (donor) | | | | 47 | | |
| | SI (cell line) | | | | 7 | | |
| IM04-2480 | Proliferation baseline of receiver | 1192 | 854 | 1330 | 1125.3 | 244.90 | 21.8 |
| | Control of autostimulation (Mitomycin C treated autologous cells) | 2963 | 993 | 2197 | 2051.0 | 993.08 | 48.4 |
| | MLR allogenic donor IM04-2477 (Mitomycin C treated) | 25416 | 29721 | 23757 | 26298.0 | 3078.27 | 11.7 |
| | MLR with cell line (Mitomycin C treated cell type A) | 2596 | 5076 | 3426 | 3699.3 | 1262.39 | 34.1 |
| | SI (donor) | | | | 23 | | |
| | SI (cell line) | | | | 3 | | |
| IM04-2481 | Proliferation baseline of receiver | 695 | 451 | 555 | 567.0 | 122.44 | 21.6 |
| | Control of autostimulation (Mitomycin C treated autologous cells) | 738 | 1252 | 464 | 818.0 | 400.04 | 48.9 |
| | MLR allogenic donor IM04-2477 (Mitomycin C treated) | 13177 | 24885 | 15444 | 17835.3 | 6209.52 | 34.8 |
| | MLR with cell line (Mitomycin C treated cell type A) | 4495 | 3671 | 4674 | 4280.0 | 534.95 | 12.5 |
| | SI (donor) | | | | 31 | | |
| | SI (cell line) | | | | 8 | | |
| Plate ID: Plate 2 | | | | | | | |
| IM04-2482 | Proliferation baseline of receiver | 432 | 533 | 274 | 413.0 | 130.54 | 31.6 |
| | Control of autostimulation (Mitomycin C treated autologous cells) | 1459 | 633 | 598 | 896.7 | 487.31 | 54.3 |
| | MLR allogenic donor IM04-2477 (Mitomycin C treated) | 24286 | 30823 | 31346 | 28818.3 | 3933.82 | 13.7 |
| | MLR with cell line (Mitomycin C treated cell type A) | 2762 | 1502 | 6723 | 3662.3 | 2724.46 | 74.4 |
| | SI (donor) | | | | 70 | | |
| | SI (cell line) | | | | 9 | | |
| IM04-2477 (allogenic donor) | Proliferation baseline of receiver | 312 | 419 | 349 | 360.0 | 54.34 | 15.1 |
| | Control of autostimulation (Mitomycin treated autologous cells) | 567 | 604 | 374 | 515.0 | 123.50 | 24.0 |
| Cell line type A | Proliferation baseline of receiver | 5101 | 3735 | 2973 | 3936.3 | 1078.19 | 27.4 |
| | Control of autostimulation (Mitomycin treated autologous cells) | 1924 | 4570 | 2153 | 2882.3 | 1466.04 | 50.9 |

TABLE 12-5

Average stimulation index of umbilical cord-derived cells and an allogeneic donor in a mixed lymphocyte reaction with five individual allogeneic receivers.

| | Recipient | Umbilical Cord |
|---|---|---|
| Plate 1 (receivers 1-4) | 42.75 | 6.5 |
| Plate 2 (receiver 5) | 70 | 9 |

Antigen Presenting Cell Markers—Placenta.

Histograms of placenta-derived cells analyzed by flow cytometry show negative expression of HLA-DR, DP, DQ, CD80, CD86, and B7-H2, as noted by fluorescence value consistent with the IgG control, indicating that placenta-derived cell lines lack the cell surface molecules required to directly stimulate allogeneic PBMCs (e.g., CD4' T cells).

Immuno-modulating Markers—Placenta-Derived Cells.

Histograms of placenta-derived cells analyzed by flow cytometry show positive expression of PD-L2, as noted by the increased value of fluorescence relative to the IgG Antigen Presenting Cell Markers—Umbilical Cord-Derived Cells.

Histograms of umbilical cord-derived cells analyzed by flow cytometry show negative expression of HLA-DR, DP, DQ, CD80, CD86, and B7-H2, as noted by fluorescence value consistent with the IgG control, indicating that umbilical cord-derived cell lines lack the cell surface molecules required to directly stimulate allogeneic PBMCs (e.g., CD4' T cells).

Immuno-Modulating Markers—Umbilical Cord-Derived Cells.

Histograms of umbilical cord-derived cells analyzed by flow cytometry show positive expression of PD-L2, as noted by the increased value of fluorescence relative to the IgG control, and negative expression of CD178 and HLA-G, as noted by fluorescence value consistent with the IgG control.

Summary.

In the mixed lymphocyte reactions conducted with placenta-derived cell lines, the average stimulation index ranged from 1.3 to 3, and that of the allogeneic positive controls ranged from 46.25 to 279. In the mixed lymphocyte reactions conducted with umbilical cord-derived cell lines, the average stimulation index ranged from 6.5 to 9, and that of the allogeneic positive controls ranged from 42.75 to 70. Placenta- and umbilical cord-derived cell lines were negative for the expression of the stimulating proteins HLA-DR, HLA-DP, HLA-DQ, CD80, CD86, and B7-H2, as measured by flow cytometry. Placenta- and umbilical cord-derived cell lines were negative for the expression of immuno-modulating proteins HLA-G and CD178 and positive for the expression of PD-L2, as measured by flow cytometry. Allogeneic donor PBMCs contain antigen-presenting cells expressing HLA-DP, DR, DQ, CD80, CD86, and B7-H2, thereby allowing for the stimulation of allogeneic PBMCs (e.g., naïve CD4' T cells). The absence of antigen-presenting cell surface molecules on placenta- and umbilical cord-derived cells required for the direct stimulation of allogeneic PBMCs (e.g., naïve CD4' T cells) and the presence of PD-L2, an immuno-modulating protein, may account for the low stimulation index exhibited by these cells in a MLR as compared to allogeneic controls.

Example 13

Plasma Clotting Assay

Cells useful for therapy may be injected systemically for certain applications where the cells are able to target the site of action. It is important that injected cells not cause thrombosis, as it may be fatal. Tissue factor, a membrane-bound procoagulant glycoprotein, is the initiator of the extrinsic clotting cascade, which is the predominant coagulation pathway in vivo. Tissue factor also plays an important role in embryonic vessel formation, for example, in the formation of the primitive vascular wall (Brodsky et al. (2002) *Exp. Nephrol.* 10:299-306). To determine the potential for PPDCs to initiate clotting, umbilicus-derived PPDCs were evaluated for tissue factor expression and for their ability to initiate plasma clotting.

I. Methods & Materials

Human Tissue Factor.

Human tissue factor (SIMPLASTIN, Organon Teknika Corporation, Durham, N.C.), was reconstituted with 20 milliliters distilled water. The stock solution was serially diluted (1:2) in eight tubes. Normal human plasma (George King Bio-Medical, Overland Park, Kans.) was thawed at 37° C. in a water bath and then stored in ice before use. 100 microliters phosphate buffered saline (PBS), 10 microliters diluted SIMPLASTIN, 30 microliters 0.1 Molar calcium chloride, and 100 microliters of normal human plasma were added to each well of a 96-well plate. A negative control well did not receive any SIMPLASTIN. The plate was immediately placed in a temperature-controlled microplate reader and absorbance measured at 405 nanometer at 40 second intervals for 30 minutes.

J-82 and Umbilicus-Derived Cells.

J-82 cells (ATCC, MD) were grown in Iscove's modified Dulbecco's medium (IMDM; Gibco, Carlsbad, Calif.) containing 10% (v/v) fetal bovine serum (FBS; Hyclone, Logan Utah), 1 millimolar sodium pyruvate (Sigma Chemical, St. Louis, Mo.), 2 millimolar L-Glutamine (Mediatech Herndon, Va.), 1× non-essential amino acids (Mediatech Herndon, Va.). At about 70% confluence, cells were transferred at 100,000, 50,000 and 25,000 cells/well to wells of 96-well plate. Umbilicus-derived cells were cultured in growth medium in gelatin-coated T75 flasks (Corning, Corning, N.Y.). Umbilicus-derived cells at passage 18 were transferred to wells at a density of 50,000 cells/well. Culture medium was removed from each well after centrifugation at 150×g for 5 minutes. Cells were suspended in PBS without calcium and magnesium. Cells incubated with anti-tissue factor antibody cells were incubated with 20 micrograms/milliliter CNTO 859 (Centocor, Malvern, Pa.) for 30 minutes. Calcium chloride (30 microliters) was added to each well. The plate was promptly placed in a temperature-controlled microplate reader and absorbance was measured at 405 nanometers at 40 second intervals for 30 minutes.

Antibody Staining.

Cells were washed in PBS and detached from the flask with Trypsin/EDTA (Gibco, Carlsbad, Calif.). Cells were harvested, centrifuged, and resuspended in 3% (v/v) FBS in PBS at a cell concentration of $1 \times 10^7$ per milliliter. Antibody was added to 100 microliters of cell suspension according to the manufacturer's specifications. The cells were incubated in the dark for 30 minutes at 4° C. After incubation, cells were washed with PBS, then centrifuged at 150×g for 5 minutes to remove unbound antibody. Cells were resuspended in 100 microliters of 3% FBS and secondary antibody added in accordance with the manufacturer's instructions. Cells were incubated in the dark for 30 minutes at 4° C. After incubation, cells were washed with PBS and centrifuged to remove unbound secondary antibody. Washed cells were resuspended in 500 microliters of PBS and analyzed via flow cytometry.

Flow Cytometry Analysis.

Flow cytometry analysis was performed with a FACSCalibur™ instrument (Becton Dickinson, San Jose, Calif.).

II. Results

Flow cytometry analysis revealed that umbilicus-derived postpartum cells are less active in promoting plasma clotting than the J82 cells. Although a plasma clotting assay demonstrated that the tissue factor present in the umbilicus-derived cells was active, clotting took longer than with the J-82 cells, as evidenced by the longer time to half-maximal absorbance (T½ to max; Table 13-1). The T ½ to max is inversely proportional to the number of J-82 cells. Umbilicus-derived cells decreased the clotting rate as indicated by the T ½ to max. Clotting was observed with both early (P5) and late (P18) passaged cells. Preincubation of umbilical cells with CNTO 859, an antibody to tissue factor, inhibited the clotting reaction, establishing that tissue factor was responsible for the clotting.

TABLE 13-1

The effect of human tissue factor (Simplastin ®) and umbilicus-derived cells (Umb) on plasma clotting. The time to half maximal absorbance (T ½ to max) at the plateau in seconds was used as a measurement unit.

| | T ½ to max (seconds) |
|---|---|
| Standard (Simplastin ® Dilution) | |
| 1:2 | 61 |
| 1:4 | 107 |
| 1:8 | 147 |
| 1:16 | 174 |
| 1:32 | 266 |
| 1:64 | 317 |
| 1:128 | 378 |
| 0 (negative control) | 1188 |
| J-82 cells | |
| 100,000 | 122 |
| 50,000 | 172 |
| 25,000 | 275 |
| Umb P5 | |
| 50,000 | 833 |

TABLE 13-1-continued

The effect of human tissue factor (Simplastin ®) and umbilicus-derived cells (Umb) on plasma clotting. The time to half maximal absorbance (T ½ to max) at the plateau in seconds was used as a measurement unit.

| | T ½ to max (seconds) |
|---|---|
| Umb P18 | |
| 50,000 | 443 |

Summary.

Umbilicus-derived PPDCs produce some tissue factor, but the addition of an antibody against tissue factor can inhibit the clotting activity of the tissue factor. Tissue factor is normally found on cells in a conformation that is inactive, but which is activated by mechanical or chemical (e.g., LPS) stress (Sakariassen et al. (2001) *Thromb. Res.* 104:149-74; Engstad et al. (2002) *Int. Immunopharmacol.* 2:1585-97). Thus, minimization of stress during the preparation process of PPDCs may prevent activation of tissue factor. In addition to the thrombogenic activity, tissue factor has been associated with angiogenic activity. For this reason, tissue factor activity may be beneficial when umbilicus-derived PPDCs are administered in tissue, but should be inhibited when PPDCs are injected intravenously.

Example 14

Cryopreservation Media for Postpartum-Derived Cells

The objective of this study was to determine a suitable cryopreservation medium for the cryopreservation of postpartum-derived cells.

I. Methods & Materials

Placenta-derived cells grown in growth medium (DMEM-low glucose (Gibco, Carlsbad Calif.), 15% (v/v) fetal bovine serum (Cat. #SH30070.03, Hyclone, Logan, Utah), 0.001% (v/v) betamercaptoethanol (Sigma, St. Louis, Mo.), 50 Units/milliliter penicillin, 50 microgram/milliliter streptomycin (Gibco)), in a gelatin-coated T75 flask were washed with phosphate buffered saline (PBS; Gibco) and trypsinized using 1 milliliter Trypsin/EDTA (Gibco). The trypsinization was stopped by adding 10 milliliter growth medium. The cells were centrifuged at 150×g, supernatant removed, and the cell pellet was resuspended in 1 milliliter growth medium. An aliquot of cell suspension, 60 microliter, was removed and added to 60 microliter ☐trypan blue (Sigma). The viable cell number was estimated using a hemocytometer. The cell suspension was divided into four equal aliquots each containing $88 \times 10^4$ cells each. The cell suspension was centrifuged and resuspended in 1 milliliter of each media below and transferred into Cryovials (Nalgene).

1.) Growth medium +10% (v/v) DMSO (Hybrimax, Sigma, St. Louis, Mo.)
2.) Cell Freezing medium w/DMSO, w/methylcellulose, serum-free (C6295, Sigma, St. Louis, Mo.)
3.) Cell Freezing medium serum-free (C2639, Sigma, St. Louis, Mo.)
4.) Cell Freezing Medium w/glycerol (C6039, Sigma, St. Louis, Mo.)

The cells were cooled at approximately 1° C./min overnight in a −80° C. freezer using a "Mr Frosty" freezing container according to the manufacturer's instructions (Nalgene, Rochester, N.Y.). Vials of cells were transferred into liquid nitrogen for 2 days before thawing rapidly in a 37° C. water bath. The cells were added to 10 milliliter growth medium and centrifuged before the cell number and viability was estimated as before. Cells were seeded onto gelatin-coated flasks at 5,000 cells/cm² to determine whether the cells would attach and proliferate.

II. Results

The initial viability of the cells to be cryopreserved was assessed by trypan blue staining to be 100%.

There was a commensurate reduction in cell number with viability for C6295 due to cells lysis. The viable cells cryopreserved in all four solutions attached, divided, and produced a confluent monolayer within 3 days. There was no discernable difference in estimated growth rate.

Summary.

The cryopreservation of cells is one procedure available for preparation of a cell bank or a cell product. Four cryopreservation mixtures were compared for their ability to protect human placenta-derived cells from freezing damage. Dulbecco's modified Eagle's medium (DMEM) and 10% (v/v) dimethylsulfoxide (DMSO) is the preferred medium of those compared for cryopreservation of placenta-derived cells.

The invention claimed is:

1. A method of reducing the accumulation of amyloid plaque proteins in a subject diagnosed with Alzheimer's disease, or having symptoms of Alzheimer's disease, comprising locally administering to a neuritic plaque site in the brain of the subject a composition comprising an undifferentiated population of isolated human umbilical cord-derived cells,
   wherein the isolated human umbilical cord-derived cells are obtained from human umbilical cord tissue substantially free of blood;
   wherein the isolated cells self-renew and expand in culture and do not express CD117; and
   wherein the locally administered undifferentiated population of isolated human umbilical cord-derived cells reduce the accumulation of amyloid plaque proteins in the subject.

2. The method of claim 1, wherein the isolated human umbilical cord-derived cells are administered to cerebral spinal fluid.

3. The method of claim 1, said composition further comprising pharmaceutically acceptable carriers and/or diluents selected from the group consisting of: saline, aqueous buffer solutions, solvents, artificial cerebral spinal fluid, dispersion media composition and a mix thereof.

4. The method of claim 1, wherein the human umbilical cord-derived cells that do not express CD117 further have one or more of the following characteristics:
   expression of CD10, CD13, CD44, CD73, CD90, PDGFr-alpha, and HLA-A,B,C;
   lack of expression of CD31, CD34, CD45, CD141, or HLA-DR,DP,DQ; and
   increased expression of a gene encoding interleukin 8 and reticulon 1, relative to a human cell that is a fibroblast, a mesenchymal stem cell, or an iliac crest bone marrow cell.

5. The method of claim 1, wherein the human umbilical cord-derived cells further have each of the following characteristics:
   expression of CD10, CD13, CD44, CD73, CD90, PDGFr-alpha, and HLA-A,B,C;
   lack of expression of CD31, CD34, CD45, CD117, CD141, or HLA-DR,DP,DQ; and
   increased expression of a gene encoding interleukin 8 and reticulon 1, relative to a human cell that is a fibroblast, a mesenchymal stem cell, or an iliac crest bone marrow cell.

6. A method of treating a subject diagnosed with Alzheimer's disease comprising locally administering to a neuritic plaque site in the brain of the subject a composition comprising an undifferentiated population of isolated human umbilical cord-derived cells,
   wherein the locally administered undifferentiated population of isolated human umbilical cord-derived cells facilitates plaque removal by phagocytic mechanisms,
   wherein the isolated human umbilical cord-derived cells are obtained from human umbilical cord tissue substantially free of blood, and
   wherein the isolated cells self-renew and expand in culture and have following characteristics:
   expression of CD10, CD13, CD44, CD73, CD90, PDGFr-alpha, and HLA-A,B,C;
   lack of expression of CD31, CD34, CD45, CD117, CD141, or HLA-DR,DP,DQ; and
   increased expression of a gene encoding interleukin 8 and reticulon 1, relative to a human cell that is a fibroblast, a mesenchymal stem cell, or an iliac crest bone marrow cell.

7. A method of treating a subject having symptoms of Alzheimer's disease comprising locally administering to a neuritic plaque site in the brain of the subject a composition comprising an undifferentiated population of isolated human umbilical cord-derived cells,
   wherein the locally administered undifferentiated population of isolated human umbilical cord-derived cells facilitates plaque removal by phagocytic mechanisms, wherein the isolated human umbilical cord-derived cells are obtained from human umbilical cord tissue substantially free of blood, and wherein the isolated cells self-renew and expand in culture and have following characteristics:
- expression of CD10, CD13, CD44, CD73, CD90, PDGFr-alpha, and HLA-A,B,C;
- lack of expression of CD31, CD34, CD45, CD117, CD141, or HLA-DR,DP,DQ; and
- increased expression of a gene encoding interleukin 8 and reticulon 1, relative to a human cell that is a fibroblast, a mesenchymal stem cell, or an iliac crest bone marrow cell.

8. The method of claim 1, wherein the cells are not genetically modified to produce therapeutically useful gene products, to produce agents to facilitate or support neural tissue survival, differentiation, phagocytic activity, or to produce factors to recruit progenitor cells to the area of neuritic plaques.

9. The method of claim 6, wherein the cells are not genetically modified to produce therapeutically useful gene products, to produce agents to facilitate or support neural tissue survival, differentiation, phagocytic activity, or to produce factors to recruit progenitor cells to the area of neuritic plaques.

10. The method of claim 7, wherein the cells are not genetically modified to produce therapeutically useful gene products, to produce agents to facilitate or support neural tissue survival, differentiation, phagocytic activity, or to produce factors to recruit progenitor cells to the area of neuritic plaques.

* * * * *

SEQUENCE LISTING

```
<160> NUMBER OF SEQ ID NOS: 10

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gagaaatcca aagagcaaat gg                                              22

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
```

-continued primer

<400> SEQUENCE: 2
agaatggaaa actggaatag g                                              21

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tcttcgatgc ttcggattcc                                                20

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gaattctcgg aatctctgtt g                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ttacaagcag tgcagaaaac c                                              21

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
agtaaacatt gaaaccacag cc                                             22

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tctgcagctc tgtgtgaagg                                                20

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 8
cttcaaaaac ttctccacaa cc                                              22

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cccacgccac gctctcc                                                    17

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tcctgtcagt tggtgctcc                                                  19
```